US012758682B2

United States Patent
(12) United States Patent
Zaltsman et al.

(10) Patent No.: US 12,758,682 B2
(45) **Date of Patent: *Oct. 13, 2026**

(54) COATING COMPRISING ANTI-MICROBIAL PARTICLES, METHODS OF PREPARATION AND USES THEREOF

(71) Applicant: NOBIO LTD., Kadima (IL)

(72) Inventors: Nathan Zaltsman, Hadera (IL); Ervin Itzhak Weiss, Herzliya (IL); Dganit David, Moshav Ahituv (IL)

(73) Assignee: NOBIO LTD., Kadima (IL)

( * ) Notice: Subject to any disclaimer, the term of this patent is extended or adjusted under 35 U.S.C. 154(b) by 1396 days.

This patent is subject to a terminal disclaimer.

(21) Appl. No.: 17/434,203

(22) PCT Filed: Feb. 27, 2020

(86) PCT No.: PCT/IL2020/050231

§ 371 (c)(1),
(2) Date: Aug. 26, 2021

(87) PCT Pub. No.: WO2020/174480

PCT Pub. Date: Sep. 3, 2020

(65) Prior Publication Data

US 2022/0168466 A1 Jun. 2, 2022

Related U.S. Application Data

(60) Provisional application No. 62/811,083, filed on Feb. 27, 2019.

(51) Int. Cl.
*A61L 27/34* (2006.01)
*A01N 25/10* (2006.01)
(Continued)

(52) U.S. Cl.
CPC .............. *A61L 27/34* (2013.01); *A01N 25/10* (2013.01); *A01N 55/00* (2013.01); *A61L 27/16* (2013.01);
(Continued)

(58) Field of Classification Search
None
See application file for complete search history.

(56) References Cited

U.S. PATENT DOCUMENTS

| | | | |
|---|---|---|---|
| 3,972,855 | A | 8/1976 | Martinsson et al. |
| 4,144,122 | A | 3/1979 | Emanuelsson et al. |

(Continued)

FOREIGN PATENT DOCUMENTS

| | | | |
|---|---|---|---|
| CA | 2799833 | C | 4/2016 |
| CN | 101355922 | A | 1/2009 |

(Continued)

OTHER PUBLICATIONS

Chernov'yants MS, et al. "Synthesis and antimicrobial activity of poly(N-methyl-4-vinylpyridinium triiodide)". Translated from the Russian Khimiko-Farmatsevticheskii Zhurnal, vol. 44, No. 2, pp. 13-15, Feb. 2010.

(Continued)

*Primary Examiner* — Celeste A Roney
(74) *Attorney, Agent, or Firm* — PEARL COHEN LLP

(57) ABSTRACT

Coatings comprising anti-microbial active particles are described, with methods of preparation and uses thereof.

4 Claims, 38 Drawing Sheets

(51) Int. Cl.

| | |
|---|---|
| ***A01N 55/00*** | (2006.01) |
| ***A61L 27/16*** | (2006.01) |
| ***A61L 27/18*** | (2006.01) |
| ***A61L 27/26*** | (2006.01) |
| ***A61L 27/54*** | (2006.01) |

(52) U.S. Cl.

CPC ............... *A61L 27/18* (2013.01); *A61L 27/26* (2013.01); *A61L 27/54* (2013.01); *A61L 2300/404* (2013.01); *A61L 2300/606* (2013.01); *A61L 2420/02* (2013.01); *A61L 2420/06* (2013.01)

(56) References Cited

U.S. PATENT DOCUMENTS

| | | | |
|---|---|---|---|
| 5,277,136 | A | 1/1994 | Davis |
| 5,408,022 | A | 4/1995 | Imazato et al. |
| 5,494,987 | A | 2/1996 | Imazato et al. |
| 5,672,368 | A | 9/1997 | Perkins |
| 5,672,638 | A | 9/1997 | Verhoeven et al. |
| 5,733,949 | A | 3/1998 | Imazato et al. |
| 5,798,117 | A | 8/1998 | New et al. |
| 5,954,869 | A | 9/1999 | Elfersy et al. |
| 5,980,868 | A | 11/1999 | Homola et al. |
| 6,039,940 | A | 3/2000 | Perrault et al. |
| 6,113,815 | A | 9/2000 | Elfersy et al. |
| 6,120,587 | A | 9/2000 | Elfersy et al. |
| 6,123,925 | A | 9/2000 | Barry et al. |
| 6,146,688 | A | 11/2000 | Morgan et al. |
| 6,183,248 | B1 | 2/2001 | Chishti et al. |
| 6,251,967 | B1 | 6/2001 | Perichaud et al. |
| 6,355,704 | B1 | 3/2002 | Nakatsuka et al. |
| 6,482,402 | B1 | 11/2002 | Kurtz et al. |
| 6,559,116 | B1 | 5/2003 | Godfroid et al. |
| 6,562,330 | B1 | 5/2003 | Stratford et al. |
| 6,572,926 | B1 | 6/2003 | Morgan et al. |
| 6,607,382 | B1 | 8/2003 | Kuo et al. |
| 6,762,172 | B1 | 7/2004 | Elfersy et al. |
| 6,929,818 | B2 | 8/2005 | Luthra et al. |
| 7,115,421 | B2 | 10/2006 | Grzeda et al. |
| 7,709,694 | B2 | 5/2010 | Batich et al. |
| 7,771,743 | B1 | 8/2010 | Luthra et al. |
| 7,799,888 | B2 | 9/2010 | Arkles et al. |
| 7,851,653 | B2 | 12/2010 | Getman et al. |
| 7,858,141 | B2 | 12/2010 | Getman et al. |
| 8,389,021 | B2 | 3/2013 | Baker |
| 8,439,674 | B2 | 5/2013 | Li et al. |
| 8,455,599 | B2 | 6/2013 | Arkles et al. |
| 8,535,645 | B2 | 9/2013 | Domb et al. |
| 8,999,291 | B2 | 4/2015 | Goodman et al. |
| 9,011,979 | B2 | 4/2015 | Montero Pancera et al. |
| 9,314,407 | B2 | 4/2016 | Blizzard et al. |
| 9,624,384 | B2 | 4/2017 | Mason et al. |
| 9,744,120 | B2 | 8/2017 | Neigel |
| 10,010,080 | B2 | 7/2018 | Neigel |
| 10,159,630 | B2 | 12/2018 | Blizzard et al. |
| 10,328,020 | B1 | 6/2019 | Neigel |
| 10,405,553 | B1 | 9/2019 | Mason et al. |
| 10,531,664 | B2 | 1/2020 | Mason et al. |
| 11,134,676 | B2 | 10/2021 | Zaltsman et al. |
| 11,178,867 | B2 | 11/2021 | Zaltsman et al. |
| 11,384,172 | B2 | 7/2022 | Naruse et al. |
| 2004/0077892 | A1 | 4/2004 | Arkles et al. |
| 2004/0161390 | A1 | 8/2004 | Gallis |
| 2004/0180093 | A1 | 9/2004 | Burton et al. |
| 2005/0079150 | A1 | 4/2005 | Gellman et al. |
| 2005/0277752 | A1 | 12/2005 | Bringley |
| 2006/0018966 | A1 | 1/2006 | Lin et al. |
| 2006/0115782 | A1 | 6/2006 | Li et al. |
| 2006/0115785 | A1 | 6/2006 | Li et al. |
| 2007/0258996 | A1 | 11/2007 | Pradip et al. |
| 2007/0299538 | A1 | 12/2007 | Roeber |
| 2008/0069887 | A1 | 3/2008 | Baran et al. |
| 2008/0226728 | A1 | 9/2008 | Domb et al. |
| 2009/0285886 | A1 | 11/2009 | Van Beek |
| 2010/0004202 | A1 | 1/2010 | Chisholm et al. |
| 2012/0196953 | A1 | 8/2012 | Ziolkowski et al. |
| 2013/0230676 | A1 | 9/2013 | Blizzard |
| 2013/0245049 | A1 | 9/2013 | Chaltin et al. |
| 2014/0308330 | A1 | 10/2014 | Santra et al. |
| 2014/0322287 | A1 | 10/2014 | Onis et al. |
| 2016/0051450 | A1 | 2/2016 | Kashiki et al. |
| 2016/0135470 | A1 | 5/2016 | Agrawal et al. |
| 2016/0235631 | A1 | 8/2016 | Nojiri |
| 2018/0362714 | A1 | 12/2018 | Grubbs et al. |
| 2019/0053487 | A1 | 2/2019 | Zaltsman et al. |
| 2020/0236931 | A1 | 7/2020 | Trainor et al. |

FOREIGN PATENT DOCUMENTS

| | | | |
|---|---|---|---|
| CN | 102469776 | | 5/2012 |
| CN | 103374093 | | 10/2013 |
| CN | 103391924 | | 11/2013 |
| CN | 102838085 | B | 4/2014 |
| CN | 102549082 | B | 1/2015 |
| CN | 105940062 | A | 9/2016 |
| CN | 106567259 | A | 4/2017 |
| DE | 102012003117 | A1 | 8/2013 |
| DE | 102009047589 | | 1/2014 |
| EP | 0360962 | A2 | 4/1990 |
| EP | 0537774 | | 4/1993 |
| EP | 0688901 | A2 | 12/1995 |
| EP | 0705590 | A1 | 4/1996 |
| EP | 0607195 | B1 | 4/1999 |
| EP | 0908189 | A2 | 4/1999 |
| EP | 1042005 | A2 | 10/2000 |
| EP | 0980682 | B1 | 11/2003 |
| EP | 1863865 | B1 | 5/2012 |
| EP | 2450058 | A1 | 5/2012 |
| EP | 1841314 | B1 | 3/2014 |
| EP | 3269771 | A1 | 1/2018 |
| FR | 3071729 | A1 | 4/2019 |
| JP | 53130428 | | 11/1978 |
| JP | S63-255220 | A | 10/1988 |
| JP | 02307913 | | 12/1990 |
| JP | 05209020 | | 8/1993 |
| JP | 05229975 | | 9/1993 |
| JP | 06341013 | | 12/1994 |
| JP | 07206621 | | 8/1995 |
| JP | 07215814 | | 8/1995 |
| JP | 08253637 | | 10/1996 |
| JP | 10025218 | | 1/1998 |
| JP | 10139797 | | 5/1998 |
| JP | 10204727 | | 8/1998 |
| JP | 10236914 | | 9/1998 |
| JP | 10236915 | | 9/1998 |
| JP | 2000063290 | | 2/2000 |
| JP | 2001009464 | A | 1/2001 |
| JP | 2002122827 | | 4/2002 |
| JP | 2003104435 | | 4/2003 |
| JP | 2003286151 | | 10/2003 |
| JP | 2003301055 | | 10/2003 |
| JP | 2005179238 | | 7/2005 |
| JP | 2007269637 | | 10/2007 |
| JP | 2008184431 | | 8/2008 |
| JP | 2011038195 | | 2/2011 |
| JP | 4783707 | B2 | 9/2011 |
| JP | 2013501742 | | 1/2013 |
| JP | 2014001166 | A | 1/2014 |
| JP | 2018002642 | A | 1/2018 |
| KR | 10-2012-0117760 | | 10/2012 |
| KR | 10-2013-0124165 | | 11/2013 |
| KR | 10-2015-0115757 | | 10/2015 |
| KR | 20180006705 | A | 1/2018 |
| WO | WO 1993/020775 | A1 | 10/1993 |
| WO | WO 1995/010940 | A1 | 4/1995 |
| WO | WO 2001/090251 | | 11/2001 |
| WO | WO-2005/023931 | | 3/2005 |
| WO | WO 2005/123612 | A2 | 12/2005 |
| WO | WO 2006/070376 | A1 | 7/2006 |
| WO | WO 2008/049250 | A1 | 5/2008 |
| WO | WO 2008/149505 | | 12/2008 |
| WO | WO 2009/027971 | A2 | 3/2009 |

(56) References Cited

FOREIGN PATENT DOCUMENTS

| | | | | |
|---|---|---|---|---|
| WO | WO 2009/091001 | | 7/2009 | |
| WO | WO 2010/091124 | A2 | 8/2010 | |
| WO | WO 2011/036031 | A1 | 3/2011 | |
| WO | WO-2011/020586 | | 8/2011 | |
| WO | WO 2011/097347 | A2 | 8/2011 | |
| WO | WO-2011/150001 | | 12/2011 | |
| WO | WO 2012/021754 | A2 | 2/2012 | |
| WO | WO 2014/058757 | A2 | 8/2014 | |
| WO | WO-2014/121189 | | 8/2014 | |
| WO | WO 2015/104894 | | 7/2015 | |
| WO | 2016/172426 | | 10/2016 | |
| WO | WO-2016/172436 | | 10/2016 | |
| WO | WO 2016/172436 | A1 | 10/2016 | |
| WO | WO 2017/078622 | A1 | 5/2017 | |
| WO | WO 2017/145167 | A1 | 8/2017 | |
| WO | WO-2017145142 | A1 * | 8/2017 | ............. A61P 31/04 |
| WO | WO-2017/104676 | | 7/2018 | |
| WO | WO 2019/043713 | A1 | 3/2019 | |
| WO | WO 2019/078198 | A1 | 4/2019 | |

OTHER PUBLICATIONS

Hartlieb M, et al. "Antimicrobial Polymers: Mimicking Amino Acid Functionality, Sequence Control and Three-dimensional Structure of Host-defense Peptides". Current medicinal chemistry. Jun. 1, 2017; 24(19):2115-40.
Kawabata NA, et al. "Removal of bacteria from water by adhesion to cross-linked poly (vinylpyridinium halide)". Appl. Environ. Microbiol. Jul. 1, 1983;46(1):203-10.
Krishna K. Singh et al, "Synthesis, Characterization and in Vitro Antibacterial Activity of Cinnamyl Amine Derivatives", Indian Journal of Chemistry—Section B (IJC-B), 2014, vol. 53B, No. 7, p. 907-912, https://nopr.niscpr.res.in/handle/123456789/29157.
Kudaibergenov SE. "Polyampholytes: synthesis, characterization and application". Springer Science & Business Media; Published online Feb. 16, 2006.
Larikov et al. "Antimicrobial Surfaces using Covalently Bound Polyallylamine", Biomacromulecules vol. 15, 2014, pp. 169-176.
Martins AF, et al. "Antimicrobial activity of chitosan derivatives containing N-quaternized moieties in its backbone: A review". Int. J. Mol. Sci. 2014, 15, 20800-20832; Published Nov. 13, 2014.
Reinhardt NME. "Chemical surface modification of silica nanoparticles for the labeling of DNA in lipoplexes". These Doctorale. Universite Sciences et Technologies—Bordeaux I. ubmitted on Oct. 2, 2015. Retrieved from the Internet: URL: <https://tel.archives-ouvertes.fr/tel-1208139/file/These_Reinhardt_Nora_2013.pdf.
Sarkyt Kudaibergenov; Werner Jaeger; Andre Laschewsky, "Polymeric Betaines: Synthesis, Characterization, and Application", amolecularpolymers, polymeric betains, oligomers; Advances in polymer science; ISSN 0065-3195, Berlin, Heidelberg, vol. 201, doi:10.1007/12_078, ISBN 978-3-540-31924-5, (Jan. 1, 2006), pp. 157-224, URL: https://www.researchgate.net/publication/225434399_Polymeric_Betaines_Synthesis_Characterization_and_Application.
Xometry, "Polymer vs. Metal: what are the differences?" https://www.xometry.com/resources/materials/polymer-vs-metal/ Accessed Jul. 7, 2023, pp. 1-10.
Xu Q., et al. "Antimicrobial silica particles synthesized via ring-opening grafting of cationic amphiphilic cyclic carbonates: Effects of hyrodphobicity and structure". Polymer Chemistry. 2016;7(12):2192-2201. First published Feb. 29, 2016.
Abramovitz, I., et al. (2013). Antibacterial temporary restorative materials incorporating polyethyleneimine nanoparticles. Quintessence international, 44(3).
Beyth, N., et al. (2006). Antibacterial activity of dental composites containing quaternary ammonium polyethylenimine nanoparticles against *Streptococcus mutans*. Biomaterials, 27(21), 3995-4002.
Beyth, N., et al. (2010). Long-term antibacterial surface properties of composite resin incorporating polyethyleneimine nanoparticles. Quintessence international, 41(10).
Beyth, N., et al. (2010). Polyethyleneimine nanoparticles incorporated into resin composite cause cell death and trigger biofilm stress in vivo. Proceedings of the National Academy of Sciences, 107(51), 22038-22043.
Beyth, N., et al. (2012). Antibacterial activity of dental cements containing quaternary ammonium polyethylenimine nanoparticles. Journal of Nanomaterials, 2012, 58.
Beyth, N., et al. (2013). Rapid Kill—Novel Endodontic Sealer and Enterococcus faecalis. PloS one, 8(11), e78586.
Beyth, N., et al. (2014). Antibacterial dental resin composites. Reactive and Functional Polymers, 75, 81-88.
Beyth, N., et al. (2018). Antimicrobial nanoparticles in restorative composites. In Emerging Nanotechnologies in Dentistry (pp. 35-47). William Andrew Publishing.
Beyth, S., et al. (2013). Antibacterial activity of bone cement containing quaternary ammonium polyethyleneimine nanoparticles. Journal of Antimicrobial Chemotherapy, 69(3), 854-855.
Biosafe. Technical Guide for Performance and Regulatory Compliance—Organosilane Antimicrobials; Provides long-lasting surface protection. Downloaded on Feb. 2017.
Busscher, H. J., et al. (2010). Biofilm formation on dental restorative and implant materials. Journal of dental research, 89(7), 657-665.
Carpenter, A. W., et al. (2012). Dual action antimicrobials: nitric oxide release from quaternary ammonium-functionalized silica nanoparticles. Biomacromolecules, 13(10), 3334-3342.
Domb, A. J., et al. (2013). Quaternary Ammonium Antimicrobial Polymers. MRS Online Proceedings Library Archive, 1569, 97-107.
Dong, H., et al. (2011). Recyclable antibacterial magnetic nanoparticles grafted with quaterized poly (2-(dimethylamino) ethyl methacrylate) brushes. *Biomacromolecules*, 12(4), 1305-1311.
Farah, S., et al. (2013). Crosslinked QA-PEI nanoparticles: synthesis reproducibility, chemical modifications, and stability study. Polymers for Advanced Technologies, 24(5), 446-452.
Farah, S., et al. (2014). Antimicrobial silica particles loaded with quaternary ammonium polyethyleneimine network. Polymers for Advanced Technologies, 25(6), 689-692.
Fuchs, A. D., et al. (2006). Contact-active antimicrobial coatings derived from aqueous suspensions. Angewandte Chemie International Edition, 45(40), 6759-6762.
Guo, F., et al. (2018). A review of the synthesis and applications of polymer-nanoclay composites. Applied Sciences, 8(9), 1696.
Imazato et al., (2000). Cytotoxic effects of composite restorations employing self-etching primers or experimental antibacterial primers. Journal of dentistry, 28(1), 61-67. (Only abstract).
Imazato et al., (2002). Penetration of an antibacterial dentine-bonding system into demineralized human root dentine in vitro. European journal of oral sciences, 110(2), 168-174. (Only abstract).
Imazato et al., (2003). Antibacterial activity of bactericide-immobilized filler for resin-based restoratives. Biomaterials, 24(20), 3605-3609.
International Search Report issued for PCT Application No. PCT/IL2006/000005 dated Mar. 13, 2006.
International Search Report issued for PCT Application No. PCT/IL2016/050219 dated Jun. 16, 2016.
International Search Report issued for PCT Application No. PCT/IL2017/050240 dated Jun. 19, 2017.
International Search Report issued for PCT Application No. PCT/IL2018/050969 dated Nov. 12, 2018.
International Search Report issued for PCT Application No. PCT/IL2018/050970 dated Nov. 11, 2018.
Ionescu, A., et al. (2012). Influence of surface properties of resin-based composites on in vitro *Streptococcus mutans* biofilm development. European journal of oral sciences, 120(5), 458-465. (Only abstract).
Jung et al. "Quantitative Analysis and Efficient Surface Modification of Silica Nanoparticles." Journal of Nanomaterials, vol. 2012, Article ID 593471, pp. 1-8; and Supplementary Information, pp. 1-5. (Year: 2012).
Kataev et al. (2014). Quaternary ammonium derivatives of natural terpenoids. Synthesis and properties. Russian Chemical Bulletin, 63(9), 1884-1900.
Kawabata, N., et al. (1988). Antibacterial activity of soluble pyridinium-type polymers. Appl. Environ. Microbiol., 54(10), 2532-2535.

(56) References Cited

OTHER PUBLICATIONS

Kenawy, E. R., et al. (2006). Biologically active polymers: VII. Synthesis and antimicrobial activity of some crosslinked copolymers with quaternary ammonium and phosphonium groups. Reactive and Functional Polymers, 66(4), 419-429.
Kim, H. W., et al. (2010). Imparting durable antimicrobial properties to cotton fabrics using alginate-quaternary ammonium complex nanoparticles. Carbohydrate polymers, 79(4), 1057-1062.
Kostenko, N., et al. (2012). A synthetic route to quaternary pyridinium salt-functionalized silsesquioxanes. International Journal of Polymer Science, 2012.
Li, P., et al. (2005). Synergistic antibacterial effects of β-lactam antibiotic combined with silver nanoparticles. Nanotechnology, 16(9), 1912.
Li, P., et al. (2011). A polycationic antimicrobial and biocompatible hydrogel with microbe membrane suctioning ability. Nature materials, 10(2), 149.
Lin J., et al. (2002). Bactericidal properties of flat surfaces and nanoparticles derivatized with alkylated polyethylenimines. Biotechnology Progress, 18(5), 1082-1086. (Only the abstracts are provided).
Lin, J., et al. (2003). Mechanism of bactericidal and fungicidal activities of textiles covalently modified with alkylated polyethylenimine. Biotechnology and Bioengineering, 83(2), 168-172. (Only abstract).
Majumdar, P., et al. (2009). Synthesis and antimicrobial activity of quaternary ammonium- functionalized POSS (Q-Poss) and polysiloxane coatings containing Q-POSS. Polymer, 50(5), 1124-1133.
Makvandi et al. (2015). Photocurable, antimicrobial quaternary ammonium-modified nanosilica. Journal of dental research, 94(10), 1401-1407.
Matalon, S., et al. (2003). Surface antibacterial properties of fissure sealants. Pediatric dentistry, 25(1), 43-48.
Melo, L. D., et al. (2010). Antimicrobial particles from cationic lipid and polyelectrolytes. Langmuir, 26(14), 12300-12306.
Michailidis, M., et al. (2017). Modified mesoporous silica nanoparticles with a dual synergetic antibacterial effect. ACS applied materials & interfaces, 9(44), 38364-38372.
Nohr, R. S. et al. (1994). New biomaterials through surface segregation phenomenon: new quaternary ammonium compounds as antibacterial agents. Journal of Biomaterials Science, Polymer Edition, 5(6), 607-619. (Only abstract).
Novotná, E., et al. (2014). Synthesis and Biological Activity of Quaternary Ammonium Salt-Type Agents Containing Cholesterol and Terpenes. Archiv der Pharmazie, 347(6), 381-386.
Ono, M., et al. (2007). Surface properties of resin composite materials relative to biofilm formation. Dental materials journal, 26(5), 613-622.
Pu, Y., et al. (2016). Synthesis and antibacterial study of sulfobetaine/quaternary ammonium- modified star-shaped poly [2-(dimethylamino) ethyl methacrylate]-based copolymers with an inorganic core. Biomacromolecules, 18(1), 44-55.
Reinhardt, N., et al. (2015). Quaternary ammonium groups exposed at the surface of silica nanoparticles suitable for DNA complexation in the presence of cationic lipids. The Journal of Physical Chemistry B, 119(21), 6401-6411.
Richter, A. P., et al. (2015). An environmentally benign antimicrobial nanoparticle based on a silver-infused lignin core. Nature nanotechnology, 10(9), 817.
Rumbaugh, K. P., & Ahmad, I. (2014). Antibiofilm Agents. Springer Series on Biofilms, 8.
Savas, L. A., & Hancer, M. (2015). Montmorillonite reinforced polymer nanocomposite antibacterial film. Applied Clay Science, 108, 40-44.
Sbordone, L., et al. (2003). Oral microbial biofilms and plaque-related diseases: microbial communities and their role in the shift from oral health to disease. Clinical oral investigations, 7(4), 181-188. (Only abstract).
Shalhav, M., et al. (1997). In vitro antibacterial activity of a glass ionomer endodontic sealer. Journal of endodontics, 23(10), 616-619.
Shvero, D. K., et al. (2010). Antibacterial effect of polyethyleneimine nanoparticles incorporated in provisional cements against *Streptococcus mutans*. Journal of Biomedical Materials Research Part B: Applied Biomaterials, 94(2), 367-371.
Shvero, D. K., et al. (2013). Towards antibacterial endodontic sealers using quaternary ammonium nanoparticles. International endodontic journal, 46(8), 747-754.
Shvero, D. K., et al. (2015). Characterisation of the antibacterial effect of polyethyleneimine nanoparticles in relation to particle distribution in resin composite. Journal of dentistry, 43(2), 287-294.
Siedenbiedel, F., et al. (2012). Antimicrobial polymers in solution and on surfaces: overview and functional principles. Polymers, 4(1), 46-71.
Song, J., et al. (2011). Bacterial adhesion inhibition of the quaternary ammonium functionalized silica nanoparticles. Colloids and Surfaces B: Biointerfaces, 82(2), 651-656.
Supplementary Search Report issued for EP Application No. 17 75 5952 dated Sep. 25, 2019.
Takei, et al. (1999). Investigation of the Structure of Surface Hydroxyl Groups on Silica Chemical Reaction and Molecular Adsorption Method. Journal of the Society of Powder Technology, Japan, 36(3), 179-184.
Tu, Q., et al. (2016). Quantum dots modified with quaternized poly (dimethylaminoethyl methacrylate) for selective recognition and killing of bacteria over mammalian cells. Analyst, 141(11), 3328-3336.
Voo, R., et al. (2011). Properties of epoxy nanocomposite thin films prepared by spin coating technique. Journal of Plastic Film & Sheeting, 27(4), 331-346.
Weiss, E. I., et al. (1996). Assessment of antibacterial activity of endodontic sealers by a direct contact test. Dental Traumatology, 12(4), 179-184.
Wytrwal et al. (2014). "Synthesis of strong polycations with improved biological properties". Journal of Biomedical Materials Research Part A, 102(3), 721-731.
Xu, Q., et al. (2015). Polyurethane-coated silica particles with broad-spectrum antibacterial properties. Polymer Chemistry, 6(11), 2011-2022.
Yahiaoui, F., et al. (2015). Development of antimicrobial PCL/nanoclay nanocomposite films with enhanced mechanical and water vapor barrier properties for packaging applications. Polymer Bulletin, 72(2), 235-254.
Yudovin-Farber, I., et al. (2008). Surface characterization and biocompatibility of restorative resin containing nanoparticles. Biomacromolecules, 9(11), 3044-3050.
Yudovin-Farber, I., et al. (2010). Antibacterial effect of composite resins containing quaternary ammonium polyethyleneimine nanoparticles. Journal of Nanoparticle Research, 12(2), 591-603.
Yudovin-Farber, I., et al. (2010). Quaternary ammonium polyethyleneimine: antibacterial activity. Journal of nanomaterials, 2010, 46.
Zaltsman, N., et al. (2017). Surface-modified nanoparticles as anti-biofilm filler for dental polymers. PloS one, 12(12), e0189397.

* cited by examiner

D'

E'

F

E'

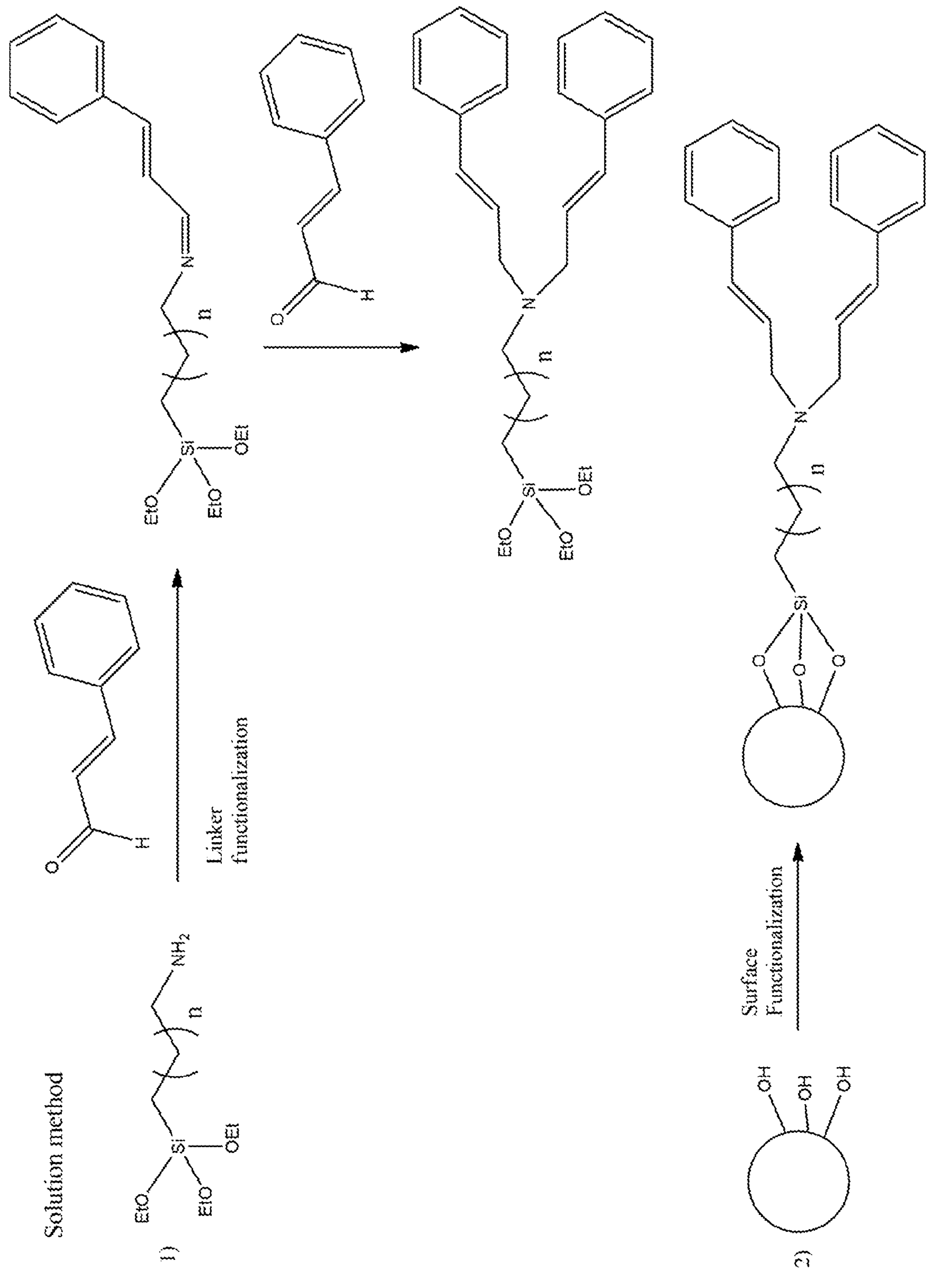
FIGURE 7 - continued

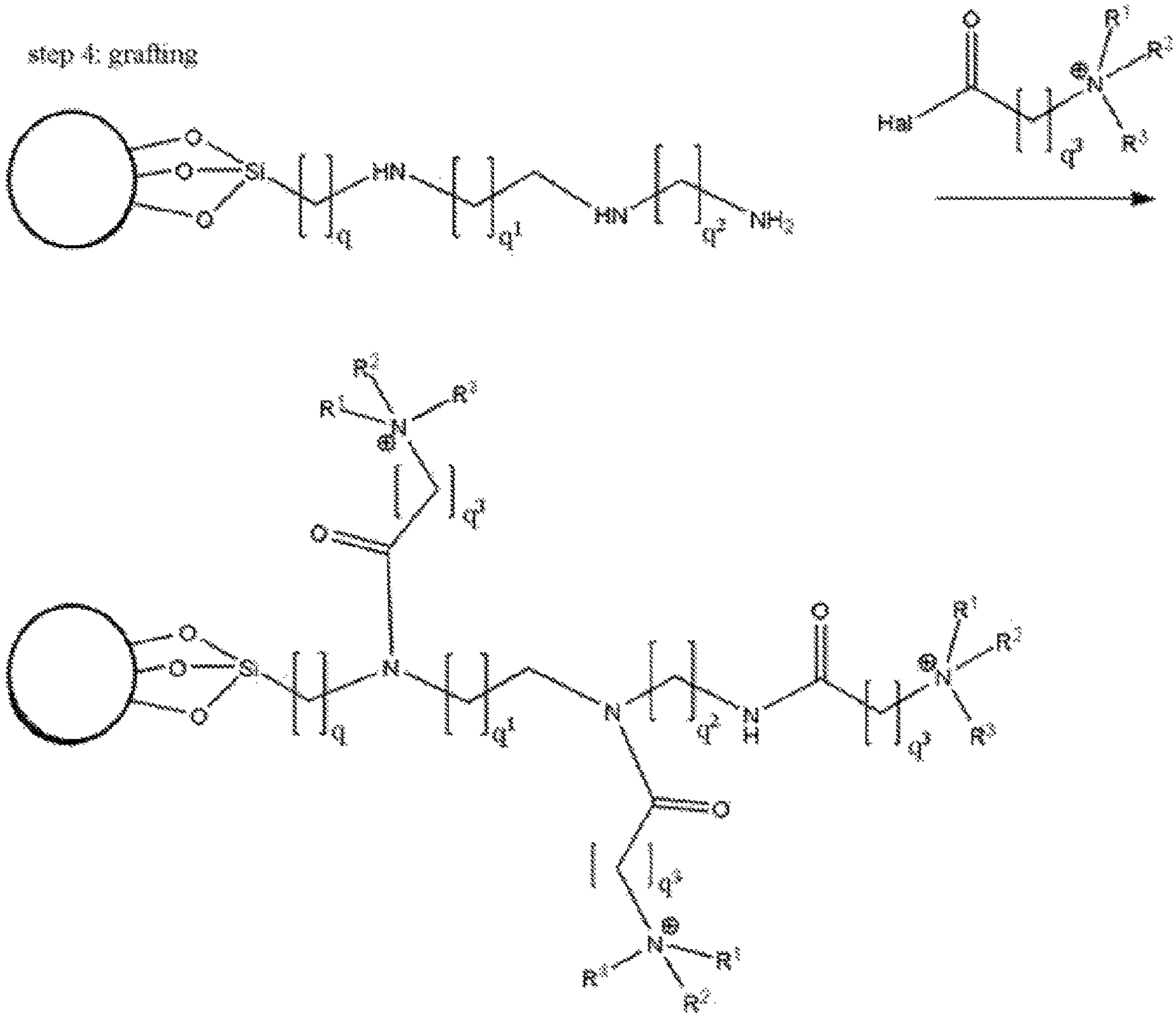
FIGURE 8 - continued

Step 1: linker attachment

Step 2: elongation (I)

Step 3: elongation (II)

step 4: grafting

FIGURE 9 - continued

Mode B

Mode A

Solution method

Step 1: linker elongation (I)

Step 2: linker elongation (II)

step 3: grafting step 4: particle functionalization
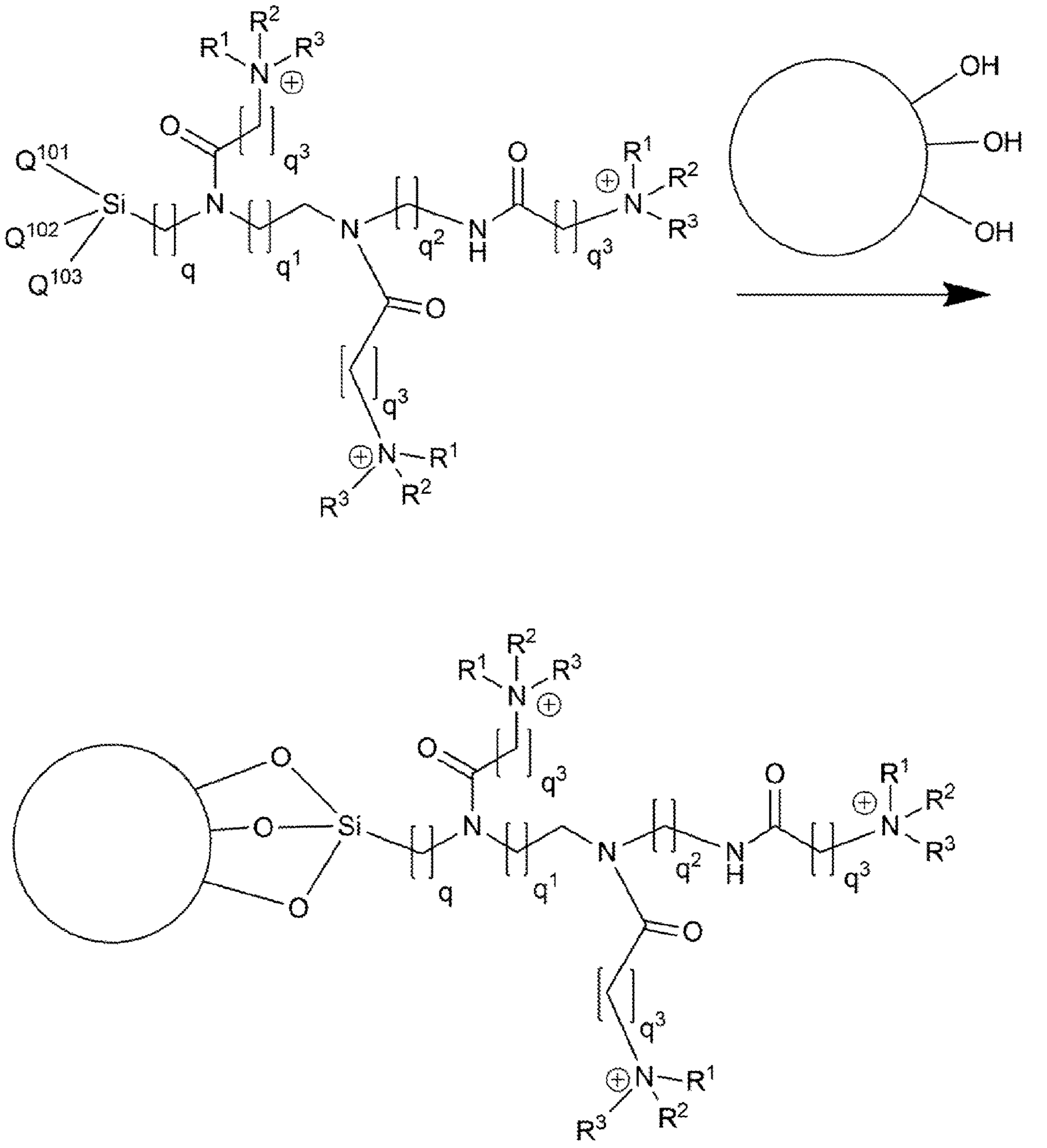
FIGURE 12 - continued

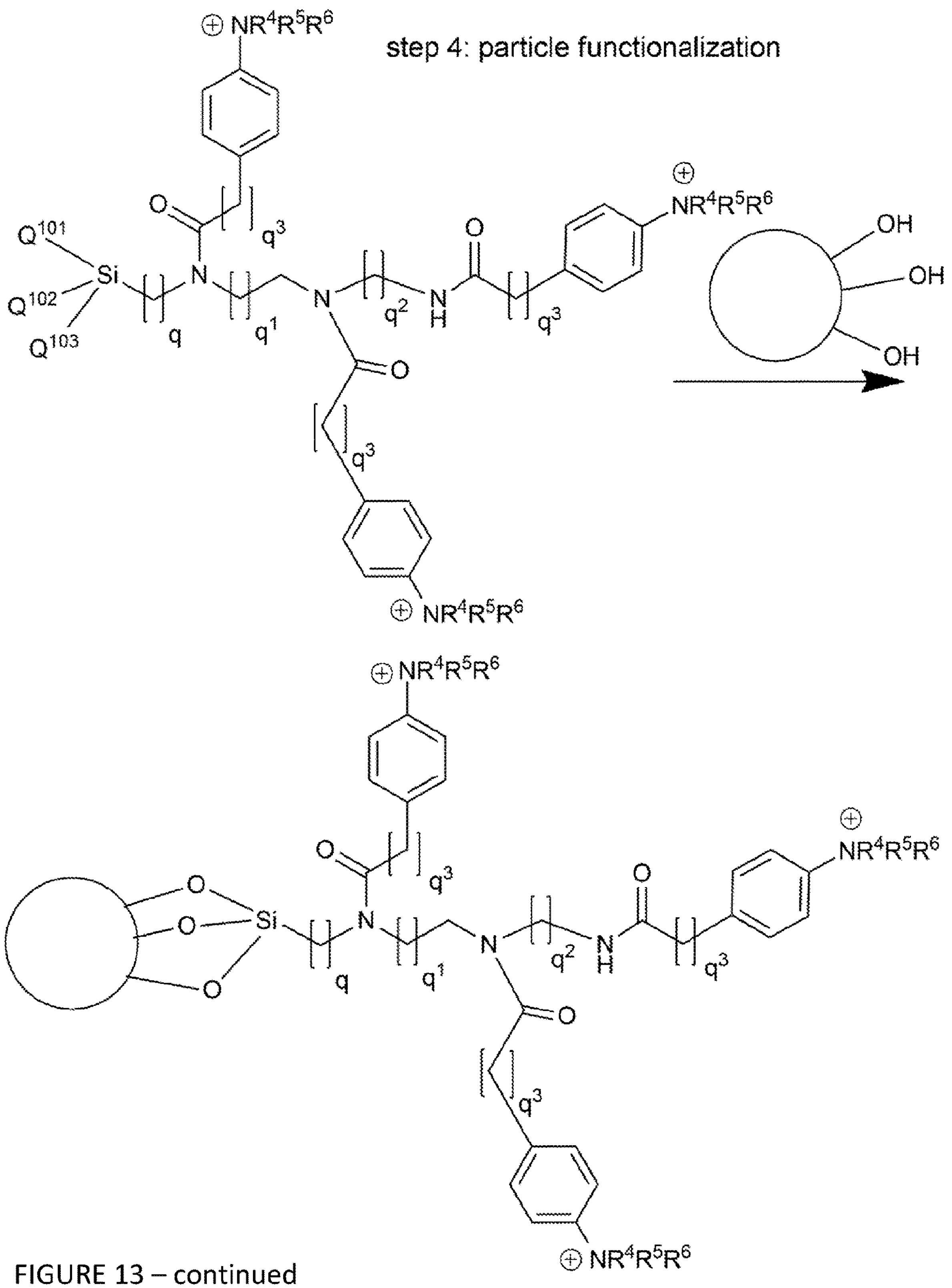
FIGURE 13 – continued

Solid support method

Step 1: linker attachment

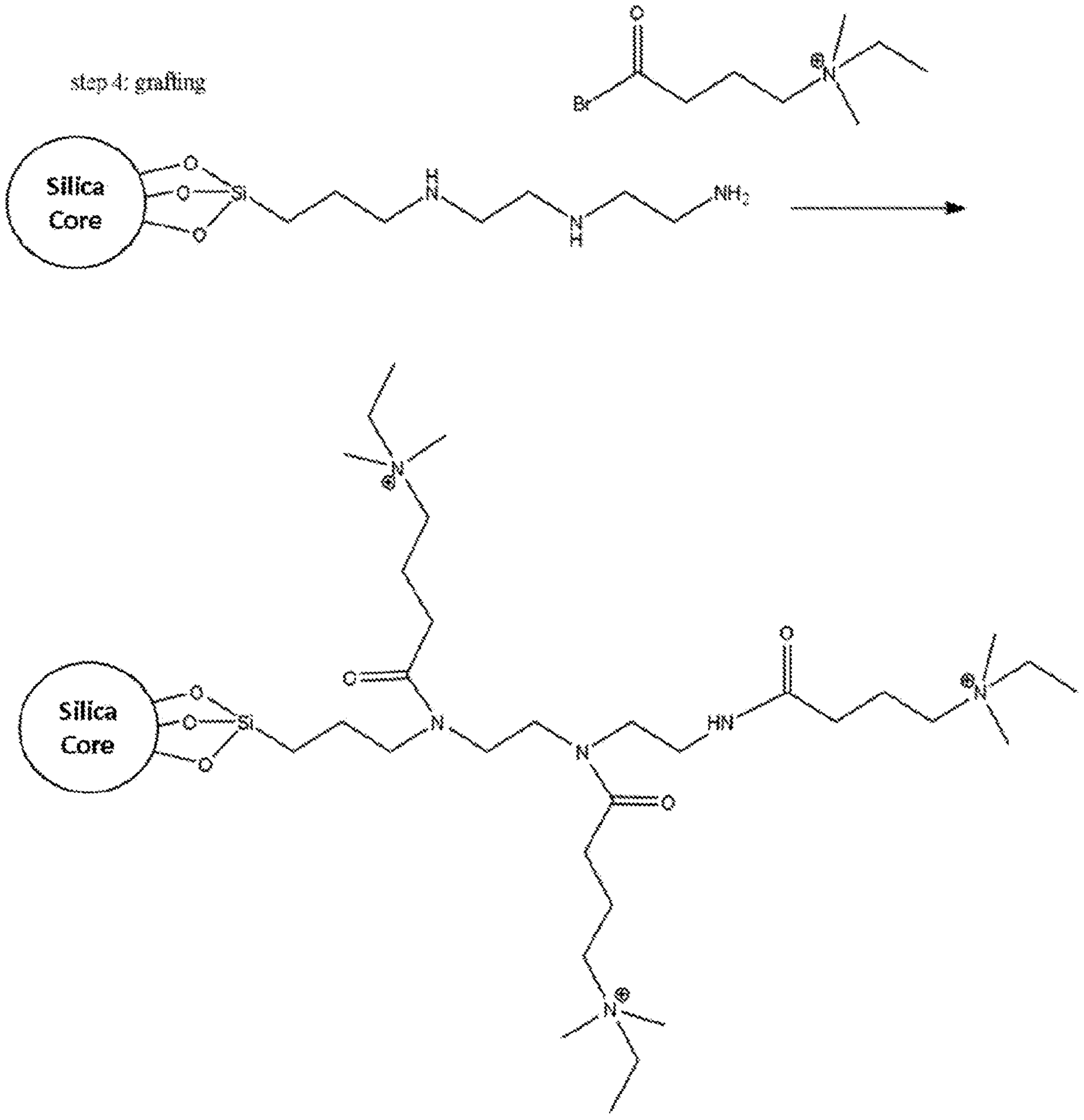
FIGURE 14 – continued

Solution method

Step 1: linker elongation (I)

Step 2: linker elongation (II)

Step 3: grafting

Step 4: particle functionalization
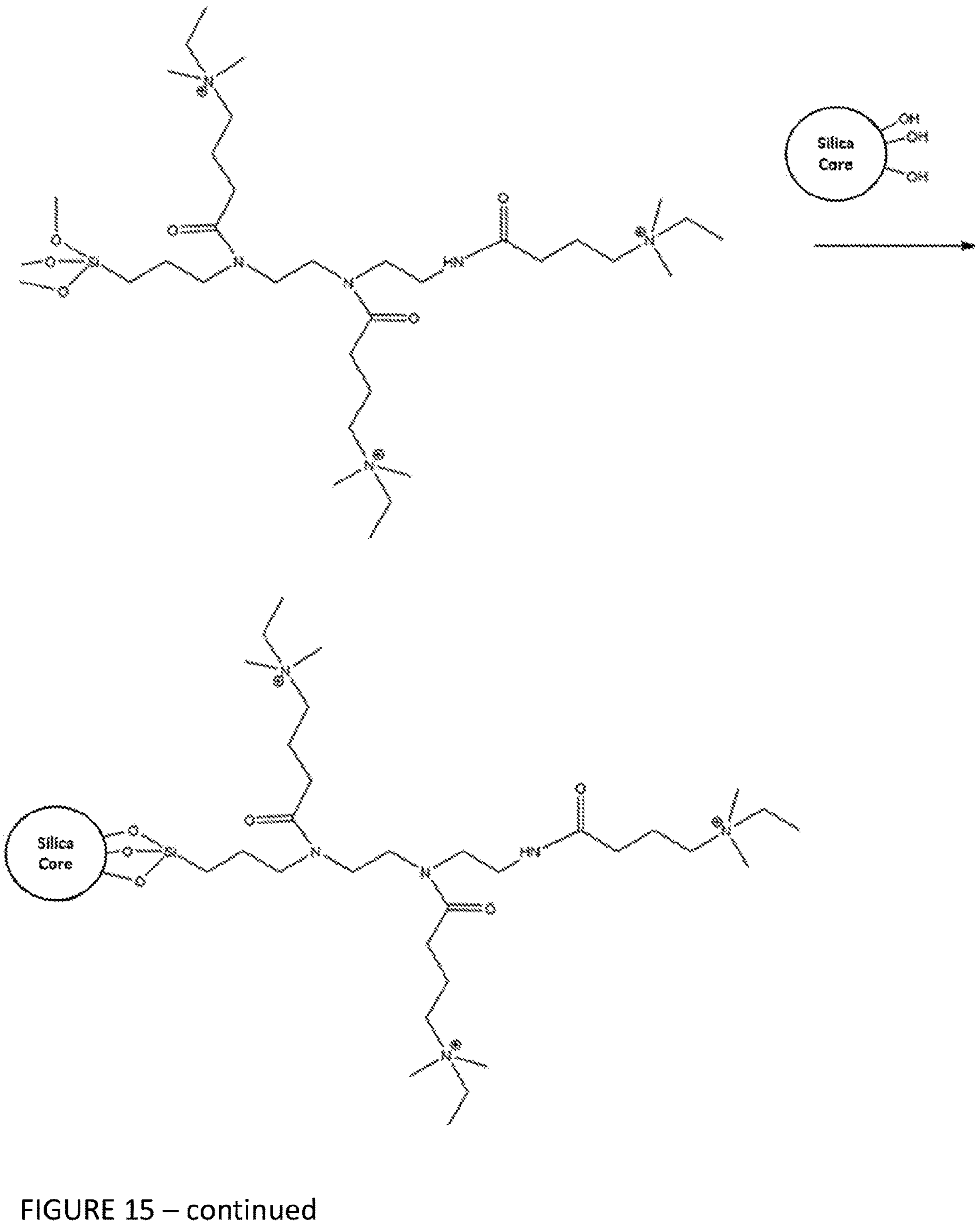
FIGURE 15 – continued

Solid support method

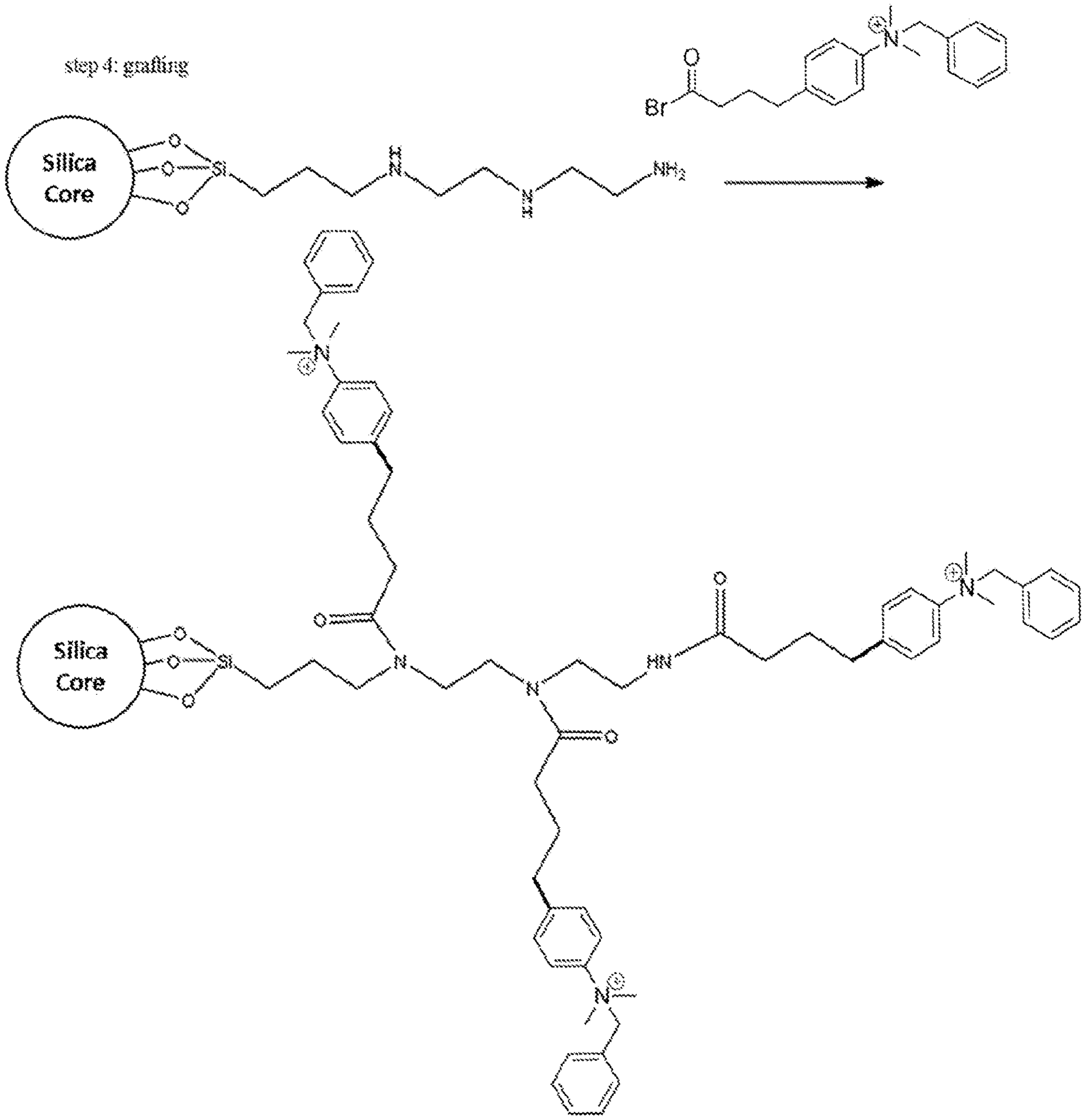
FIGURE 16 – continued

Solution method

Step 1: linker elongation (I)

Step 2: linker elongation (II)

Step 3: grafting

Step 4: particle functionalization
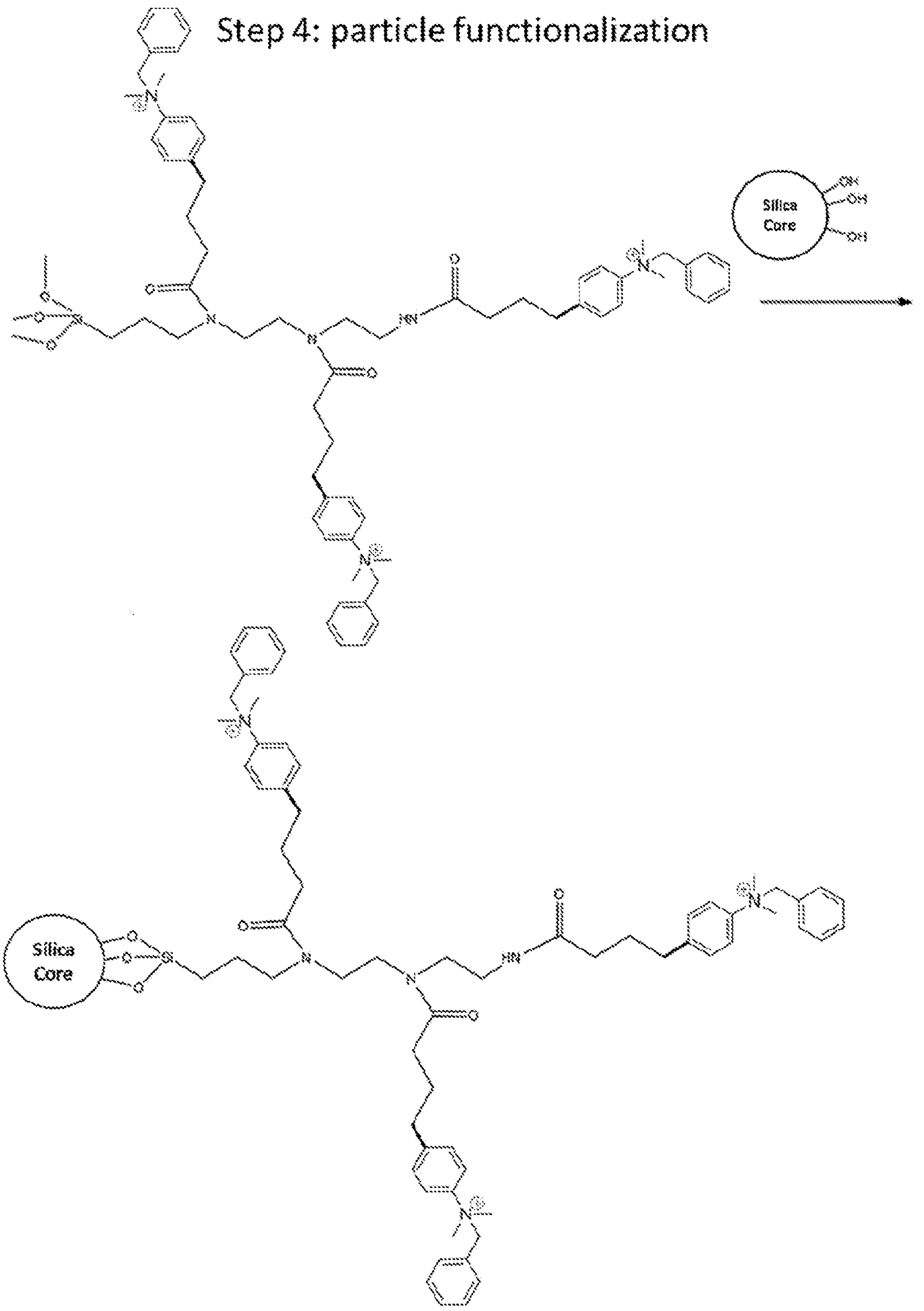
FIGURE 17 – continued

COATING COMPRISING ANTI-MICROBIAL PARTICLES, METHODS OF PREPARATION AND USES THEREOF

CROSS-REFERENCE TO RELATED APPLICATIONS

This application is a National Phase Application of PCT International Application No. PCT/IL2020/050231, International Filing Date Feb. 27, 2020, claiming the benefit of U.S. Patent Application No. 62/811,083, filed Feb. 27, 2019, which are hereby incorporated by reference.

FIELD OF THE INVENTION

This invention relates to coatings comprising anti-microbial particles, methods of preparation and uses thereof.

BACKGROUND OF THE INVENTION

The overwhelming diversity of bacteria in one individual's skin, gastro intestinal tract and oral cavity is well documented, demonstrating a complex ecosystem anatomically and dynamically in which poly-microbial biofilms are the norm.

Biofilms formed on tissues outside and inside the organism are the major cause of infectious diseases. For example in the oral cavity, biofilm formed on dental hard or soft tissue are the major cause of caries and periodontal disease (Sbordone L., Bortolaia C., *Clin Oral Investig* 2003; 7:181-8). Bacterial biofilm forms on both natural and artificial surfaces.

Special attention is paid in recent years to artificial surfaces contacting organisms, as these surfaces lack the epithelial shedding, a major natural mechanism to combat biofilms, thus biofilm accumulation is becoming a major source of medical problems that may result in life threatening complications. Two major factors influence the susceptibility of a surface to accumulate bacteria: surface roughness and the surface-free energy which is a property of the material used. Surface roughness has a higher influence on the adhesion of bacteria than surface-free energy. In this context, artificial restorative materials typically have a higher surface roughness than natural surfaces, and therefore are more prone to bacterial accumulation. Therefore, the development of new materials that diminishes biofilm formation is a critical topic.

The ultimate goal of the development of materials with antibiofilm properties is to improve health and reduce disease occurrence. None of the existing medical devices can guarantee immediate and comprehensive elimination of biofilm or prevention of secondary infection.

For example, in order to sustain the oral defense, dental materials with the following antibiofilm properties are sought after: (1) inhibition of initial binding of microorganisms (2) preventing biofilm growth, (3) affecting microbial metabolism in the biofilm, (4) killing biofilm bacteria, and (5) detaching biofilm (Busscher H J, Rinastiti M, Siswomihardjo W, van der Mei H C., *J Dent Res,* 2010; 89:657-65; Marsh P D. *J Dent,* 2010; 38).

Resin-based composites are complex dental materials that consist of a hydrophobic resin matrix and less hydrophobic filler particles, which implies that a resin-based composite surface is never a homogeneous interface but rather one that produces matrix-rich and filler-poor areas, as well as matrixpoor and filler-rich areas (Ionescu A, Wutscher E, Brambilla E, Schneider-Feyrer S, Giessibl F J, Hahnel S.; *Eur J Oral Sci* 2012; 120:458-65).

Biofilms on composites can cause surface deterioration. Polishing, as well as differences in the composition of the resin-based composite, may have an impact on biofilm formation on the resin-based composite surface (Ono M. et al., *Dent Mater J,* 2007; 26:613-22). Surface degradation of resin composites driven by polishing leads to increased roughness, changes in micro hardness, and filler particle exposure upon exposure to biofilms in vitro. Furthermore, biofilms on composites can cause surface deterioration.

There still remains a need for and it would be advantageous to have an extended variety of anti-microbial active coatings, which are cost-effective, non-toxic and easy to apply on substrates.

SUMMARY OF THE INVENTION

In one embodiment, this invention provides a coating comprising anti-microbial particles and a matrix, wherein the particles comprise:

(i) an inorganic or organic core; and (ii) an anti-microbial active unit chemically bound to the core; wherein the anti-microbial active unit is connected directly (via a bond) or indirectly (via a third linker) to the core;

wherein the anti-microbial active unit comprises a monomeric unit comprising an anti-microbial active group; and wherein the number of the anti-microbial active groups per each anti-microbial active unit is between 1-200.

In another embodiment, the particles are represented by structure (1) or (I):

(1)

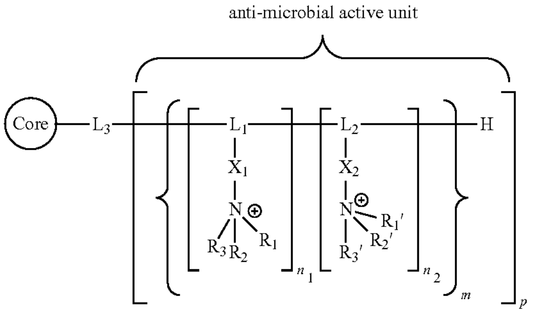

wherein the core is an organic polymer or an inorganic material;

$L_1$ is a first linker or a bond;

$L_2$ is a second linker;

$L_3$ is a third linker or a bond;

$R_1$ and $R_1'$ are each independently alkyl, terpenoid, cycloalkyl, aryl, heterocycle, alkenyl, alkynyl or any combination thereof;

$R_2$ and $R_2'$ are each independently alkyl, terpenoid, cycloalkyl, aryl, heterocycle, alkenyl, alkynyl or any combination thereof;

$R_3$ and $R_3'$ are each independently nothing, hydrogen, alkyl, terpenoid moiety, cycloalkyl, aryl, heterocycle, a conjugated alkyl, alkenyl, alkynyl or any combination thereof; wherein if $R_3$ or $R_3'$ are nothing, the nitrogen is not charged;

$X_1$ and $X_2$ is each independently a bond, alkylene, alkenylene, or alkynylene;

p defines the number of anti-microbial active units per one sq nm ($nm^2$) of the core surface, wherein said density is of between 0.01-30 anti-microbial units per one sq nm ($nm^2$) of the core surface of the particle;

$n_1$ is each independently an integer between 0 to 200;

$n_2$ is each independently an integer between 0 to 200;

wherein $n_1+n_2 \geq 1$; and m is an integer between 1 to 200 and the repeating unit is the same or different; or

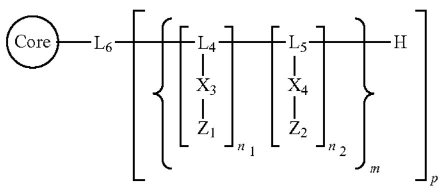

(I)

wherein the core is an organic polymer or an inorganic material;

$L_4$ is a first linker or a bond;

$L_5$ is a second linker;

$L_6$ is a third linker or a bond;

$Z_1$ is

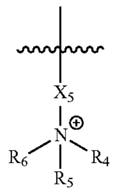

or

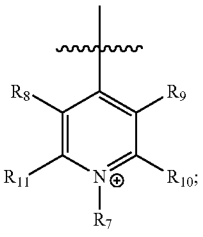

$Z_2$ is

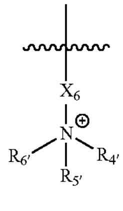

or

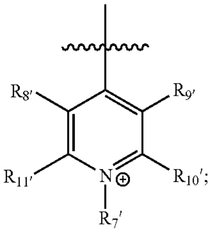

$R_4$ and $R_4'$ are each independently methyl, $CF_3$, perhaloalkyl, aryl, benzyl, 2,2-disubstituted $C_3$-$C_{20}$ alkyl, 2,2,2-trisubstituted ethyl, —$CH_2C$(═O)OR, —$CH_2C$(═O)OC(═O)R, —$CH_2C$(═S)OR, —$CH_2C$(═O)SR, —C(═O)OR, —C(═O)OC(═O)R, —C(═S)OR, —C(═O)SR, —C(═O)—R, —C(═S)—R, —$CH_2C$(═O)R, —$CH_2C$(═S)R, —$CH_2CF_3$, —$CH_2NO_2$, 1-alkenyl, 1-alkynyl, 2-alkenyl, 2-alkynyl or any combination thereof;

$R_5$ and $R_5'$ are each independently methyl, $CF_3$, perhaloalkyl, aryl, benzyl, 2,2-disubstituted $C_3$-$C_{20}$ alkyl, 2,2,2-trisubstituted ethyl, —$CH_2C$(═O)OR, —$CH_2C$(═O)OC(═O)R, —$CH_2C$(═S)OR, —$CH_2C$(═O)SR, —C(═O)OR, —C(═O)OC(═O)R, —C(═S)OR, —C(═O)SR, —C(═O)—R, —C(═S)—R, —$CH_2C$(═O)R, —$CH_2C$(═S)R, —$CH_2CF_3$, —$CH_2NO_2$, 1-alkenyl, 1-alkynyl, 2-alkenyl, 2-alkynyl or any combination thereof;

$R_6$ and $R_6'$ are each independently absent, methyl, $CF_3$, perhaloalkyl, 2,2-disubstituted $C_3$-$C_{20}$ alkyl, 2,2,2-trisubstituted ethyl, —$CH_2C$(═O)OR, —$CH_2C$(═O)OC(═O)R, —$CH_2C$(═S)OR, —$CH_2C$(═O)SR, —C(═O)OR, —C(═O)OC(═O)R, —C(═S)OR, —C(═O)SR, —C(═O)—R, —C(═S)—R, —$CH_2C$(═O)R, —$CH_2C$(═S)R, —$CH_2CF_3$, —$CH_2NO_2$, terpenoid moiety, cycloalkyl, aryl, phenyl, benzyl, heterocycle, a conjugated alkyl, 1-alkenyl, 1-alkynyl, 2-alkenyl, 2-alkynyl or any combination thereof;

$R_7$ and $R_7'$ are each independently methyl, $CF_3$, perhaloalkyl, aryl, benzyl, 2,2-disubstituted $C_3$-$C_{20}$ alkyl, 2,2,2-trisubstituted ethyl, —$CH_2C$(═O)OR, —$CH_2C$(═O)OC(═O)R, —$CH_2C$(═S)OR, —$CH_2C$(═O)SR, —C(═O)OR, —C(═O)OC(═O)R, —C(═S)OR, —C(═O)SR, —C(═O)—R, —C(═S)—R, —$CH_2C$(═O)R, —$CH_2C$(═S)R, —$CH_2CF_3$, —$CH_2NO_2$, 1-alkenyl, 1-alkynyl, 2-alkenyl, 2-alkynyl or any combination thereof;

$R_8$ and $R_8'$ are each independently H, alkyl, terpenoid moiety, cycloalkyl, aryl, heterocycle, a conjugated alkyl, alkenyl, alkynyl or any combination thereof;

$R_9$ and $R_9'$ are each independently H, alkyl, terpenoid moiety, cycloalkyl, aryl, heterocycle, a conjugated alkyl, alkenyl, alkynyl or any combination thereof;

$R_{10}$ and $R_{10}'$ are each independently H, alkyl, terpenoid moiety, cycloalkyl, aryl, heterocycle, a conjugated alkyl, alkenyl, alkynyl or any combination thereof;

$R_{11}$ and $R_{11}'$ are each independently H, alkyl, terpenoid moiety, cycloalkyl, aryl, heterocycle, a conjugated alkyl, alkenyl, alkynyl or any combination thereof;

$X_3$ and $X_4$ are each independently a bond, alkylene, arylene, alkenylene, alkynylene or any combination thereof;

$X_5$ and $X_6$ are each independently a bond, —O—C(═O)—, methylene, —O—C(═O)—$CH_2$—, 2,2-disubstituted $C_2$-$C_{20}$ alkylene, arylene, phenylene, benzylene, cycloalkylene, a heterocycle, a conjugated alkylene, a terpenoid moiety, 1-alkenylene, 1-alkynylene, 2-alkenylene, 2-alkynylene or any combination thereof;

R is alkyl, aryl, cycloalkyl, heterocycle or any combination thereof;

p defines the number of anti-microbial active unit per one sq nm ($nm^2$) of the core surface, wherein said density is of between 0.01-30 anti-microbial units per one sq nm ($nm^2$) of the core surface of the particle;

$n_1$ is each independently an integer between 0 to 200;

$n_2$ is each independently an integer between 0 to 200;

wherein $n_1+n_2 \geq 1$; and m is an integer between 1 to 200 and the repeating unit is the same or different.

In one embodiment, this invention provides a coated substrate comprising a matrix, anti-microbial particles and a substrate.

In one embodiment, this invention provides a process of preparing a coated substrate wherein said process comprises:

dissolving anti-microbial particles and a matrix material in a solvent to form a solution; and coating a substrate with the solution to provide a substrate having an anti-microbial coating.

In one embodiment, this invention provides a process of preparing a coated substrate, the process comprises:

dissolving anti-microbial particles and a monomer, oligomer or a pre-polymerized substance that can undergo polymerization, cross linking and/or vulcanization in a solvent to form a solution;

coating a substrate with the solution; and polymerizing, cross linking and/or vulcanizing the substrate coated with the solution to provide a substrate having an anti-microbial coating.

In one further embodiment, this invention provides a process of preparing a coated substrate, the process comprises:

pouring a dry anti-microbial composition onto a substrate;

melting the dry composition by heat; and cooling the melt to provide a substrate having an anti-microbial coating;

wherein said dry anti-microbial composition comprises said anti-microbial particles and said matrix.

In one further embodiment, this invention provides a process of preparing a coated substrate, the process comprises:

pouring a dry matrix composition onto a substrate;

melting the poured dry matrix composition by heat;

pouring dry anti-microbial particles into the melt to provide a mixture of a melted dry matrix composition and anti-microbial particles; and cooling the mixture to provide a substrate having an anti-microbial coating;

wherein said dry matrix composition comprises said matrix.

In one further embodiment, this invention provides a coated substrate prepared according to any of the processes described hereinabove.

In one further embodiment, this invention provides a method for inhibiting or preventing biofilm formation or growth, comprising applying onto a susceptible or infected surface or a medical device a coating comprising anti-microbial particles and a matrix.

In one embodiment, this invention provides a method for inhibition of bacteria, comprising contacting the bacteria with a coated substrate comprising a matrix, anti-microbial particles and a substrate.

In one further embodiment, this invention provides a medical device comprising a coated substrate comprising a matrix, anti-microbial particles and a substrate.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 1A: an oligomeric/polymeric backbone per one anti-microbial active unit; FIG. 1B: a monomeric backbone per one anti-microbial active unit; and FIG. 1C: detailed monomeric unit scheme.

FIG. 4A) by reductive amination to achieve tertiary amine, followed by an alkylation reaction; FIG. 4B) by stepwise alkylation reactions; and FIG. 4C): by reacting a linker functionalized with a leaving group (e.g., Cl or other halogen) with tertiary amine. $R^1$ and $R^2$ represent $C_1$-$C_4$ alkyls such as methyl, ethyl, propyl or isopropyl. $R^1$ and $R^2$ may be different or the same group. Y represents any leaving group, for example Cl, Br or I, or a sulfonate (e.g., mesyl, tosyl).

FIG. 5A) by alkylation with $R_1$—Y/$R_2$—Y to achieve tertiary amine, followed by an benzylation reaction; FIG. 5B) by a similar pathway as in A), done in the reversed order; and FIG. 5C): by reacting a linker functionalized with a leaving group (e.g., Cl or other halogen) with tertiary amine. $R_4$ and $R_5$ are independently methyl, $CF_3$, perhaloalkyl, aryl, benzyl, 2,2-disubstituted $C_3$-$C_{20}$ alkyl, 2,2,2-trisubstituted ethyl, —$CH_2C$(═O)OR, —$CH_2C$(═O)OC(═O)R, —$CH_2C$(═S)OR, —$CH_2C$(═O)SR, —C(═O)OR, —C(═O)OC(═O)R, —C(═S)OR, —C(═O)SR, —$CH_2C$(═O)R, —$CH_2C$(═S)R, —$CH_2CF_3$, —$CH_2NO_2$, 1-alkenyl, 1-alkynyl, 2-alkenyl, 2-alkynyl or any combination thereof; where R is alkyl, aryl, cycloalkyl, heterocycle or any combination thereof. Y represents any leaving group, for example Cl, Br or I, or a sulfonate (e.g., mesyl, tosyl).

FIG. 10A: self-polymerization of trialkoxysilane linker via solid support method;

FIG. 10B: self-polymerization of trialkoxysilane linker in solution; and FIG. 10C: comparison of polymerization of the silane groups versus simple silanization.

FIG. 11A: self-polymerization of trialkoxysilane linker via solid support method; FIG. 11B: self-polymerization of trialkoxysilane linker in solution; and FIG. 11C: comparison of polymerization of the silane groups versus simple silanization.

Figure 1A:
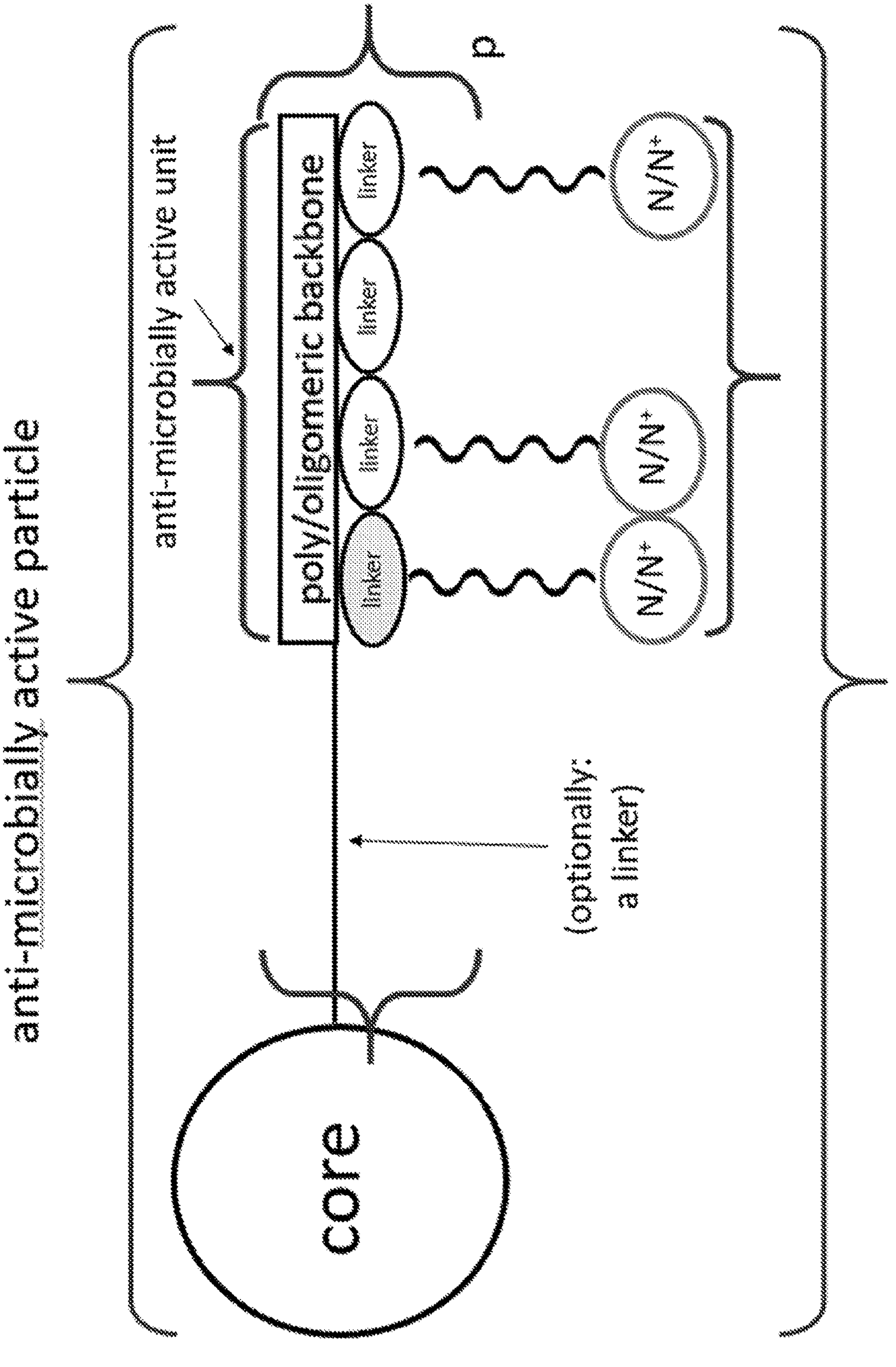
FIGS. 1A-1C depict anti-microbial active particle scheme.

It will be appreciated that for simplicity and clarity of illustration, elements shown in the Figures have not necessarily been drawn to scale. For example, the dimensions of some of the elements may be exaggerated relative to other elements for clarity. Further, where considered appropriate, reference numerals may be repeated among the Figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that this invention may be practiced without these specific details. In other instances, well-known methods, procedures, and components have not been described in detail so as not to obscure this invention.

Anti-Microbial Coatings and Substrates Coated with the Same

In one aspect, this invention provides a coating comprising anti-microbial particles and a matrix.

In one additional aspect, this invention provides a coated substrate, comprising matrix, anti-microbial particles and substrate. In one embodiment, the matrix comprises a matrix material and the substrate comprises a substrate material. In one embodiment, the matrix material and substrate material are the same. In one embodiment, the matrix material and substrate material are different. In another embodiment, the anti-microbial particles are embedded within the matrix. Each possibility represents a separate embodiment of this invention.

In some embodiments, anti-microbial particles are described in further detail hereinbelow. In one embodiment, the anti-microbial particles are represented by structure (1). In one embodiment, the anti-microbial particles are represented by formula (I). In one embodiment, the anti-microbial particles are a mixture of different particles (having different structures, e.g. one of structure (1) and one of structure (I); see below particles section for details). Each possibility represents a separate embodiment of this invention.

In some embodiments, the substrate material and the matrix material are each independently selected from organic (e.g. thermoplastic or thermoset) or inorganic polymers. In another embodiment, the organic polymers are selected from the following non-limiting list: hydrogels, polyolefins such as polyvinylchloride (PVC), polyacrylonitrile (PAN), polyvinylidene fluoride (PVDF), polyethylene, polystyrene, polyacrylonitrile-butadiene-styrene (ABS), and polypropylene, epoxy resins, acrylate resins such as poly methyl methacrylate, polyurethane or any combination thereof. In another embodiment, the inorganic polymers are selected from the following non-limiting list:

silicone polymers such as polydimethylsiloxane (PDMS), ceramics, metals or any combination thereof. In another embodiment, the hydrogel is poloxamer or alginate. In another embodiment, the commercial poloxamer is used or it is formed by a reaction between a polymer and other reagent. In another embodiment, the polymer is poly(ethylene glycol) (PEG) with reactive end groups (such as epoxides in PEG-diglycidyl ether or diglycidyl ether of bisphenol A (DGEBA)) and the reagent has multiple reactive sites (e.g. diethylenetriamine or polypropylene glycol-polyethylene glycol-polypropylene glycol (PPG-PEG-PPG) diamine). In another embodiment, another polymer material to be used in the context of this invention is resins used in dental, surgical, chirurgical and orthopedic composite materials. In such applications, anti-microbial particles could be first dispersed within the resin part or added simultaneously with filler or any other solid ingredients (if any). Most of these resins are acrylic or epoxy type monomers that undergo polymerization in-vivo. Each possibility represents a separate embodiment of this invention.

In some embodiments, the weight ratio of the particles to the whole coating (comprising matrix and particles) is between 0.25 and 10%. In another embodiment, the weight ratio is between 0.5 and 2%. In another embodiment, the weight ratio is between 1 and 5%. In another embodiment, the weight ratio is between 5 and 10%. Each possibility represents a separate embodiment of this invention.

In some embodiments, the particles interact weakly or physically (mechanically) with the matrix. In another embodiment, the anti-microbial particles are mechanically embedded within the matrix. In another embodiment, these particles are three dimensionally "locked" between the molecular/polymeric/oligomeric chains of the matrix material, preventing them from migrating out from the complex network. In another embodiment, the strong hydrophobic nature of these particles also plays a role in preventing the particles from moving into the hydrophilic surrounds such as in the case of physiological, dental, orthopedic or other medical applications. In another embodiment, the matrix (and material thereof) is inert to the particles and does not react with them. In one embodiment, the particles comprise functional groups, capable of reacting with molecular moieties of the matrix material. In another embodiment, the particles interact chemically with the matrix (and material thereof). Each possibility represents a separate embodiment of this invention.

In some embodiments, the coating further comprises at least one pharmaceutically active ingredient. In another embodiment, non-limiting examples of pharmaceutically active ingredients include Analgesics, Antibiotics, Anticoagulants, Antidepressants, Anticancers, Antiepileptics, Antipsychotics, Antivirals, Sedatives and Antidiabetics. In another embodiment, non-limiting examples of Analgesics include paracetamol, non-steroidal anti-inflammatory drugs (NSAIDs), morphine and oxycodone. In another embodiment, non-limiting examples of Antibiotics include penicillin, cephalosporin, ciprofolxacin and erythromycin. In another embodiment, non-limiting examples of Anticoagulants include warfarin, dabigatran, apixaban and rivaroxaban. In another embodiment, non-limiting examples of Antidepressants include sertraline, fluoxetine, citalopram and paroxetine. In another embodiment, non-limiting examples of Anticancers include Capecitabine, Mitomycin, Etoposide and Pembrolizumab. In another embodiment, non-limiting examples of Antiepileptics include Acetazolamide, Clobazam, Ethosuximide and lacosamide. In another embodiment, non-limiting examples of Antipsychotics include Risperidone, Ziprasidone, Paliperidone and Lurasidone. In another embodiment, non-limiting examples of Antivirals include amantadine, rimantadine, oseltamivir and zanamivir. In another embodiment, non-limiting examples of Sedatives include Alprazolam, Clorazepate, Diazepam and Estazolam. In another embodiment, non-limiting examples of Antidiabetics include glimepiride, gliclazide, glyburide and glipizide. Each possibility represents a separate embodiment of this invention.

In some embodiments, the coating further comprises excipients. In another embodiment, the excipient comprises binders, coatings, lubricants, flavors, preservatives, sweeteners, vehicles and disintegrants. In another embodiment, non-limiting examples of binders include saccharides, gelatin, polyvinylpyrolidone (PVP) and polyethylene glycol (PEG). In another embodiment, non-limiting examples of coatings include hydroxypropylmethylcellulose, polysaccharides and gelatin. In another embodiment, non-limiting examples of lubricants include talc, stearin, silica and magnesium stearate. In another embodiment, non-limiting examples of disintegrants include crosslinked polyvinylpyrolidone, crosslinked sodium carboxymethyl cellulose (croscarmellose sodium) and modified starch sodium starch glycolate. Each possibility represents a separate embodiment of this invention.

In some embodiments, non-limiting shapes of the substrates include thick or thin films, surfaces, pallets, tubes and artificial or replacement joints. Each possibility represents a separate embodiment of this invention.

In some embodiments, the thickness of the coating ranges between 5 nm and 1000 nm. In another embodiment, the thickness is between 10 and 50 nm. In another embodiment, the thickness is between 10 and 50 nm. In another embodiment, the thickness is between 50 and 100 nm. In another embodiment, the thickness is between 100 and 500 nm. In another embodiment, the thickness is between 500 and 1000 nm. Each possibility represents a separate embodiment of this invention.

In some embodiments, the substrate is completely covered with the coating. In one embodiment, the substrate is partially covered with the coating, i.e. for example in a pallet having two sides, only one side is covered with the coating; or one side is covered not completely. In one embodiment, if the substrate has outer and inner surfaces—both surfaces or only one of them are covered with the coating. Each possibility represents a separate embodiment of this invention.

In some embodiments, the substrate (before or after coating) is smooth or rough. In one embodiment, the substrate has a solid uniform morphology with low porosity or a porous morphology having pore size diameter of between about 1 to about 30 nm. In another embodiment, the substrate is pre-treated before coating to afford a specific morphology of the bulk and/or surface. In another embodiment, the substrate is pre-treated to afford chemical functionalization (e.g. HO- or H-termination) of the surface thereof. Each possibility represents a separate embodiment of this invention.

Processes of Preparing the Substrates

In one further aspect, this invention provides processes of preparing the coated substrates as described hereinabove. In one embodiment, the coated substrate comprises anti-microbial particles as described hereinbelow and a matrix as described hereinabove.

In one embodiment, this invention is directed to a process of preparing a coated substrate having an anti-microbial coating, wherein the coating comprises anti-microbial particles and a matrix; and the process comprises:

dissolving anti-microbial particles and a matrix material in a solvent to form a solution; and coating a substrate with the solution to provide a substrate having an anti-microbial coating.

In another embodiment, the coating is performed by:

a. dipping a substrate into the solution followed by solvent elimination;

b. spraying the solution onto a substrate, followed by solvent elimination;

c. spin coating a substrate with the solution, followed by solvent elimination;

d. brushing a substrate with the solution, followed by solvent elimination;

e. spreading the solution on a substrate, followed by solvent elimination; or f. by abrasive blasting.

"Abrasive blasting", (more commonly known as sandblasting) refers herein to the operation of forcibly propelling a stream of abrasive material (the coating of this invention) against a surface under high air (or any gas) pressure (to smooth a rough surface, roughen a smooth surface), shape a surface or remove surface contaminants. Using this method the particles are forced and embedded into the surface and stay there for a long period of time.

In one embodiment, the substrate before the coating is a tube. In another embodiment, a tube having anti-microbial particles is prepared by the following process:

dissolving anti-microbial particles and a matrix material in a solvent to form a solution; and dipping a tube while ensuring penetration of the solution into all of the tube walls followed by solvent elimination to provide a tube having an anti-microbial coating.

In another embodiment, a tube having anti-microbial particles is prepared by the following process:

dissolving anti-microbial particles and a matrix material in a solvent to form a solution;

dipping a tube into the solution followed by solvent elimination;

injecting the solution into the inner part of the tube; and washing the inner part of the tube with the solvent followed by solvent elimination to provide a tube having an anti-microbial coating.

In one embodiment, this invention is directed to a process of preparing a substrate having an anti-microbial coating, wherein the coating comprises anti-microbial particles and a matrix; and the process comprises:

dissolving anti-microbial particles and a monomer, oligomer or a pre-polymerized substance that can undergo polymerization, cross linking and/or vulcanization in a solvent to form a solution;

coating a substrate with the solution; and polymerizing, cross linking and/or vulcanizing the substrate coated with the solution to provide a substrate having an anti-microbial coating.

In another embodiment, the coating is performed by:

a. dipping a substrate into the solution followed by solvent elimination;

b. spraying the solution onto a substrate, followed by solvent elimination;

c. spin coating a substrate with the solution, followed by solvent elimination;

d. brushing a substrate with the solution, followed by solvent elimination;

e. spreading the solution on a substrate, followed by solvent elimination; or f. by abrasive blasting.

In another embodiment, non limiting examples of monomers, oligomers or a pre-polymerized substances that can undergo polymerization, cross linking and/or vulcanization include: epoxy-amine blend, acrylic/methacrylic resin blend with photo/chemical polymerization initiators and silicone based polymers/monomers/oligomers that undergo curing. In another embodiment, polymerizing, cross linking and/or vulcanizing is performed via chemical reagents such as initiators, cross-linkers and/or via curing done with lamps or via exposure of the pre-polymerized substance to ambient light and/or air.

In one embodiment, this invention is directed to a process of preparing a substrate having an anti-microbial coating, wherein the coating comprises anti-microbial particles and a matrix; and the process comprises:

pouring a dry anti-microbial composition onto a substrate;

melting the dry composition by heat; and cooling the melt to provide a substrate having an anti-microbial coating;

wherein said dry anti-microbial composition comprises anti-microbial particles and a matrix.

In another embodiment, melting is done via extrusion. In another embodiment, the extrusion is a compounding extrusion, i.e. where additives are added to the components to be extruded. In another embodiment, the anti-microbial particles are embedded within the matrix. In another embodiment, the matrix comprises a matrix material and the matrix material is described hereinabove.

In one embodiment, this invention is directed to a process of preparing a substrate having an anti-microbial coating, wherein the coating comprises anti-microbial particles and a matrix; and the process comprises:

pouring a dry matrix composition onto a substrate;

melting the poured dry matrix composition by heat;

pouring dry anti-microbial particles into the melt to provide a mixture of a melted dry matrix composition and anti-microbial particles; and cooling the mixture to provide a substrate having an anti-microbial coating;

wherein said dry matrix composition comprises a matrix.

In another embodiment, melting is done via extrusion. In another embodiment, the extrusion is a compounding extrusion, i.e. where additives are added to the components to be extruded. In another embodiment, the anti-microbial particles are embedded within the matrix of the provided coated substrate. In another embodiment, the matrix is comprises a matrix material and the matrix material is described hereinabove.

In some embodiments, solvent elimination done within the processes of this invention is accomplished via vacuum, heat, removing by another liquid, distillation or any combination thereof. In one embodiment, the solvent is eliminated by vacuum and heat. Each possibility represents a separate embodiment of this invention.

In some embodiments, the anti-microbial particles within the processes of this invention are as described hereinbelow; and the matrix materials and the substrates within the processes are as described hereinabove. Each possibility represents a separate embodiment of this invention.

In another embodiment, the process of coating a substrate is being repeated more than once. In another embodiment, the process of coating a substrate is repeated two, three, four, five times or more.

In one embodiment, coated substrates are prepared according to any one of the processes as described hereinabove.

Anti-Microbial Particles

In one embodiment, this invention is directed to anti-microbial particles, wherein the particles comprise:

(i) an inorganic or organic core; and (ii) an anti-microbial active unit chemically bound to the core;

wherein the anti-microbial active unit is connected directly (via a bond) or indirectly (via a third linker) to the core;

wherein the anti-microbial active unit comprises a monomeric unit comprising an anti-microbial active group; and wherein the number of the anti-microbial active groups per each anti-microbial active unit is between 1-200.

In some embodiments, the anti-microbial particles comprise (i) an inorganic or organic core; and (ii) an anti-microbial active part chemically bound to the core. In one embodiment, the anti-microbial active part comprises one monomeric unit. In one embodiment, the anti-microbial active part comprises more than one monomeric unit. In another embodiment, the anti-microbial active part with the more than one monomeric unit comprises more than one linker. In another embodiment, the anti-microbial active unit has between 2-200 monomeric units. In another embodiment, the anti-microbial active unit has between 2-5 monomeric units. In another embodiment, the anti-microbial active unit has between 5-10 monomeric units. In another embodiment, the anti-microbial active unit has between 10-20 monomeric units. In another embodiment, the anti-microbial active unit has between 20-50 monomeric units. In another embodiment, the anti-microbial active unit has between 50-100 monomeric units. In another embodiment, the anti-microbial active unit has between 100-200 monomeric units.

Figure 1B:
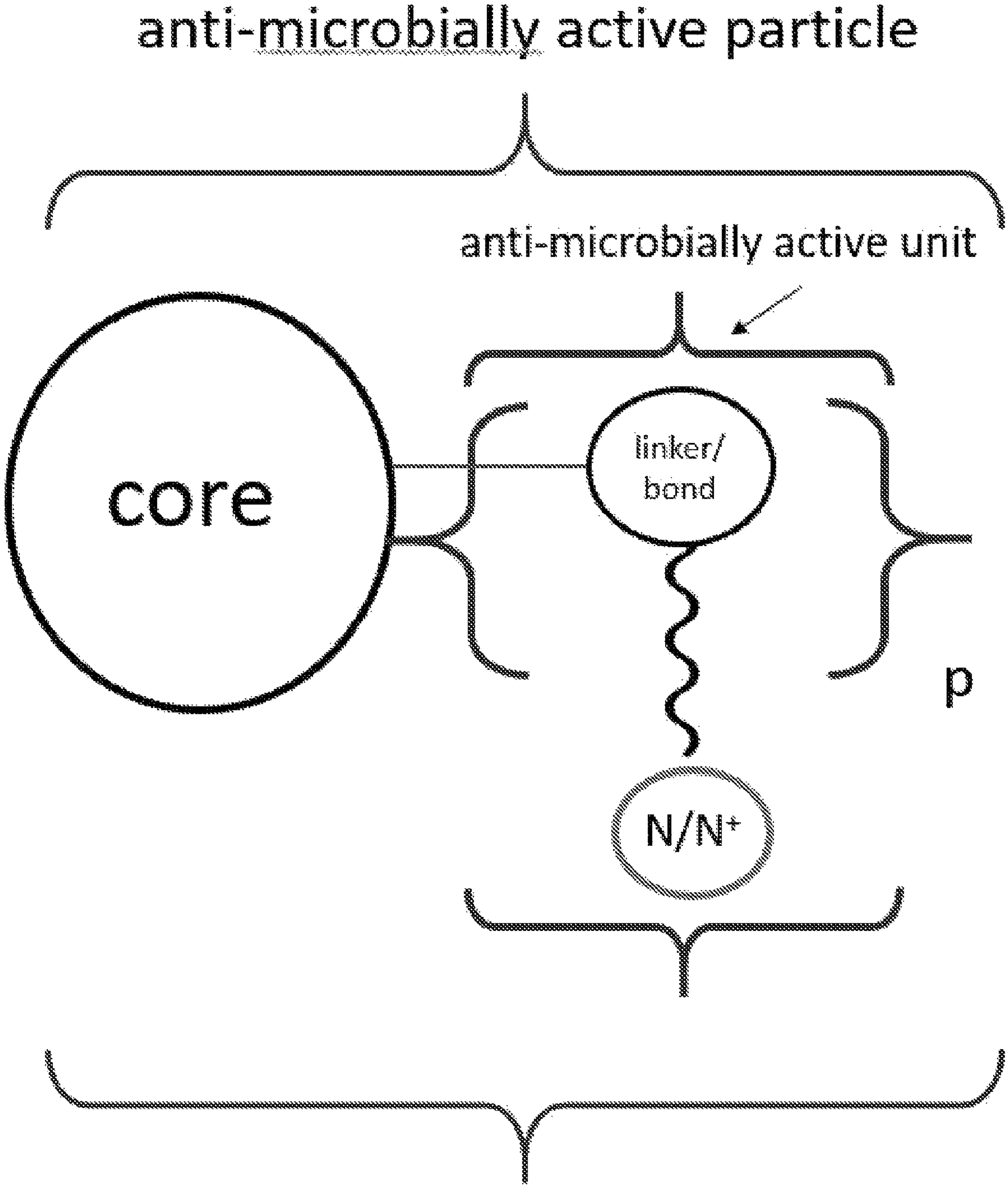
Figure 1C:
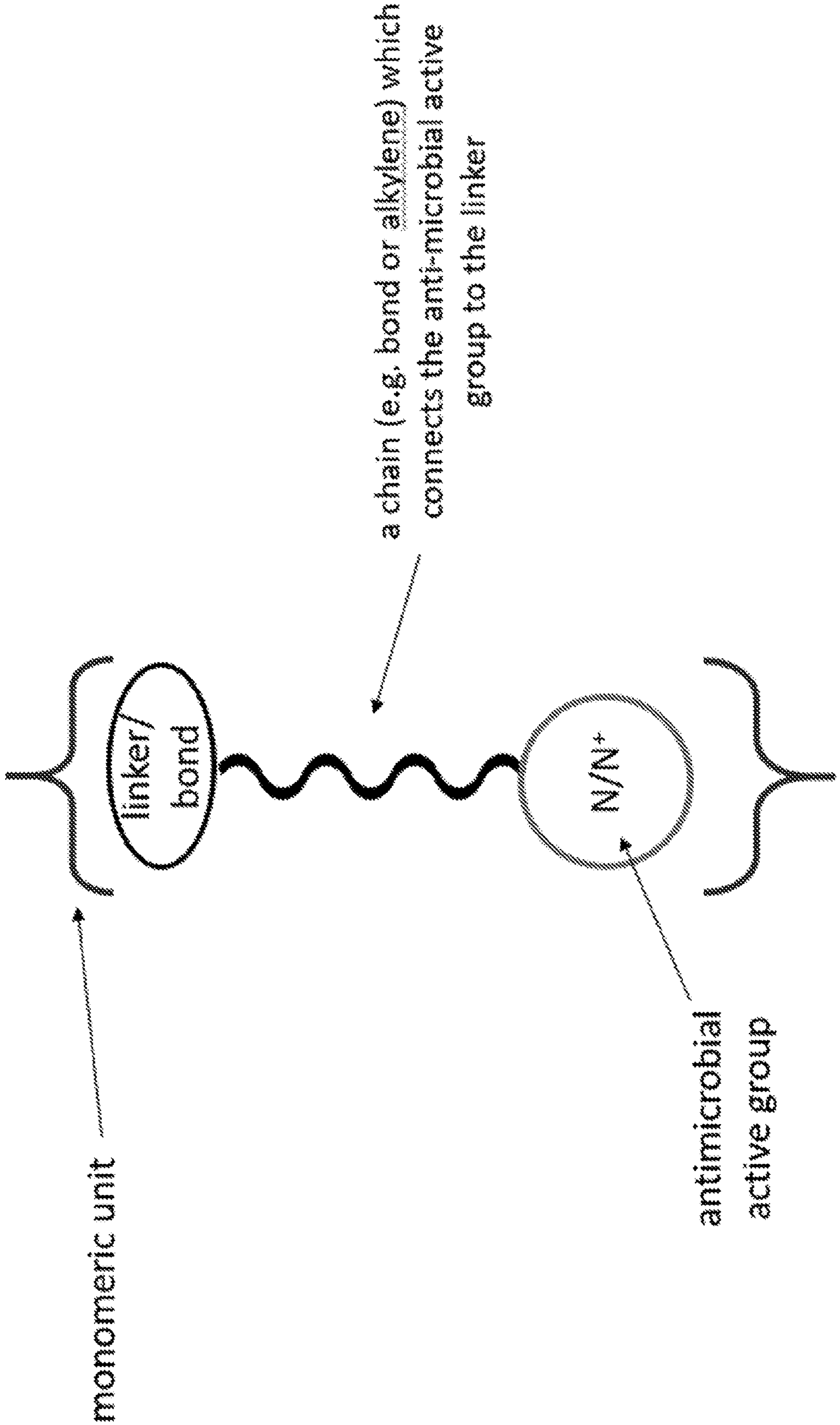

In one embodiment, the anti-microbial active unit comprises more than one monomeric unit. In another embodiment, the monomeric units are connected to each other via a first linker, a second linker or both. In another embodiment, each monomeric unit comprises an anti-microbial active group. In another embodiment, an anti-microbial active unit comprises at least one anti-microbial active group. In another embodiment, an anti-microbial active unit comprises at least two anti-microbial active groups. In another embodiment, FIGS. 1A, 1B and 1C illustrate schematically the anti-microbial active particles of this invention (FIG. 1A: more than one monomer; FIG. 1B: one monomeric unit and FIG. 1C: detailed scheme of one monomer).

In some embodiment, the anti-microbial particles are presented by structure (1):

(1)

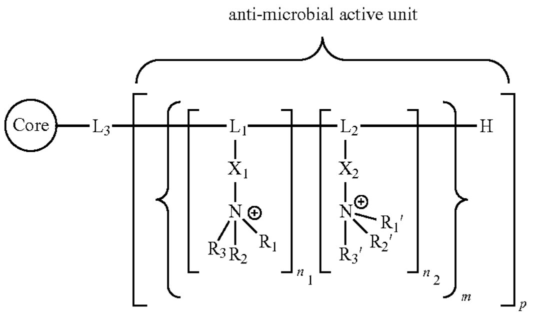

wherein the core is an organic polymer or an inorganic material;

$L_1$ is a first linker or a bond;

$L_2$ is a second linker;

$L_3$ is a third linker or a bond;

$R_1$ and $R_1'$ are each independently alkyl, terpenoid, cycloalkyl, aryl, heterocycle, alkenyl, alkynyl or any combination thereof;

$R_2$ and $R_2'$ are each independently alkyl, terpenoid, cycloalkyl, aryl, heterocycle, alkenyl, alkynyl or any combination thereof;

$R_3$ and $R_3'$ are each independently nothing, hydrogen, alkyl, terpenoid moiety, cycloalkyl, aryl, heterocycle, a conjugated alkyl, alkenyl, alkynyl or any combination thereof; wherein if $R_3$ or $R_3'$ are nothing, the nitrogen is not charged;

$X_1$ and $X_2$ is each independently a bond, alkylene, alkenylene, or alkynylene;

p defines the number of anti-microbial active units per one sq nm ($nm^2$) of the core surface, wherein said density is of between 0.01-30 anti-microbial units per one sq nm ($nm^2$) of the core surface of the particle;

$n_1$ is each independently an integer between 0 to 200;

$n_2$ is each independently an integer between 0 to 200;

wherein $n_1+n_2 \geq 1$; and m is an integer between 1 to 200 and the repeating unit is the same or different.

In some embodiments, the anti-microbial particles are represented by structure (2):

(2)

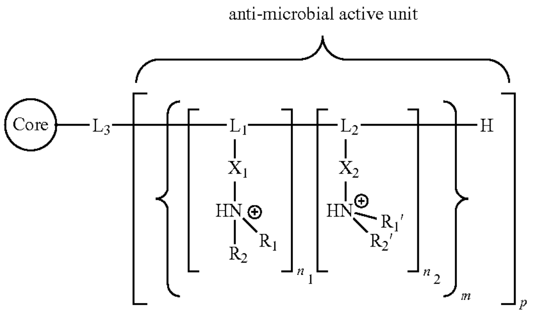

wherein the core is an organic polymer or an inorganic material;

$L_1$ is a first linker or a bond;

$L_2$ is a second linker;

$L_3$ is a third linker or a bond;

$R_1$ and $R_1'$ are each independently alkyl, terpenoid, cycloalkyl, aryl, heterocycle, alkenyl, alkynyl or any combination thereof;

$R_2$ and $R_2'$ are each independently alkyl, terpenoid, cycloalkyl, aryl, heterocycle, alkenyl, alkynyl or any combination thereof;

$X_1$ and $X_2$ is each independently a bond, alkylene, alkenylene, or alkynylene;

p defines the number of anti-microbial active units per one sq nm ($nm^2$) of the core surface, wherein said density is of between 0.01-30 anti-microbial units per one sq nm ($nm^2$) of the core surface of the particle;

$n_1$ is each independently an integer between 0 to 200;

$n_2$ is each independently an integer between 0 to 200;

wherein $n_1+n_2 \geq 1$;

m is an integer between 1 to 200 and the repeating unit is the same or different.

In another embodiment, the number of the anti-microbial active groups per each anti-microbial active part is at least two, i.e. $n_1+n_2 \geq 2$ and $m \geq 1$. In another embodiment, the number of the anti-microbial active groups per each anti-microbial active part is one, i.e. $n_1+n_2=1$ and $m=1$.

In some embodiments, the anti-microbial particles are represented by structure (3):

(3)

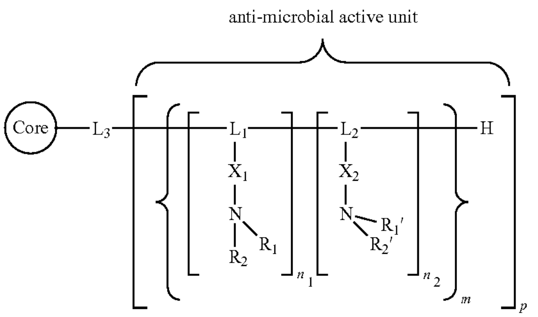

wherein the core is an organic polymer or an inorganic material;

$L_1$ is a first linker or a bond;

$L_2$ is a second linker;

$L_3$ is a third linker or a bond;

$R_1$ and $R_1'$ are each independently alkyl, terpenoid, cycloalkyl, aryl, heterocycle, alkenyl, alkynyl or any combination thereof;

$R_2$ and $R_2'$ are each independently alkyl, terpenoid, cycloalkyl, aryl, heterocycle, alkenyl, alkynyl or any combination thereof;

$X_1$ and $X_2$ is each independently a bond, alkylene, alkenylene, or alkynylene;

p defines the number of anti-microbial active units per one sq nm ($nm^2$) of the core surface, wherein said density is of between 0.01-30 anti-microbial units per one sq nm ($nm^2$) of the core surface of the particle;

$n_1$ is each independently an integer between 0 to 200;

$n_2$ is each independently an integer between 0 to 200;

wherein $n_1+n_2 \geq 1$;

m is an integer between 1 to 200 and the repeating unit is the same or different.

In another embodiment, the number of the anti-microbial active groups per each anti-microbial active part is at least two, i.e. $n_1+n_2 \geq 2$ and $m \geq 1$. In another embodiment, the number of the anti-microbial active groups per each anti-microbial active part is one, i.e. $n_1+n_2=1$ and $m=1$.

In another embodiment, the particles of structures (1) to (3) comprise one monomeric unit per one anti-microbial active unit. In another embodiment, the particles of structures (1) to (3) comprise more than one anti-microbial active group per one anti-microbial active unit.

In some embodiments, the anti-microbial particles are represented by structure (4):

(4)

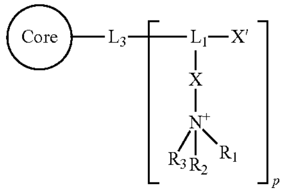

wherein the core is an organic polymer or an inorganic material;

$L_1$ is a first linker or a bond;

$L_3$ is a third linker or a bond;

$R_1$ is alkyl, terpenoid, cycloalkyl, aryl, heterocycle, alkenyl, alkynyl or any combination thereof;

$R_2$ is alkyl, terpenoid, cycloalkyl, aryl, heterocycle, alkenyl, alkynyl or any combination thereof;

$R_3$ is nothing, hydrogen, alkyl, terpenoid moiety, cycloalkyl, aryl, heterocycle, alkenyl, alkynyl or any combination thereof; wherein if $R_3$ or $R_3'$ are nothing, the nitrogen is not charged;

X is a bond, alkyl, alkenyl, or alkynyl;

X' is nothing or hydrogen; and p defines the number of anti-microbial active units per one sq nm ($nm^2$) of the core surface, wherein said density is of between 0.01-30 anti-microbial units per one sq nm ($nm^2$) of the core surface of the particle;

wherein if $L_1$ and X are bonds, then the nitrogen is part of the core;

wherein at least one of $R_1$, $R_2$, $R_3$ is hydrophobic.

In some embodiments, the anti-microbial particles are represented by structure (5):

(5)

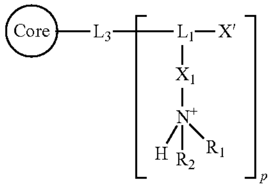

wherein the core is an organic polymeric material or an inorganic material;

$L_1$ is a first linker or a bond;

$L_3$ is a third linker or a bond;

$R_1$ is alkyl, terpenoid, cycloalkyl, aryl, heterocycle, alkenyl, alkynyl or any combination thereof;

$R_2$ is alkyl, terpenoid, cycloalkyl, aryl, heterocycle, alkenyl, alkynyl or any combination thereof;

X is a bond, alkyl, alkenyl or alkynyl;

X' is nothing or hydrogen; and p defines the number of anti-microbial active units per one sq nm ($nm^2$) of the core surface, wherein said density is of between 0.01-30 anti-microbial units per one sq nm ($nm^2$) of the core surface of the particle;

wherein if $L_1$ and X are bonds, then the nitrogen is an integral part of the core;

wherein at least one of $R_1$, $R_2$ is hydrophobic.

In some embodiments, the anti-microbial particles are represented by structure (6):

(6)

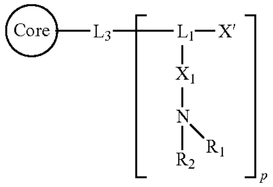

wherein the core is an organic polymeric material or an inorganic material;

$L_1$ is a first linker or a bond;

$L_3$ is a third linker or a bond;

$R_1$ is alkyl, terpenoid, cycloalkyl, aryl, heterocycle, alkenyl, alkynyl or any combination thereof;

$R_2$ is alkyl, terpenoid, cycloalkyl, aryl, heterocycle, alkenyl, alkynyl or any combination thereof;

X is a bond, alkyl, alkenyl, or alkynyl;

X' is nothing or hydrogen; and p defines the number of anti-microbial active units per one sq nm ($nm^2$) of the core surface, wherein said density is of between 0.01-30 anti-microbial units per one sq nm ($nm^2$) of the core surface of the particle;

wherein if $L_1$ and X are bonds, then the nitrogen is an integral part of the core;

wherein at least one of $R_1$, $R_2$ is hydrophobic.

Specific examples of anti-microbial particles of this invention include:

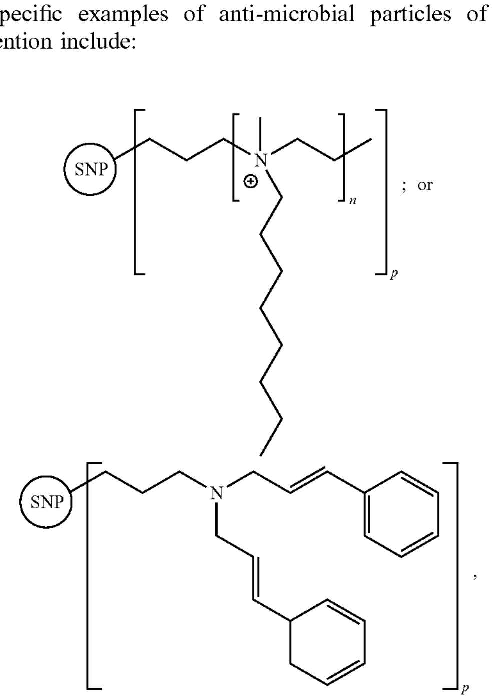

; or , where n=1-200; "SNP" refers to the a silica core of the particles of this invention; and p defines the number of anti-microbial active units per one sq nm ($nm^2$) of the core surface, wherein said density is of between 0.01-30 anti-microbial units per one sq nm ($nm^2$) of the core surface of the particle. In another embodiment, n=1-3. In another embodiment, n=3-20. In another embodiment, n=20-50. In another embodiment, n=50-100. In another embodiment, n=100-200.

In some embodiments, the term "anti-microbial active group" and the term "monomeric anti-microbial active group" refer to the same and comprise a protonated tertiary amine, a tertiary amine or a quaternary ammonium, as represented by the following formulas:

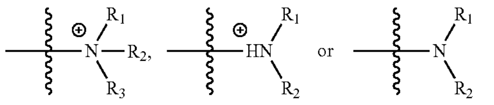

or wherein:

$R_1$ is alkyl, terpenoid, cycloalkyl, aryl, heterocycle, alkenyl, alkynyl or any combination thereof;

$R_2$ is alkyl, terpenoid, cycloalkyl, aryl, heterocycle, alkenyl, alkynyl or any combination thereof;

$R_3$ is nothing, hydrogen, alkyl, terpenoid moiety, cycloalkyl, aryl, heterocycle, alkenyl, alkynyl or any combination thereof; wherein if $R_3$ or $R_3'$ are nothing, the nitrogen is not charged.

In another embodiment, at least one of $R_1$, $R_2$ or $R_3$ is hydrophobic.

In another embodiment, the number of the anti-microbial active groups per each anti-microbial active unit is at least two, i.e. $n_1+n_2\geq 2$ and $m\geq 1$. In another embodiment, the number of the anti-microbial active groups per each anti-microbial active unit is one, i.e. $n_1+n_2=1$ and $m=1$.

In another embodiment, the particles of structures (4) to (6) comprise one monomeric unit per one anti-microbial active unit. In another embodiment, the particles of structures (1) to (3) comprise one or more than one anti-microbial active group per one anti-microbial active unit.

In another embodiment, the particle of structures (1) to (6) has an inorganic core. In another embodiment, the particle of structure (1) to (6) has an organic core. In another embodiment, the organic core is a polymeric organic core. In another embodiment, the core is inert. In one embodiment, the particles of this invention represented by structures (1)-(3) comprise an anti-microbial active group of $-^{+}N(R_1)(R_2)(R_3)$, $-^{+}NH(R_1)(R_2)$, $-N(R_1)(R_2)-^{+}N(R_1')(R_2')(R_3')$, $-^{+}NH(R_1')(R_2')$ or $-N(R_1')(R_2')$. In one embodiment $R_1$ and/or $R_1'$, $R_2$ and/or $R_2'$ and $R_3$ and/or $R_3'$ are the same or different and are independently alkyl, terpenoid, cycloalkyl, aryl, heterocycle, alkenyl, alkynyl or any combination thereof. In another embodiment, $R_1$, $R_2$ and $R_3$ are independently an alkyl. In another embodiment, $R_1$ and/or $R_1'$, $R_2$ and/or $R_2'$ and $R_3$ and/or $R_3'$ are independently a terpenoid. In another embodiment, $R_1$ and/or $R_1'$, $R_2$ and/or $R_2'$ and $R_3$ and/or $R_3'$ are independently a cycloalkyl. In another embodiment, $R_1$ and/or $R_1'$, $R_2$ and/or $R_2'$ and $R_3$ and/or $R_3'$ are independently an aryl. In another embodiment, $R_1$ and/or $R_1'$, $R_2$ and/or $R_2'$ and $R_3$ and/or $R_3'$ are independently a heterocycle. In another embodiment, $R_1$ and/or $R_1'$, $R_2$ and/or $R_2'$ and $R_3$ and/or $R_3'$ are independently an alkenyl. In another embodiment, $R_1$ and/or $R_1'$, $R_2$ and/or $R_2'$ and $R_3$ and/or $R_3'$ are independently an alkynyl. In another embodiment, $R_3$ is nothing. In another embodiment, $R_3$ and/or $R_3'$ is hydrogen. In another embodiment at least one of $R_1$ and/or $R_1'$, $R_2$ and/or $R_2'$ and $R_3$ and/or $R_3'$ is hydrophobic alkyl, terpenoid, cycloalkyl, aryl, heterocycle, alkenyl, alkynyl or any combination thereof. Each represents a separate embodiment of this invention.

In another embodiment $R_1$ and $R_1'$ are the same. In another embodiment $R_2$ and $R_2'$ are the same. In another embodiment $R_3$ and $R_3'$ are the same. In another embodiment $R_1$ and $R_1'$ are different. In another embodiment $R_2$ and $R_2'$ are different. In another embodiment $R_3$ and $R_3'$ are different.

In one embodiment, at least one of $R_1$, $R_2$ and $R_3$ and/or at least one of $R_1'$, $R_2'$ and $R_3'$ of structure (1) is hydrophobic. In one embodiment, at least one of $R_1$ and $R_2$ and/or at least one of $R_1'$ and $R_2'$ of structures (2) and (3) is hydrophobic.

The term "hydrophobic" refers to an alkyl, alkenyl or alkynyl having at least four carbons, or the term hydrophobic refers to terpenoid, to cycloalkyl, aryl or heterocycle having at least six carbons. Each possibility represents a separate embodiment of this invention In one embodiment, at least one of $R_1$, $R_2$ and $R_3$ and/or at least one of $R_1'$, $R_2'$ and $R_3'$ of structure (1) is a $C_4$-$C_{24}$ alkyl, $C_4$-$C_{24}$ alkenyl, $C_4$-$C_{24}$ alkynyl or a terpenoid. In one embodiment, at least one of $R_1$ and $R_2$ and/or at least one of $R_1'$ and $R_2'$ of structures (2) and (3) is a $C_4$-$C_{24}$ alkyl, $C_4$-$C_{24}$ alkenyl, $C_4$-$C_{24}$ alkynyl or a terpenoid. Each possibility represents a separate embodiment of this invention.

In one embodiment, at least one of $R_1$, $R_2$ and $R_3$ and/or at least one of $R_1'$, $R_2'$ and $R_3'$ of structure (1) is a $C_4$-$C_8$ alkyl, $C_4$-$C_8$ alkenyl, $C_4$-$C_8$ alkynyl or a terpenoid. In one embodiment, at least one of $R_1$ and $R_2$ and/or at least one of $R_1'$ and $R_2'$ of structures (2) and (3) is a $C_4$-$C_8$ alkyl, $C_4$-$C_8$ alkenyl, $C_4$-$C_8$ alkynyl or a terpenoid. Each possibility represents a separate embodiment of this invention.

In one embodiment, $R_1$ and/or $R_1'$ of structures (1) to (6) is a terpenoid. In another embodiment, $R_1$ and/or $R_1'$ is a terpenoid and $R_2$ and/or $R_2'$ is a $C_1$-$C_4$ alkyl. In another embodiment, the core is an organic polymeric core, $R_3$ and/or $R_3$' is nothing and $R_1$ and/or $R_1$' is a terpenoid. In another embodiment, the core is an organic polymeric core, $R_3$ and/or $R_3$' is a hydrogen and $R_1$ and/or $R_1$' is a terpenoid. In another embodiment, the core is an inorganic core, $R_3$ and/or $R_3$' is nothing and $R_1$ and/or $R_1$' is a terpenoid. In another embodiment, the core is an inorganic core, $R_3$ and/or $R_3$' is a hydrogen and $R_1$ and/or $R_1$' is a terpenoid. In another embodiment, the core is an inorganic core, $R_3$ and/or $R_3$' is a $C_1$-$C_{24}$ alkyl, terpenoid, cycloalkyl, aryl, heterocycle, a conjugated $C_1$-$C_{24}$ alkyl, $C_1$-$C_{24}$ alkenyl, $C_1$-$C_{24}$ alkynyl or any combination thereof and $R_1$ and/or $R_1$' is a terpenoid.

In one embodiment, the particles of this invention comprise an anti-microbial active unit and an inert core, wherein the anti-microbial active unit and the core are linked indirectly.

In some embodiments $L_1$, $L_2$ or $L_3$ is each independently the same or a different linker. In some embodiments, $L_1$, $L_2$ and $L_3$ are connected to each other, in any possible way. In some embodiment, $L_3$ is nothing and $L_1$ or $L_2$ is connected to the core covalently. In another embodiment, $L_3$ is connected to the core covalently and $L_1$ or $L_2$ is connected to $L_3$. In another embodiment, $L_1$ is connected to X, X' and $L_3$ or core. In another embodiment, a "linker" comprises any possible chemical moiety capable of connecting at least two other chemical moieties which are adjacent to such linker. In another embodiment, the monomeric unit of the anti-microbial active unit comprises a first and/or second linker/s ($L_1$ or $L_2$) and an anti-microbial group. In another embodiment, $L_1$ and/or $L_2$ are/is the backbone of the anti-microbial active unit.

In some embodiments, the linker comprises a functional group. In another embodiment, the linker comprises two (same or different) functional groups. In another embodiment, the functional group comprises phosphate, phosphonate, siloxane, silane, ether acetal, amide, amine, anhydride, ester, ketone, or aromatic ring or rings functionalized with any of the preceding moieties. Each possibility represents a separate embodiment of this invention.

In another embodiment, $L_1$ or $L_2$ is a C1 to C18 alkylene, alkenylene, alkynylene or aryl substituted with at least one carboxyl moiety, wherein the carboxyl end is attached to the core. This linker may be derived from a C1 to C18 alkylene substituted with at least one carboxyl moiety and having an amino end which is modified to anti-microbial active group [—$^+N(R_1)(R_2)(R_3)$, —$^+NH(R_1)(R_2)$, —$N(R_1)(R_2)$—$^+N(R_1')(R_2')(R_3')$, —$^+NH(R_1')(R_2')$ or —$N(R_1')(R_2')$ (defined in structures (1) to (6))]. This linker may be derived from an amino acid of natural or synthetic source having a chain length of between 2 and 18 carbon atoms (polypeptide), or an acyl halide of said amino acid. Non-limiting examples for such amino acids are 18-amino octadecanoic acid and 18-amino stearic acid. In another embodiment, $L_1$ or $L_2$ is a C1 to C18 alkylene substituted with at least one amine or amide moiety.

In another embodiment, $L_1$, $L_2$, $L_3$ or any combination thereof is a C1 to C18 alkylene, alkenylene, alkynylene or aryl. This linker may be derived from a di-halo alkylene, which is functionalized at each end with the core and anti-microbial active group, respectively, by replacement of the halogen moiety to a functional group that binds to the core and replacement of the halogen moiety to obtain [—$^+N(R_1)(R_2)(R_3)$, —$^+NH(R_1)(R_2)$, —$N(R_1)(R_2)$—$^+N(R_1')(R_2')(R_3')$, —$^+NH(R_1')(R_2')$ or —$N(R_1')(R_2')$ (defined in structures (1) to (6))]

In another embodiment, $L_1$, $L_2$, $L_3$ or any combination thereof is an aromatic group derived from non-limiting examples of 4,4-biphenol, dibenzoic acid, dibenzoic halides, dibenzoic sulphonates, terephthalic acid, terephthalic halides, and terephthalic sulphonates. This linker is functionalized with the core and anti-microbial active group, respectively, through the functional group thereof (i.e., hydroxyl, carboxy or sulfonate). In another embodiment, this linker is directly attached to the core at one end or indirectly, via a third linker ($L_3$) and is modified at the other end to anti-microbial active group [—$^+N(R_1)(R_2)(R_3)$, —$^+NH(R_1)(R_2)$, —$N(R_1)(R_2)$—$^+N(R_1')(R_2')(R_3')$, —$^+NH(R_1')(R_2')$ or —$N(R_1')(R_2')$ (defined in structures (1) to (6))].

In another embodiment, $L_1$, $L_2$, $L_3$ or any combination thereof, is a siloxane or silane group derived and/or selected from non-limiting examples of trialkoxyalkylsilane, trialkoxyarylsilane, trihaloalkylsilane, trihaloarylsilane, 3-aminopropyltriethoxysilane (APTES) and N-2-aminoethyl-3-aminopropyl trimethoxysilane. This linker is functionalized with the core and anti-microbial active group, respectively, through the functional group thereof (i.e., hydroxyl, siloxane, carboxy, amide or sulfonate). In another embodiment, this linker is directly attached to the core at one end directly or indirectly, via a third linker (L3) and is modified at the other end to anti-microbial active group [—$^+N(R_1)(R_2)(R_3)$, —$^+NH(R_1)(R_2)$, —$N(R_1)(R_2)$—$^+N(R_1')(R_2')(R_3')$, —$^+NH(R_1')(R_2')$ or —$N(R_1')(R_2')$ (defined in structures (1) to (6))].

In one embodiment, the anti-microbial active group of this invention may be selected from: (a) a tertiary amine (i.e. $R_3$ and/or $R_3$' is nothing) or tertiary ammonium (i.e. $R_3$ and/or $R_3$' is hydrogen) comprising at least one terpenoid moiety (b) a quaternary ammonium group comprising at least one terpenoid moiety (c) a quaternary ammonium group, comprising at least one alkyl group having from 4 to 24 carbon atoms; and (d) a tertiary amine (i.e. $R_3$ and/or $R_3$' is nothing) or tertiary ammonium (i.e. $R_3$ and/or $R_3$' is hydrogen) comprising at least one alkyl group having from 4 to 24 carbon atoms. Each possibility represents a separate embodiment of this invention.

This linker is functionalized with the core and anti-microbial active group, respectively, through the functional group thereof (i.e., hydroxyl, siloxane, carboxy, amide or sulfonate). In another embodiment, this linker is directly attached to the core at one end or indirectly, via a third linker (L3) and is modified at the other end to anti-microbial active group [—$^+N(R_1)(R_2)(R_3)$, —$^+NH(R_1)(R_2)$, —$N(R_1)(R_2)$—$^+N(R_1')(R_2')(R_3')$, —$^+NH(R_1')(R_2')$ or —$N(R_1')(R_2')$ (defined in structures (1) to (6))].

In another embodiment, a monomeric unit (as described in e.g. FIGS. 1B-1C and formulas 1-6) within the anti-microbial active unit of this invention is represented by the structure of formula IA:

(IA)

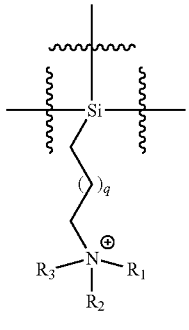

wherein $R_1$ and $R_2$ are independently linear or branched alkyl, terpenoid, cycloalkyl, aryl, heteroaryl, alkenyl, alkynyl or any combination thereof; and $R_3$ is nothing, linear or branched alkyl, terpenoid, cycloalkyl, aryl, heteroaryl, alkenyl, alkynyl or any combination thereof; wherein if $R_3$ is nothing, the nitrogen is not charged q is an integer between 0 and 16;

wherein said monomeric unit is chemically bound to the surface of an inorganic core directly or via a third linker (L3).

In another embodiment, a monomeric unit (as described in e.g. FIGS. 1B-1C and formulas 1-6) within the anti-microbial active unit of this invention is represented by the structure of formula IB:

(IB)

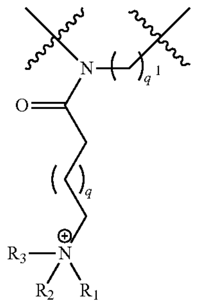

wherein $R_1$ and $R_2$ are independently linear or branched alkyl, terpenoid, cycloalkyl, aryl, heteroarylalkenyl, alkynyl or any combination thereof; and $R_3$ is nothing, linear or branched alkyl, terpenoid, cycloalkyl, aryl, heteroaryl, alkenyl, alkynyl or any combination thereof; wherein if $R_3$ in nothing, the nitrogen is not charged q and $q^1$ are independently an integer between 0 and 16;

wherein said monomeric unit is chemically bound to the surface of an inorganic core directly or via a third linker (L3).

In another embodiment, a linker molecule which may be used in the processes of preparing the anti-microbial particles of this invention is represented by the structure of formula IC:

(IC)

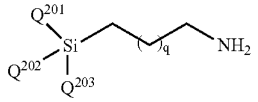

wherein $Q^{201}$, $Q^{202}$ and $Q^{203}$ are independently selected from the group consisting of alkoxy, methyl, ethyl, hydrogen, sulfonate and halide, wherein at least one of $Q^{201}$, $Q^{202}$ and $Q^{203}$ is selected from ethoxy, methoxy, sulfonate (e.g., mesyl, tosyl) and halide; and q is an integer between 0 and 16;

the linker molecule is capable of being chemically bound to the surface of the inorganic core through the silicon atom; and the anti-microbial active group is introduced by functionalizing the primary amine to obtain an anti-microbial active tertiary amine or quaternary ammonium group containing at least one terpenoid group, as described above.

In another embodiment, a linker molecule which may be used in the processes of preparing the anti-microbial particles of this invention is represented by the structure of formula ID:

(ID)

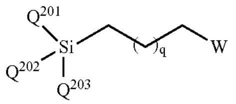

wherein $Q^{201}$, $Q^{202}$ and $Q^{203}$ are independently selected from the group consisting of alkoxy, methyl, ethyl, hydrogen, sulfonate and halide, wherein at least one of $Q^{201}$, $Q^{202}$ and $Q^{203}$ is selected from ethoxy, methoxy, sulfonate (e.g., mesyl, tosyl) and halide;

W is selected from the group consisting of $NH_2$, halide, sulfonate and hydroxyl; and q is an integer between 0 and 16; said linker is capable of being chemically bound to the surface of said inorganic core through the silicon atom; and the anti-microbial active group is introduced by substituting the group W with an anti-microbial active group, or converting the group W to an anti-microbial active group.

The particles of this invention demonstrate an enhanced anti-microbial activity. Without being bound by any theory or mechanism, it can be postulated that such activity originates from the presence of closely packed anti-microbial groups on a given core's surface, as well as high density of particles packed on the surface of a host material. This density increases as each anti-microbial active unit in the particles of this invention comprise increasing number of anti-microbial active groups and it yields a high local concentration of active functional groups, which results in high effective concentration of the anti-microbial active groups and enables the use of a relatively small amount of particles to achieve effective bacterial annihilation. The close packing of the anti-microbial groups is due to, inter alia, numerous anti-microbial active units protruding from each particle surface. Accordingly, the anti-microbial groups cover large fraction of the particle's available surface area (width dimension covering the surface). The surface density of the anti-microbial group results in high effective concentration promoting anti-microbial inhibitory effect. According to the principles of this invention, high surface density dictates high anti-microbial efficiency.

Anti-Microbial Active Groups Comprising One Long Alkyl Group.

In accordance with another embodiment, the anti-microbial active group of this invention [$—^{+}N(R_1)(R_2)(R_3)$, $—^{+}NH(R_1)(R_2)$, $—N(R_1)(R_2)—^{+}N(R_1')(R_2')(R_3')$, $—^{+}NH(R_1')(R_2')$ or $—N(R_1')(R_2')$ (defined in structures (1) to (6))] is a quaternary ammonium group, a tertiary amine or a tertiary ammonium, the nitrogen atom of each amine/ammonium group having at least one bond $X_1$ or $X_2$, at least one bond to an alkyl group having from 4 to 24 carbon atoms ($R_1$ and/or $R_1'$). In another embodiment, the nitrogen atom of each amine/ammonium group having one bond to the core, one bond to an alkyl group having from 4 to 24 carbon atoms ($R_1$ and/or $R_1'$).

Since an ammonium group is positively charged, its charge should be balanced with an anion. Any of the counter-ions described above may be used to counter-balance the quaternary ammonium group.

In some embodiments, the nitrogen atom of each quaternary ammonium or tertiary ammonium group has (i) at least one bond to $X_1$ or $X_2$; and (ii) at least one bond to the alkyl group having from 4 to 24 carbon atoms.

In some embodiments, the anti-microbial active group of formula (1) to (6) is selected from: (a) a tertiary amine ($R_3$ and/or $R_3'$ is nothing) or tertiary ammonium ($R_3$ and/or $R_3'$ is H), wherein the nitrogen atom of each tertiary amine/ammonium having at least one bond to $X_1$ or $X_2$ and one bond to the alkyl group having from 4 to 24 carbon atoms; (b) a tertiary amine ($R_3$ and/or $R_3'$ is nothing), or tertiary ammonium ($R_3$ and/or $R_3'$ is H), wherein the nitrogen atom of each tertiary amine/ammonium having one bond to $X_1$ or $X_2$ and two bonds to alkyl groups having from 4 to 24 carbon atoms which may be the same or different from each other, or a salt of said tertiary amine; (c) a quaternary ammonium group wherein the nitrogen atom of each quaternary ammonium group having at least one bond to $X_1$ or $X_2$ and one or two bonds to the alkyl groups having from 4 to 24 carbon atoms which may be the same or different from each other. Each possibility represents a separate embodiment of this invention.

The term "quaternary ammonium group" refers to a group of atoms consisting of a nitrogen atom with four substituents (different than hydrogen) attached thereto. In another embodiment, a "quaternary ammonium group" refers to a group of atoms consisting of a nitrogen atom with four groups wherein each of the group is attached to the nitrogen through a carbon atom. The term "long alkyl group" or chain refers to such an alkyl group or chain which is substituted on the nitrogen atom of the quaternary ammonium group and which has between 4 and 24 carbon atoms. In some currently preferred embodiments, the alkyl group is an alkyl group having 4 to 18 carbon atoms. In some currently preferred embodiments, the alkyl group is an alkyl group having 4 to 8 carbon atoms. In some currently preferred embodiments, the alkyl group is an alkyl group having 4 to 10 carbon atoms. In other currently preferred embodiments, the alkyl group is an alkyl group having 6, 7, or 8 carbon atoms, with each possibility representing a separate embodiment of this invention.

Thermal Stable Anti-Microbial Particles

In one embodiment, the anti-microbially particle is represented by structure (I):

(I)

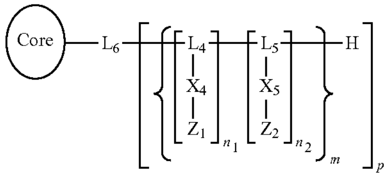

wherein the core is an organic polymer or an inorganic material;

$L_4$ is a first linker or a bond;

$L_5$ is a second linker;

$L_6$ is a third linker or a bond;

$Z_1$ is

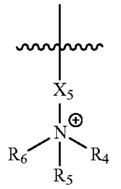

or

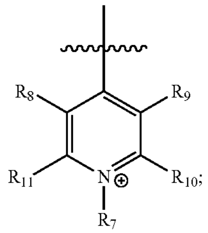

$Z_2$ is

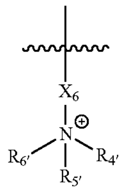

or

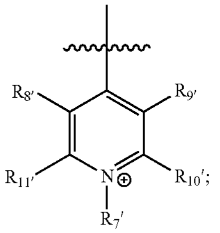

$R_4$ and $R_4'$ are each independently methyl, $CF_3$, perhaloalkyl, aryl, benzyl, 2,2-disubstituted $C_3$-$C_{20}$ alkyl, 2,2,2-trisubstituted ethyl, $—CH_2C(═O)OR$, $—CH_2C(═O)OC(═O)R$, $—CH_2C(═S)OR$, $—CH_2C(═O)SR$, $—C(═O)OR$, $—C(═O)OC(═O)R$, $—C(═S)OR$, $—C(═O)SR$, $—C(═O)—R$, $—C(═S)—R$, $—CH_2C(═O)R$, $—CH_2C(═S)R$, $—CH_2CF_3$, $—CH_2NO_2$, 1-alkenyl, 1-alkynyl, 2-alkenyl, 2-alkynyl or any combination thereof;

$R_5$ and $R_5'$ are each independently methyl, $CF_3$, perhaloalkyl, aryl, benzyl, 2,2-disubstituted $C_3$-$C_{20}$ alkyl, 2,2,2-trisubstituted ethyl, $—CH_2C(═O)OR$, $—CH_2C(═O)OC(═O)R$, $—CH_2C(═S)OR$, $—CH_2C(═O)SR$, $—C(═O)OR$, $—C(═O)OC(═O)R$, $—C(═S)OR$, $—C(═O)SR$, $—C(═O)—R$, $—C(═S)—R$, $—CH_2C(═O)R$, $—CH_2C(═S)R$, $—CH_2CF_3$, $—CH_2NO_2$, 1-alkenyl, 1-alkynyl, 2-alkenyl, 2-alkynyl or any combination thereof;

$R_6$ and $R_6'$ are each independently absent, methyl, $CF_3$, perhaloalkyl, 2,2-disubstituted $C_3$-$C_{20}$ alkyl, 2,2,2-trisubstituted ethyl, $—CH_2C(═O)OR$, $—CH_2C(═O)OC(═O)R$, $—CH_2C(═S)OR$, $—CH_2C(═O)SR$, $—C(═O)OR$, $—C(═O)OC(═O)R$, $—C(═S)OR$, $—C(═O)SR$, $—C(═O)—R$, $—C(═S)—R$, $—CH_2C(═O)R$, $—CH_2C(═S)R$, $—CH_2CF_3$, $—CH_2NO_2$, terpenoid moiety, cycloalkyl, aryl, phenyl, benzyl, heterocycle, a conjugated alkyl, 1-alkenyl, 1-alkynyl, 2-alkenyl, 2-alkynyl or any combination thereof;

$R_7$ and $R_7'$ are each independently methyl, $CF_3$, perhaloalkyl, aryl, benzyl, 2,2-disubstituted $C_3$-$C_{20}$ alkyl, 2,2,2-trisubstituted ethyl, $—CH_2C(═O)OR$, $—CH_2C(═O)OC(═O)R$, $—CH_2C(═S)OR$, $—CH_2C(═O)SR$, $—C(═O)OR$, $—C(═O)OC(═O)R$, $—C(═S)OR$, $—C(═O)SR$, $—C(═O)—R$, $—C(═S)—R$, $—CH_2C(═O)R$, $—CH_2C(═S)R$, $—CH_2CF_3$, $—CH_2NO_2$, 1-alkenyl, 1-alkynyl, 2-alkenyl, 2-alkynyl or any combination thereof;

$R_8$ and $R_8'$ are each independently H, alkyl, terpenoid moiety, cycloalkyl, aryl, heterocycle, a conjugated alkyl, alkenyl, alkynyl or any combination thereof;

$R_9$ and $R_9$' are each independently H, alkyl, terpenoid moiety, cycloalkyl, aryl, heterocycle, a conjugated alkyl, alkenyl, alkynyl or any combination thereof;

$R_{10}$ and $R_{10}$' are each independently H, alkyl, terpenoid moiety, cycloalkyl, aryl, heterocycle, a conjugated alkyl, alkenyl, alkynyl or any combination thereof;

$R_{11}$ and $R_{11}$' are each independently H, alkyl, terpenoid moiety, cycloalkyl, aryl, heterocycle, a conjugated alkyl, alkenyl, alkynyl or any combination thereof;

$X_3$ and $X_4$ are each independently a bond, alkylene, arylene, alkenylene, alkynylene or any combination thereof;

$X_5$ and $X_6$ are each independently a bond, —O—C(═O)—, methylene, —O—C(═O)—$CH_2$—, 2,2-disubstituted $C_2$-$C_{20}$ alkylene, arylene, phenylene, benzylene, cycloalkylene, a heterocycle, a conjugated alkylene, a terpenoid moiety, 1-alkenylene, 1-alkynylene, 2-alkenylene, 2-alkynylene or any combination thereof;

R is alkyl, aryl, cycloalkyl, heterocycle or any combination thereof;

p defines the number of anti-microbial active unit per one sq nm ($nm^2$) of the core surface, wherein said density is of between 0.01-30 anti-microbial units per one sq nm ($nm^2$) of the core surface of the particle;

$n_1$ is each independently an integer between 0 to 200;

$n_2$ is each independently an integer between 0 to 200;

wherein $n_1+n_2 \geq 1$; and m is an integer between 1 to 200 and the repeating unit is the same or different.

In another embodiment, provided that $Z_1$ or $Z_2$ comprises an ammonium nitrogen (not pyridinium)—in each of the anti-microbial active units only one moiety on the ammonium may have beta hydrogens available for hofmann elimination. In another embodiment, provided that $Z_1$ or $Z_2$ comprises an ammonium nitrogen (not pyridinium)—in each of the anti-microbial active units two moieties on the ammonium may have beta hydrogens available for hofmann elimination. In another embodiment, beta hydrogens available for hofmann elimination are those which are found on beta (compared to the ammonium nitrogen) aliphatic carbon and can be eliminated to release an olefin and a tertiary amine.

In another embodiment, the anti-microbially particle is represented by structure (IE):

(IE)

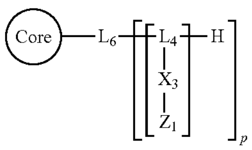

wherein the core is an organic polymer or an inorganic material;

$L_4$ is a first linker or a bond;

$L_6$ is a third linker or a bond;

$Z_1$ is

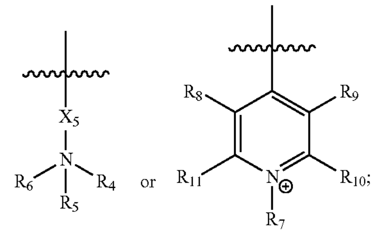

$R_4$ is methyl, $CF_3$, perhaloalkyl, aryl, benzyl, 2,2-disubstituted $C_3$-$C_{20}$ alkyl, 2,2,2-trisubstituted ethyl, —$CH_2$C(═O)OR, —$CH_2$C(═O)OC(═O)R, —$CH_2$C(═S)OR, —$CH_2$C(═O)SR, —C(═O)OR, —C(═O)OC(═O)R, —C(═S)OR, —C(═O)SR, —$CH_2$C(═O)R, —$CH_2$C(═S)R, —$CH_2CF_3$, —$CH_2NO_2$, 1-alkenyl, 1-alkynyl, 2-alkenyl, 2-alkynyl or any combination thereof;

$R_5$ is methyl, $CF_3$, perhaloalkyl, aryl, benzyl, 2,2-disubstituted $C_3$-$C_{20}$ alkyl, 2,2,2-trisubstituted ethyl, —$CH_2$C(═O)OR, —$CH_2$C(═O)OC(═O)R, —$CH_2$C(═S)OR, —$CH_2$C(═O)SR, —C(═O)OR, —C(═O)OC(═O)R, —C(═S)OR, —C(═O)SR, —C(═O)—R, —C(═S)—R, —$CH_2$C(═O)R, —$CH_2$C(═S)R, —$CH_2CF_3$, —$CH_2NO_2$, 1-alkenyl, 1-alkynyl, 2-alkenyl, 2-alkynyl or any combination thereof;

$R_6$ is methyl, $CF_3$, perhaloalkyl, 2,2-disubstituted $C_3$-$C_{20}$ alkyl, 2,2,2-trisubstituted ethyl, —$CH_2$C(═O)OR, —$CH_2$C(═O)OC(═O)R, —$CH_2$C(═S)OR, —$CH_2$C(═O)SR, —C(═O)OR, —C(═O)OC(═O)R, —C(═S)OR, —C(═O)SR, —C(═O)—R, —C(═S)—R, —$CH_2$C(═O)R, —$CH_2$C(═S)R, —$CH_2CF_3$, —$CH_2NO_2$, terpenoid moiety, cycloalkyl, aryl, phenyl, benzyl, heterocycle, a conjugated alkyl, 1-alkenyl, 1-alkynyl, 2-alkenyl, 2-alkynyl or any combination thereof;

$R_7$ is methyl, $CF_3$, perhaloalkyl, aryl, benzyl, 2,2-disubstituted $C_3$-$C_{20}$ alkyl, 2,2,2-trisubstituted ethyl, —$CH_2$C(═O)OR, —$CH_2$C(═O)OC(═O)R, —$CH_2$C(═S)OR, —$CH_2$C(═O)SR, —C(═O)OR, —C(═O)OC(═O)R, —C(═S)OR, —C(═O)SR, —C(═O)—R, —C(═S)—R, —$CH_2$C(═O)R, —$CH_2$C(═S)R, —$CH_2CF_3$, —$CH_2NO_2$, 1-alkenyl, 1-alkynyl, 2-alkenyl, 2-alkynyl or any combination thereof;

$R_8$ is H, alkyl, terpenoid moiety, cycloalkyl, aryl, heterocycle, a conjugated alkyl, alkenyl, alkynyl or any combination thereof;

$R_9$ is H, alkyl, terpenoid moiety, cycloalkyl, aryl, heterocycle, a conjugated alkyl, alkenyl, alkynyl or any combination thereof;

$R_{10}$ is H, alkyl, terpenoid moiety, cycloalkyl, aryl, heterocycle, a conjugated alkyl, alkenyl, alkynyl or any combination thereof;

$R_{11}$ is H, alkyl, terpenoid moiety, cycloalkyl, aryl, heterocycle, a conjugated alkyl, alkenyl, alkynyl or any combination thereof;

$X_3$ is a bond, alkylene, arylene, alkenylene, alkynylene or any combination thereof;

$X_5$ is a bond, —O—C(═O)—, methylene, —O—C(═O)—$CH_2$—, 2,2-disubstituted $C_2$-$C_{20}$ alkylene, arylene, phenylene, benzylene, cycloalkylene, a heterocycle, a conjugated alkylene, a terpenoid moiety, 1-alkenylene, 1-alkynylene, 2-alkenylene, 2-alkynylene or any combination thereof;

R is alkyl, aryl, cycloalkyl, heterocycle or any combination thereof; and p defines the number of anti-microbial active unit per one sq nm ($nm^2$) of the core surface, wherein said density is of between 0.01-30 anti-microbial units per one sq nm ($nm^2$) of the core surface of the particle.

In another embodiment, provided that $Z_1$ comprises an ammonium nitrogen (not pyridinium)—in each of the anti-microbial active units only one moiety on the ammonium may have beta hydrogens available for hofmann elimination. In another embodiment, provided that $Z_1$ or $Z_2$ comprises an ammonium nitrogen (not pyridinium)—in each of the anti-microbial active units two moieties on the ammonium may have beta hydrogens available for hofmann elimination.

In another embodiment, the anti-microbially particle is represented by structure (II):

conjugated alkyl, 1-alkenyl, 1-alkynyl, 2-alkenyl, 2-alkynyl or any combination thereof;

$R_7$ and $R_7'$ are each independently methyl, $CF_3$, perhaloalkyl, aryl, benzyl, 2,2-disubstituted $C_3$-$C_{20}$ alkyl, 2,2,2-trisubstituted ethyl, —$CH_2C$(═O)OR, —$CH_2C$(═O)OC(═O)R, —$CH_2C$(═S)OR, —$CH_2C$(═O)SR, —C(═O)OR, —C(═O)OC(═O)R, —C(═S)OR, —C(═O)SR, —C(═O)—R, —C(═S)—R, —$CH_2C$(═O)R, —$CH_2C$(═S)R, —$CH_2CF_3$, —$CH_2NO_2$, 1-alkenyl, 1-alkynyl, 2-alkenyl, 2-alkynyl or any combination thereof;

$R_8$ and $R_8'$ are each independently H, alkyl, terpenoid moiety, cycloalkyl, aryl, heterocycle, a conjugated alkyl, alkenyl, alkynyl or any combination thereof;

(II)

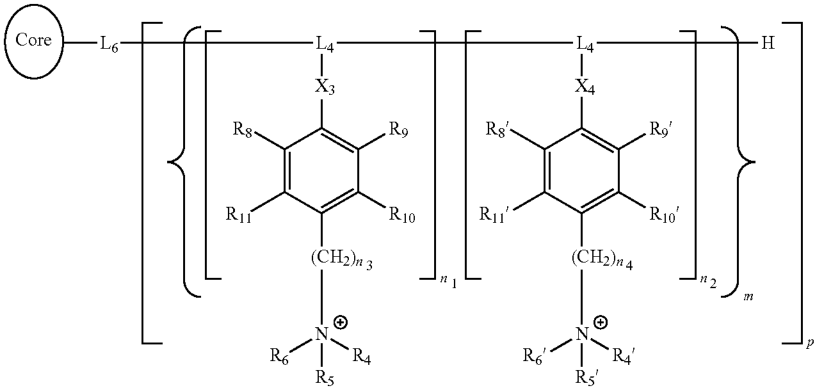

wherein the core is an organic polymer or an inorganic material;

$L_4$ is a first linker or a bond;

$L_5$ is a second linker;

$L_6$ is a third linker or a bond;

$R_4$ and $R_4'$ are each independently methyl, $CF_3$, perhaloalkyl, aryl, benzyl, 2,2-disubstituted $C_3$-$C_{20}$ alkyl, 2,2,2-trisubstituted ethyl, —$CH_2C$(═O)OR, —$CH_2C$(═O)OC(═O)R, —$CH_2C$(═S)OR, —$CH_2C$(═O)SR, —C(═O)OR, —C(═O)OC(═O)R, —C(═S)OR, —C(═O)SR, —C(═O)—R, —C(═S)—R, —$CH_2C$(═O)R, —$CH_2C$(═S)R, —$CH_2CF_3$, —$CH_2NO_2$, 1-alkenyl, 1-alkynyl, 2-alkenyl, 2-alkynyl or any combination thereof;

$R_5$ and $R_5'$ are each independently methyl, $CF_3$, perhaloalkyl, aryl, benzyl, 2,2-disubstituted $C_3$-$C_{20}$ alkyl, 2,2,2-trisubstituted ethyl, —$CH_2C$(═O)OR, —$CH_2C$(═O)OC(═O)R, —$CH_2C$(═S)OR, —$CH_2C$(═O)SR, —C(═O)OR, —C(═O)OC(═O)R, —C(═S)OR, —C(═O)SR, —C(═O)—R, —C(═S)—R, —$CH_2C$(═O)R, —$CH_2C$(═S)R, —$CH_2CF_3$, —$CH_2NO_2$, 1-alkenyl, 1-alkynyl, 2-alkenyl, 2-alkynyl or any combination thereof;

$R_6$ and $R_6'$ are each independently methyl, $CF_3$, perhaloalkyl, 2,2-disubstituted $C_3$-$C_{20}$ alkyl, 2,2,2-trisubstituted ethyl, —$CH_2C$(═O)OR, —$CH_2C$(═O)OC(═O)R, —$CH_2C$(═S)OR, —$CH_2C$(═O)SR, —C(═O)OR, —C(═O)OC(═O)R, —C(═S)OR, —C(═O)SR, —C(═O)—R, —C(═S)—R, —$CH_2C$(═O)R, —$CH_2C$(═S)R, —$CH_2CF_3$, —$CH_2NO_2$, terpenoid moiety, cycloalkyl, aryl, phenyl, benzyl, heterocycle, a $R_9$ and $R_9'$ are each independently H, alkyl, terpenoid moiety, cycloalkyl, aryl, heterocycle, a conjugated alkyl, alkenyl, alkynyl or any combination thereof;

$R_{10}$ and $R_{10}'$ are each independently H, alkyl, terpenoid moiety, cycloalkyl, aryl, heterocycle, a conjugated alkyl, alkenyl, alkynyl or any combination thereof;

$R_{11}$ and $R_{11}'$ are each independently H, alkyl, terpenoid moiety, cycloalkyl, aryl, heterocycle, a conjugated alkyl, alkenyl, alkynyl or any combination thereof;

$X_3$ and $X_4$ are each independently a bond, alkylene, arylene, alkenylene, alkynylene or any combination thereof;

R is alkyl, aryl, cycloalkyl, heterocycle or any combination thereof;

p defines the number of anti-microbial active unit per one sq nm ($nm^2$) of the core surface, wherein said density is of between 0.01-30 anti-microbial units per one sq nm ($nm^2$) of the core surface of the particle;

$n_1$ is each independently an integer between 0 to 200;

$n_2$ is each independently an integer between 0 to 200;

$n_3$ and $n_4$ are each independently 0 or 1;

wherein $n_1+n_2 \geq 1$; and m is an integer between 1 to 200 and the repeating unit is the same or different.

In another embodiment, in each of the anti-microbial active units only one moiety on the ammonium may have beta hydrogens available for hofmann elimination.

In another embodiment, the anti-microbially particle is represented by structure (III):

(III)

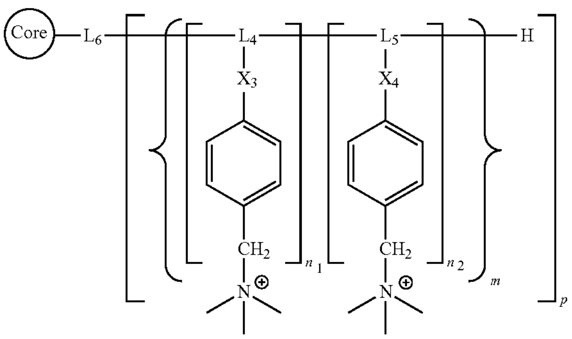

wherein the core is an organic polymer or an inorganic material;

$L_4$ is a first linker or a bond;

$L_5$ is a second linker;

$L_6$ is a third linker or a bond;

$X_3$ and $X_4$ are each independently a bond, alkylene, arylene, alkenylene, alkynylene or any combination thereof;

p defines the number of anti-microbial active unit per one sq nm ($nm^2$) of the core surface, wherein said density is of between 0.01-30 anti-microbial units per one sq nm ($nm^2$) of the core surface of the particle;

$n_1$ is each independently an integer between 0 to 200;

$n_2$ is each independently an integer between 0 to 200; wherein $n_1+n_2\geq 1$; and m is an integer between 1 to 200 and the repeating unit is the same or different.

In another embodiment, the anti-microbially particle is represented by structure (IV):

(IV)

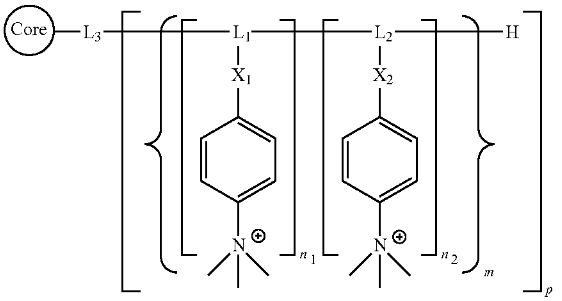

wherein the core is an organic polymer or an inorganic material;

$L_4$ is a first linker or a bond;

$L_5$ is a second linker;

$L_6$ is a third linker or a bond;

$X_3$ and $X_4$ are each independently a bond, alkylene, arylene, alkenylene, alkynylene or any combination thereof;

p defines the number of anti-microbial active unit per one sq nm ($nm^2$) of the core surface, wherein said density is of between 0.01-30 anti-microbial units per one sq nm ($nm^2$) of the core surface of the particle;

$n_1$ is each independently an integer between 0 to 200;

$n_2$ is each independently an integer between 0 to 200; wherein $n_1+n_2\geq 1$; and m is an integer between 1 to 200 and the repeating unit is the same or different.

In another embodiment, the anti-microbially particle is represented by structure (V):

(V)

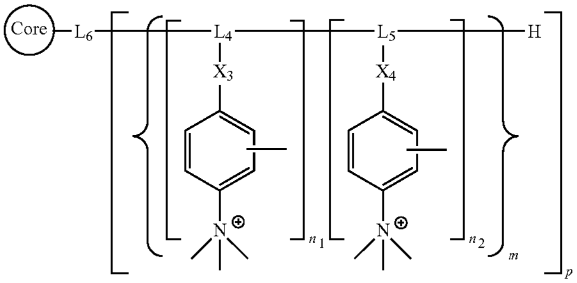

wherein the core is an organic polymer or an inorganic material;

$L_4$ is a first linker or a bond;

$L_5$ is a second linker;

$L_6$ is a third linker or a bond;

$X_3$ and $X_4$ are each independently a bond, alkylene, arylene, alkenylene, alkynylene or any combination thereof;

p defines the number of anti-microbial active unit per one sq nm ($nm^2$) of the core surface, wherein said density is of between 0.01-30 anti-microbial units per one sq nm ($nm^2$) of the core surface of the particle;

$n_1$ is each independently an integer between 0 to 200;

$n_2$ is each independently an integer between 0 to 200; wherein $n_1+n_2\geq 1$; and m is an integer between 1 to 200 and the repeating unit is the same or different.

In another embodiment, the anti-microbially particle is represented by structure (VI):

(VI)

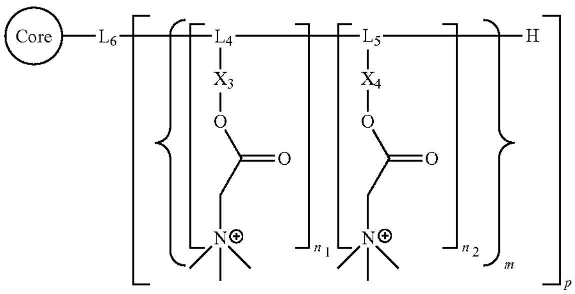

wherein the core is an organic polymer or an inorganic material;

$L_4$ is a first linker or a bond;

$L_5$ is a second linker;

$L_6$ is a third linker or a bond;

$X_3$ and $X_4$ are each independently a bond, alkylene, arylene, alkenylene, alkynylene or any combination thereof;

p defines the number of anti-microbial active unit per one sq nm ($nm^2$) of the core surface, wherein said density is of between 0.01-30 anti-microbial units per one sq nm ($nm^2$) of the core surface of the particle;

$n_1$ is each independently an integer between 0 to 200;

$n_2$ is each independently an integer between 0 to 200;

wherein $n_1+n_2 \geq 1$; and m is an integer between 1 to 200 and the repeating unit is the same or different.

In another embodiment, the anti-microbially particle is represented by structure (VII):

(VII)

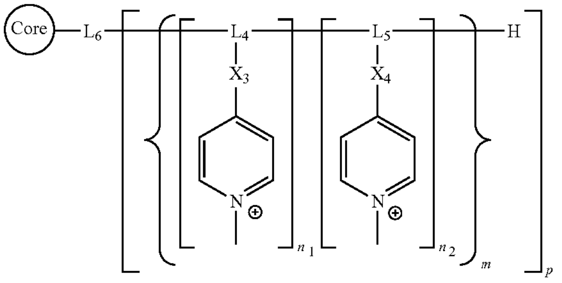

wherein the core is an organic polymer or an inorganic material;

$L_4$ is a first linker or a bond;

$L_5$ is a second linker;

$L_6$ is a third linker or a bond;

$X_3$ and $X_4$ are each independently a bond, alkylene, arylene, alkenylene, alkynylene or any combination thereof;

p defines the number of anti-microbial active unit per one sq nm ($nm^2$) of the core surface, wherein said density is of between 0.01-30 anti-microbial units per one sq nm ($nm^2$) of the core surface of the particle;

$n_1$ is each independently an integer between 0 to 200;

$n_2$ is each independently an integer between 0 to 200;

wherein $n_1+n_2 \geq 1$; and m is an integer between 1 to 200 and the repeating unit is the same or different.

In some embodiments, the anti-microbial particles of structures (I), (IE) and (II)-(VII) have high thermal stability. Without being bound by any mechanism or theory, it is suggested that the high stability stems from lack of available beta (β) hydrogens on the ammonium or a low number thereof, thus reducing the possibility of having a hofmann elimination which in turn gives rise to reduced thermal stability.

In some embodiments, the term "anti-microbial active group" and the term "monomeric anti-microbial active group" refer to the same and comprise a quaternary ammonium and/or a pyridinium, as represented by the following formulas:

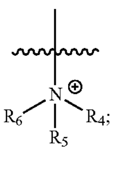

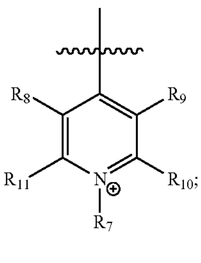

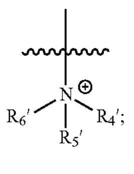

or

-continued

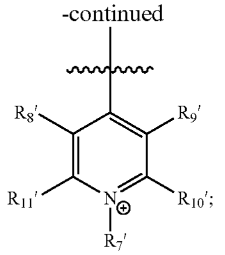

wherein:

$R_4$-$R_{11}$ and $R_4'$-$R_{11}'$ are as described hereinabove.

In another embodiment, the number of the anti-microbial active groups per each anti-microbial active unit is at least two, i.e. $n_1+n_2 \geq 2$ and $m \geq 1$. In another embodiment, the number of the anti-microbial active groups per each anti-microbial active unit is one, i.e. $n_1+n_2=1$ and $m=1$.

In another embodiment, the particles of structure (IE) comprise one monomeric unit per one anti-microbial active unit. In another embodiment, the particles of structures (I) and (II) to (VII) comprise one or more than one anti-microbial active group per one anti-microbial active unit.

The anti-microbial active groups of this invention are chemically bound to the core at a surface density of at least one anti-microbial active group per 10 sq. nm of the core surface. In another embodiment at least 1 anti-microbial group per 1 sq nm of the core surface. In another embodiment between 0.001-300 anti-microbial groups per sq nm of the core surface. In another embodiment between 0.001-250 anti-microbial groups per sq nm of the core surface. In another embodiment between 0.001-200 anti-microbial groups per sq nm of the core surface. In another embodiment between 0.001-150 anti-microbial groups per sq nm of the core surface. In another embodiment between 0.001-100 anti-microbial groups per sq nm of the core surface. In another embodiment between 0.001-50 anti-microbial groups per sq nm of the core surface. In another embodiment between 0.001-20 anti-microbial groups per sq nm of the core surface. In another embodiment between 0.001-17 anti-microbial groups per sq nm of the core surface. In another embodiment between 0.001-15 anti-microbial groups per sq nm of the core surface. In another embodiment between 0.001-10 anti-microbial groups per sq nm of the core surface. In another embodiment between 0.001-4 anti-microbial groups per sq nm of the core surface. In another embodiment between 0.001-1 anti-microbial groups per sq nm of the core surface. In another embodiment between 50-100 anti-microbial groups per sq nm of the core surface. In another embodiment between 100-150 anti-microbial groups per sq nm of the core surface. In another embodiment between 150-200 anti-microbial groups per sq nm of the core surface. In another embodiment between 200-250 anti-microbial groups per sq nm of the core surface. In another embodiment between 250-300 anti-microbial groups per sq nm of the core surface. In another embodiment between 1-4 anti-microbial groups per sq nm of the core surface. In another embodiment between 1-6 anti-microbial groups per sq nm of the core surface. In another embodiment between 1-20 anti-microbial groups per sq nm of the core surface. In another embodiment between 1-10 anti-microbial groups per sq nm of the core surface. In another embodiment between 1-15 anti-microbial groups per sq nm of the core surface.

In some embodiments, the number of the anti-microbial active groups $[(n_1+n_2) \times m]$ per each anti-microbial active unit is between 1-200. In another embodiment, the number of the anti-microbial active groups per each anti-microbial active unit is between 1-150. In another embodiment, the number of the anti-microbial active groups per each anti-microbial active unit is between 1-100. In another embodiment, the number of the anti-microbial active groups per each anti-microbial active unit is between 1-50. In another embodiment, the number of the anti-microbial active groups per each anti-microbial active unit is between 1-30. In another embodiment, the number of the anti-microbial active groups per each anti-microbial active unit is between 1-20. In another embodiment, the number of the anti-microbial active groups per each anti-microbial active unit is between 1-10. In another embodiment, the number of the anti-microbial active groups per each anti-microbial active unit is between 50-100. In another embodiment, the number of the anti-microbial active groups per each anti-microbial active unit is between 100-150. In another embodiment, the number of the anti-microbial active unit per each anti-microbial active unit is between 150-200.

In some embodiments, the number of the monomeric units per each anti-microbial active unit is between 1-200. In another embodiment, the number of the monomeric units per each anti-microbial active unit is between 1-150. In another embodiment, the number of the monomeric units per each anti-microbial active unit is between 1-100. In another embodiment, the number of the monomeric units per each anti-microbial active unit is between 1-50. In another embodiment, the number of the monomeric units per each anti-microbial active unit is between 1-30. In another embodiment, the number of monomeric units per each anti-microbial active unit is between 1-20. In another embodiment, the number of the monomeric units per each anti-microbial active unit is between 1-10. In another embodiment, the number of the monomeric units per each anti-microbial active unit is between 50-100. In another embodiment, the number of the monomeric units per each anti-microbial active unit is between 100-150. In another embodiment, the number of the monomeric units per each anti-microbial active unit is between 150-200.

In another embodiment, the particle of structures (I), (IE) and (II)-(VII) has an inorganic core. In another embodiment, the particle of structure (I), (IE) and (II)-(VII) has an organic core. In another embodiment, the organic core is a polymeric organic core. In another embodiment, the core is inert.

In one embodiment, $Z_1$ is

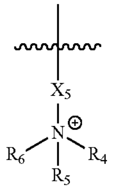
or
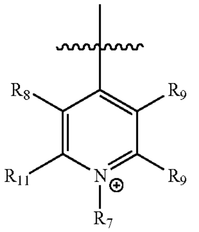

wherein $X_5$ and $R_4$-$R_{11}$ are as described hereinbelow. Each possibility represents a separate embodiment of this invention.

In one embodiment, $Z_2$ is

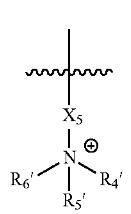
or
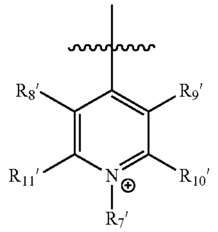

wherein $X_6$ and $R_{4'}$-$R_{11'}$ are as described hereinbelow. Each possibility represents a separate embodiment of this invention.

In one embodiment, $R_4$ and/or $R_4'$, $R_5$ and/or $R_5'$ and $R_7$ and/or $R_7'$ are the same or different and are independently methyl, $CF_3$, perhaloalkyl, aryl, benzyl, 2,2-disubstituted $C_3$-$C_{20}$ alkyl, 2,2,2-trisubstituted ethyl, —$CH_2C$(═O)OR, —$CH_2C$(═O)OC(═O)R, —$CH_2C$(═S)OR, —$CH_2C$(═O)SR, —C(═O)OR, —C(═O)OC(═O)R, —C(═S)OR, —C(═O)SR, —C(═O)—R, —C(═S)—R, —$CH_2C$(═O)R, —$CH_2C$(═S)R, —$CH_2CF_3$, —$CH_2NO_2$, 1-alkenyl, 1-alkynyl, 2-alkenyl, 2-alkynyl or any combination thereof, wherein R is described hereinbelow. Each possibility represents a separate embodiment of this invention.

In one embodiment, $R_6$ and $R_6'$ are each independently absent, methyl, $CF_3$, perhaloalkyl, 2,2-disubstituted $C_3$-$C_{20}$ alkyl, 2,2,2-trisubstituted ethyl, —$CH_2C$(═O)OR, —$CH_2C$(═O)OC(═O)R, —$CH_2C$(═S)OR, —$CH_2C$(═O)SR, —C(═O)OR, —C(═O)OC(═O)R, —C(═S)OR, —C(═O)SR, —C(═O)—R, —C(═S)—R, —$CH_2C$(═O)R, —$CH_2C$(═S)R, —$CH_2CF_3$, —$CH_2NO_2$, terpenoid moiety, cycloalkyl, aryl, phenyl, benzyl, heterocycle, a conjugated alkyl, 1-alkenyl, 1-alkynyl, 2-alkenyl, 2-alkynyl or any combination thereof; Each possibility represents a separate embodiment of this invention.

In one embodiment, $R_8$ and/or $R_8'$, $R_9$ and/or $R_9'$, $R_{10}$ and/or $R_{10}'$ and $R_{11}$ and/or $R_{11}'$ are the same or different and are independently H, alkyl, terpenoid moiety, cycloalkyl, aryl, heterocycle, a conjugated alkyl, alkenyl, alkynyl or any combination thereof. Each possibility represents a separate embodiment of this invention.

In one embodiment, $X_3$ and/or $X_4$ are the same or different and are independently a bond, alkylene, arylene, alkenylene, alkynylene or any combination thereof. Each possibility represents a separate embodiment of this invention.

In one embodiment, $X_5$ and $X_6$ are each independently a bond, —O—C(═O)—, methylene, —O—C(═O)—$CH_2$—, 2,2-disubstituted $C_2$-$C_{20}$ alkylene, arylene, phenylene, benzylene, cycloalkylene, a heterocycle, a conjugated alkylene, a terpenoid moiety, 1-alkenylene, 1-alkynylene, 2-alkenylene, 2-alkynylene or any combination thereof. Each possibility represents a separate embodiment of this invention.

In one embodiment, R is alkyl, aryl, cycloalkyl, heterocycle or any combination thereof. Each possibility represents a separate embodiment of this invention.

In another embodiment $R_4$ and $R_4'$ are the same. In another embodiment $R_5$ and $R_5'$ are the same. In another embodiment $R_6$ and $R_6'$ are the same. In another embodiment $R_7$ and $R_7'$ are the same. In another embodiment $R_8$ and $R_8'$ are the same. In another embodiment $R_9$ and $R_9'$ are the same. In another embodiment $R_{10}$ and $R_{10}'$ are the same. In another embodiment $R_{11}$ and $R_{11}'$ are the same. In another embodiment $X_3$ and $X_4$ are the same. In another embodiment $X_5$ and $X_6$ are the same. In another embodiment $R_4$ and $R_4'$ are different. In another embodiment $R_5$ and $R_5'$ are different. In another embodiment $R_6$ and $R_6'$ are different. In another embodiment $R_7$ and $R_7'$ are different. In another embodiment $R_8$ and $R_8'$ are different. In another embodiment $R_9$ and $R_9'$ are different. In another embodiment $R_{10}$ and $R_{10}'$ are different. In another embodiment $R_{11}$ and $R_{11}'$ are different. In another embodiment $X_3$ and $X_4$ are different. In another embodiment $X_5$ and $X_6$ are different.

As used herein, the term "alkyl" or "alkylene" refer to any linear- or branched-chain alkyl group containing up to about 24 carbons unless otherwise specified. In one embodiment, an alkyl includes $C_1$-$C_3$ carbons. In one embodiment, an alkyl includes $C_1$-$C_4$ carbons. In one embodiment, an alkyl includes $C_1$-$C_5$ carbons. In another embodiment, an alkyl includes $C_1$-$C_6$ carbons. In another embodiment, an alkyl includes $C_1$-$C_8$ carbons. In another embodiment, an alkyl includes $C_1$-$C_{10}$ carbons. In another embodiment, an alkyl includes $C_1$-$C_{12}$ carbons. In another embodiment, an alkyl includes $C_4$-$C_8$ carbons. In another embodiment, an alkyl includes $C_4$-$C_{10}$ carbons. In another embodiment, an alkyl include $C_4$-$C_{18}$ carbons. In another embodiment, an alkyl include $C_4$-$C_{24}$ carbons. In another embodiment, an alkyl includes $C_1$-$C_{18}$ carbons. In another embodiment, an alkyl includes $C_2$-$C_{18}$ carbons. In another embodiment, branched alkyl is an alkyl substituted by alkyl side chains of 1 to 5 carbons. In one embodiment, the alkyl group may be unsubstituted. In another embodiment, the alkyl group may be substituted by a halogen, haloalkyl, hydroxyl, alkoxy, carbonyl, amido, alkylamido, dialkylamido, cyano, nitro, $CO_2H$, amino, alkylamino, dialkylamino, carboxyl, thio and/or thioalkyl. In another embodiment, the alkyl is a 2,2-disubstituted $C_3$-$C_{20}$ alkyl. The term "2,2-disubstituted $C_3$-$C_{20}$ alkyl" refers to alkyl as described herein, having between 3 and 20 carbons and is substituted thrice at the second carbon (from the connection point) with halogen, haloalkyl, alkyl, alkoxy, carbonyl, amido, alkylamido, dialkylamido, cyano, nitro, $CO_2H$, amino, alkylamino, dialkylamino, carboxyl, thio and/or thioalkyl, where such substitutions can be the same or different; or alternatively it is substituted once at the second carbon with oxo (═O) or with other double bond to an element (e.g. S) or a moiety (e.g. vinylic carbon or NH) and it's further substituted with a substitutent selected from the above list of the first possibility; in all cases—no hydrogen is available for abstraction at this second carbon position (i.e. no hydrogens are found at this position, only non-hydrogen substituents). Non-limiting examples of 2,2-disubstituted $C_3$-$C_{20}$ alkyl include neopentyl ($—CH_2—C(CH_3)_3$, $—CH_2—C(CH_3)_2—CH_2CH_3$, $CH_2—CF_2CH_3$ and $—CH_2C(═O)CH_3$. In another embodiment, the alkyl is a 2,2-disubstituted $C_3$-$C_8$ alkyl. In another embodiment, the alkyl is a 2,2-disubstituted $C_3$-$C_{10}$ alkyl. In another embodiment, the alkyl is a 2,2-disubstituted $C_3$-$C_{12}$ alkyl. In another embodiment, the alkyl is a 2,2-disubstituted $C_3$-$C_{18}$ alkyl. The terms "2,2-disubstituted $C_3$-$C_8$ alkyl", "2,2-disubstituted $C_3$-$C_{10}$ alkyl", "2,2-disubstituted $C_3$-$C_{12}$ alkyl" and "2,2-disubstituted $C_3$-$C_{18}$ alkyl" refer to similar moiety as "2,2-disubstituted $C_3$-$C_{20}$ alkyl" but with $C_3$-$C_8$, $C_3$-$C_{10}$, $C_3$-$C_{12}$ and $C_3$-$C_{18}$ alkyl, respectively. In another embodiment, alkylene is a 2,2-disubstituted $C_2$-$C_{20}$ alkylene. The term "2,2-disubstituted $C_2$-$C_{20}$ alkylene" refers to similar moiety as "2,2-disubstituted $C_3$-$C_{20}$ alkyl" but with alkylene as described herein which has between 2 and 20 carbons. Non-limiting examples of 2,2-disubstituted $C_2$-$C_{20}$ alkylene include neopentylene ($—CH_2—C(CH_3)_2—CH_2—$, $—CH_2—C(CH_3)_2—CH_2CH_2—$, $—CH_2—CF_2CH_2—$ and $—CH_2C(═O)CH_2—$. In another embodiment, the alkylene is a 2,2-disubstituted $C_2$-$C_8$ alkylene. In another embodiment, the alkylene is a 2,2-disubstituted $C_2$-$C_{10}$ alkylene. In another embodiment, the alkylene is a 2,2-disubstituted $C_2$-$C_{12}$ alkylene. In another embodiment, the alkylene is a 2,2-disubstituted $C_2$-$C_{18}$ alkylene. The terms "2,2-disubstituted $C_2$-$C_8$ alkylene", "2,2-disubstituted $C_2$-$C_{10}$ alkylene", "2,2-disubstituted $C_2$-$C_{12}$ alkylene" and "2,2-disubstituted $C_2$-$C_{18}$ alkylene" refer to similar moiety as "2,2-disubstituted $C_2$-$C_{20}$ alkylene" but with $C_2$-$C_8$, $C_2$-$C_{10}$, $C_2$-$C_{12}$ and $C_2$-$C_{18}$ alkylene, respectively.

In another embodiment, the alkyl is a 2,2,2-trisubstituted ethyl. The term "2,2,2-trisubstituted ethyl" refers to ethyl substituted thrice at the second carbon (from the connection point) with halogen, haloalkyl, alkoxy, carbonyl, amido, alkylamido, dialkylamido, cyano, nitro, $CO_2H$, amino, alkylamino, dialkylamino, carboxyl, thio and/or thioalkyl, where such substitutions can be the same or different; or alternatively it is substituted once at the second carbon with oxo (═O) or with other double bond to an element (e.g. S) or a moiety (e.g. vinylic carbon or NH) and it's further substituted with a substituent selected from the above list of the first possibility; in all cases—no hydrogen is available for abstraction at this second carbon position (i.e. no hydrogens are found at this position, only non-hydrogen substituents). Non-limiting examples of 2,2,2-trisubstituted ethyl include 2,2,2 trihaloethyl and $—CH_2C(═O)—NH_2$. In another embodiment hydrophobic alkyl refers to an alkyl having at least four carbons. In another embodiment hydrophobic alkyl refers to a $C_4$-$C_{24}$ alkyl. In another embodiment hydrophobic alkyl refers to a $C_4$-$C_8$ alkyl. In another embodiment hydrophobic alkyl refers to a $C_4$ alkyl. In another embodiment hydrophobic alkyl refers to a $C_5$ alkyl. In another embodiment hydrophobic alkyl refers to a $C_6$ alkyl. In another embodiment hydrophobic alkyl refers to a $C_7$ alkyl. In another embodiment hydrophobic alkyl refers to a $C_8$ alkyl.

As used herein, the term "aryl" refers to any aromatic ring that is directly bonded to another group and can be either substituted or unsubstituted. As used herein, the term "Arylene" refers to the same where it is directly bonded to two groups (i.e. arylene is e.g. phenylene, $—C_6H_4—$). In another embodiment, it can be directly bonded to more than two groups. The aryl or arylene group can be a sole substituent, or it can be a component of a larger substituent, such as in an arylalkyl, arylamino, arylamido, etc. Exemplary aryl (and similarly, arylene) groups include, without limitation, phenyl, tolyl, xylyl, furanyl, naphthyl, pyridinyl, pyrimidinyl, pyridazinyl, pyrazinyl, triazinyl, thiazolyl, oxazolyl, isooxazolyl, pyrazolyl, imidazolyl, thiophene-yl, pyrrolyl, phenylmethyl, phenylethyl, phenylamino, phenylamido, etc. Substitutions include but are not limited to: F, Cl, Br, I, $C_1$-$C_5$ linear or branched alkyl, $C_1$-$C_5$ linear or branched haloalkyl, $C_1$-$C_5$ linear or branched alkyl or alkoxy, $C_1$-$C_5$ linear or branched haloalkyl or haloalkoxy, $CF_3$, CN, $NO_2$, $—CH_2CN$, $NH_2$, NH-alkyl, $N(alkyl)_2$, hydroxyl, $—OC(O)CF_3$, $—OCH_2Ph$, —NHCO-alkyl, COOH, —C(O)Ph, C(O)O-alkyl, C(O)H, or $—C(O)NH_2$. In another embodiment, hydrophobic aryl or arylene refers to aryl or arylene having at least six carbons.

As used herein, the term "benzyl" refers to the $—CH_2—C_6H_5$ moiety and can be unsubstituted or substituted with the following non-limiting list of substituents: F, Cl, Br, I, $C_1$-$C_5$ linear or branched alkyl, $C_1$-$C_5$ linear or branched haloalkyl, $C_1$-$C_5$ linear or branched alkyl or alkoxy, $C_1$-$C_5$ linear or branched haloalkyl or haloalkoxy, $CF_3$, CN, $NO_2$, $—CH_2CN$, $NH_2$, NH-alkyl, $N(alkyl)_2$, hydroxyl, —OC(O)

$CF_3$, —$OCH_2Ph$, —NHCO-alkyl, COOH, —C(O)Ph, C(O)O-alkyl, C(O)H, or —$C(O)NH_2$. Similarly, "benzylene" refers to the —$CH_2$—$C_6H_4$— moiety and can be unsubstituted or substituted with the substituents described above for the benzyl moiety.

As used herein, the term "haloalkyl" refers to alkyl as described hereinabove and substituted at least once by halide (i.e. F, Cl, Br or I). In one embodiment, all of the alkyl is substituted by halides, i.e. no hydrogens are found in the haloalkyl, and is termed "perhaloalkyl" (e.g. $CF_3$: perfluoromethyl or $CCl_3$: perchloromethyl). In one embodiment, only part of the alkyl is substituted by halides (e.g. $CH_2CF_3$). In another embodiment, non limiting examples of haloalkyls include: $CF_3$, $CCl_3$, $CH_2CF_3$, $CF_2CF_3$, $CCl_2CCl_3$ and $CI_3$.

The term "alkenyl" or "alkenylene" refer to a substance that includes at least two carbon atoms and at least one double bond. The term "1-alkenyl" or "1-alkenylene" refers to the same, where the double bond is on the first carbon (from the connection point). The term "2-alkenyl" or "2-alkenylene" refers to the same, where the double bond is on the second carbon (from the connection point). The term "3-alkenyl" or "3-alkenylene" refers to the same, where the double bond is on the third carbon (from the connection point). In one embodiment, the alkenyl has 2-7 carbon atoms. In another embodiment, the alkenyl has 2-12 carbon atoms. In another embodiment, the alkenyl has 2-10 carbon atoms. In another embodiment, the alkenyl has 3-6 carbon atoms. In another embodiment, the alkenyl has 2-4 carbon atoms. In another embodiment, the alkenyl has 4-8 carbon atoms. In another embodiment hydrophobic alkenyl refers to alkenyl having at least four carbons. In another embodiment hydrophobic alkenyl refers to a $C_4$-$C_8$ alkenyl.

The term "alkynyl" or "alkynylene" refers to a substance that includes at least two carbon atoms and at least one triple bond. The term "1-alkynyl" or "1-alkynylene" refers to the same, where the triple bond is on the first carbon (from the connection point). The term "2-alkynyl" or "2-alkynylene" refers to the same, where the triple bond is on the second carbon (from the connection point). The term "3-alkynyl" or "3-alkynylene" refers to the same, where the triple bond is on the third carbon (from the connection point). In one embodiment, the alkynyl has 2-7 carbon atoms. In another embodiment, the alkynyl has 2-12 carbon atoms. In another embodiment, the alkynyl has 2-10 carbon atoms. In another embodiment, the alkynyl has 3-6 carbon atoms. In another embodiment, the alkynyl has 2-4 carbon atoms. In another embodiment, the alkynyl has 3-6 carbon atoms. In another embodiment, the alkynyl has 4-8 carbon atoms. In another embodiment hydrophobic alkynyl refers to alkynyl having at least four carbons. In another embodiment hydrophobic alkynyl refers to a $C_4$-$C_8$ alkenyl.

The term "alkoxy" refers in one embodiment to an alky as defined above bonded to an oxygen. Non limiting examples of alkoxy groups include: methoxy, ethoxy and isopropoxy.

A "cycloalkyl" group refers, in one embodiment, to a ring structure comprising carbon atoms as ring atoms, which may be either saturated or unsaturated, substituted or unsubstituted; and is directly bonded to one group (e.g. cyclohexyl-, $C_6H_{11}$—). In another embodiment the cycloalkyl is a 3-12 membered ring. In another embodiment the cycloalkyl is a 6 membered ring. In another embodiment the cycloalkyl is a 5-7 membered ring. In another embodiment the cycloalkyl is a 3-8 membered ring. In another embodiment, the cycloalkyl group may be unsubstituted or substituted by a halogen, alkyl, haloalkyl, hydroxyl, alkoxy, carbonyl, amido, alkylamido, dialkylamido, cyano, nitro, $CO_2H$, amino, alkylamino, dialkylamino, carboxyl, thio and/or thioalkyl. In another embodiment, the cycloalkyl ring may be fused to another saturated or unsaturated cycloalkyl or heterocyclic 3-8 membered ring. In another embodiment, the cycloalkyl ring is a saturated ring. In another embodiment, the cycloalkyl ring is an unsaturated ring. Non-limiting examples of a cycloalkyl group comprise cyclohexyl, cyclohexenyl, cyclopropyl, cyclopropenyl, cyclopentyl, cyclopentenyl, cyclobutyl, cyclobutenyl, cycloctyl, cycloctadienyl (COD), cycloctaene (COE) etc. In another embodiment hydrophobic cycloalkyl refers to a cycloalkyl having at least six carbons. A "cycloalkylene" group refers, in one embodiment, to the same definitions above of "cycloalkyl", however the cycloalkylene is directly bonded to two groups (e.g. -cyclohexylene-, —$C_6H_{10}$—). In another embodiment, it is directly bonded to more than two groups.

A "heterocycle" group refers, in one embodiment, to a ring structure comprising in addition to carbon atoms, sulfur, oxygen, nitrogen or any combination thereof, as part of the ring. In another embodiment the heterocycle is a 3-12 membered ring. In another embodiment the heterocycle is a 6 membered ring. In another embodiment the heterocycle is a 5-7 membered ring. In another embodiment the heterocycle is a 3-8 membered ring. In another embodiment, the heterocycle group may be unsubstituted or substituted by a halogen, alkyl, haloalkyl, hydroxyl, alkoxy, carbonyl, amido, alkylamido, dialkylamido, cyano, nitro, $CO_2H$, amino, alkylamino, dialkylamino, carboxyl, thio and/or thioalkyl. In another embodiment, the heterocycle ring may be fused to another saturated or unsaturated cycloalkyl or heterocyclic 3-8 membered ring. In another embodiment, the heterocyclic ring is a saturated ring. In another embodiment, the heterocyclic ring is an unsaturated ring. Non limiting examples of a heterocyclic rings comprise pyridine, piperidine, morpholine, piperazine, thiophene, pyrrole, benzodioxole, or indole. In another embodiment hydrophobic heterocyclic group refers to a heterocycle having at least six carbons. In one embodiment, the heterocycle is directly bonded to one group (e.g. pyridinyl,

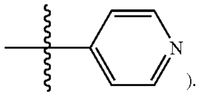 [SMILES: *c1ccncc1]

).

In one embodiment, the heterocycle is directly bonded to two groups (e.g. pyridinylene,

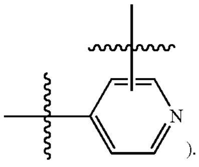

).

In one embodiment, the heterocycle is directly bonded to more than two groups.

In another embodiment, at least one of $R_4$, $R_5$ and $R_6$ and/or at least one of $R_4'$, $R_5'$ and $R_6'$ of structure (I) is/are hydrophobic.

The term "hydrophobic" refers to an alkyl, alkenyl or alkynyl having at least four carbons, or the term hydrophobic refers to terpenoid, to cycloalkyl, aryl or heterocycle having at least six carbons. Each possibility represents a separate embodiment of this invention.

In another embodiment, at least one of $R_6$, $R_8$-$R_{11}$ and $X_5$ and/or at least one of $R_{6'}$, $R_{8'}$-$R_{11'}$, and $X_6$ of structure (I) is a terpenoid. Each possibility represents a separate embodiment of this invention.

In one embodiment, "p" defines the surface density of the anti-microbial active units per 1 sq nm of the core surface. In another embodiment "p" is, between 0.01-30 anti-microbial active units per 1 sq nm of the core surface. In another embodiment "p" is, between 0.01-20 anti-microbial active units per 1 sq nm of the core surface. In another embodiment "p" is, between 0.01-10 anti-microbial active units per 1 sq nm of the core surface. In another embodiment "p" is, between 0.01-15 anti-microbial active units per 1 sq nm of the core surface. In another embodiment "p" is, between 0.01-5 anti-microbial active units per 1 sq nm of the core surface. Each possibility represents a separate embodiment of this invention.

In one embodiment, $n_1$ is between 0-200. In another embodiment, $n_1$ is between 0-10. In another embodiment, $n_1$ is between 10-20. In another embodiment, $n_1$ is between 20-30. In another embodiment, $n_1$ is between 30-40. In another embodiment, $n_1$ is between 40-50. In another embodiment, $n_1$ is between 50-60. In another embodiment, $n_1$ is between 60-70. In another embodiment, $n_1$ is between 70-80. In another embodiment, $n_1$ is between 80-90. In another embodiment, $n_1$ is between 90-100. In another embodiment, $n_1$ is between 100-110. In another embodiment, $n_1$ is between 110-120. In another embodiment, $n_1$ is between 120-130. In another embodiment, $n_1$ is between 130-140. In another embodiment, $n_1$ is between 140-150. In another embodiment, $n_1$ is between 150-160. In another embodiment, $n_1$ is between 160-170. In another embodiment, $n_1$ is between 170-180. In another embodiment, $n_1$ is between 180-190. In another embodiment, $n_1$ is between 190-200. Each possibility represents a separate embodiment of this invention.

In one embodiment, $n_2$ is between 0-200. In another embodiment, $n_2$ is between 0-10. In another embodiment, $n_2$ is between 10-20. In another embodiment, $n_2$ is between 20-30. In another embodiment, $n_2$ is between 30-40. In another embodiment, $n_2$ is between 40-50. In another embodiment, $n_2$ is between 50-60. In another embodiment, $n_2$ is between 60-70. In another embodiment, $n_2$ is between 70-80. In another embodiment, $n_2$ is between 80-90. In another embodiment, $n_2$ is between 90-100. In another embodiment, $n_2$ is between 100-110. In another embodiment, $n_2$ is between 110-120. In another embodiment, $n_2$ is between 120-130. In another embodiment, $n_2$ is between 130-140. In another embodiment, $n_2$ is between 140-150. In another embodiment, $n_2$ is between 150-160. In another embodiment, $n_2$ is between 160-170. In another embodiment, $n_2$ is between 170-180. In another embodiment, $n_2$ is between 180-190. In another embodiment, $n_2$ is between 190-200. Each possibility represents a separate embodiment of this invention.

In one embodiment, $n_3$ and $n_4$ of structure (II) are each independently 0 or 1. Each possibility represents a separate embodiment of this invention.

In one embodiment, m is between 1-200. In another embodiment, m is between 1-10. In another embodiment, m is between 10-20. In another embodiment, m is between 20-30. In another embodiment, m is between 30-40. In another embodiment, m is between 40-50. In another embodiment, m is between 50-60. In another embodiment, m is between 60-70. In another embodiment, m is between 70-80. In another embodiment, m is between 80-90. In another embodiment, m is between 90-100. In another embodiment, m is between 100-110. In another embodiment, m is between 110-120. In another embodiment, m is between 120-130. In another embodiment, m is between 130-140. In another embodiment, m is between 140-150. In another embodiment, m is between 150-160. In another embodiment, m is between 160-170. In another embodiment, m is between 170-180. In another embodiment, m is between 180-190. In another embodiment, m is between 190-200. Each possibility represents a separate embodiment of this invention.

In another embodiment, the anti-microbial active group of this invention may be selected from: (a) a quaternary ammonium group comprising at least one terpenoid moiety or one hydrophobic group; and (b) a pyridinium group. Each possibility represents a separate embodiment of this invention.

In one embodiment, the particles of this invention represented by structures (I)-(VII) comprise an anti-microbial active unit and an inert core, wherein the anti-microbial active unit and the core are linked directly or indirectly.

In some embodiments $L_4$, $L_5$ or $L_6$ is each independently the same or a different linker. In some embodiments, $L_4$, $L_5$ and $L_6$ are connected to each other, in any possible way. In some embodiment, $L_6$ is nothing and $L_4$ or $L_5$ is connected to the core covalently. In another embodiment, $L_6$ is connected to the core covalently and $L_4$ or $L_5$ is connected to $L_6$. In another embodiment, $L_4$ is connected to $X_3$, $L_5$ and $L_6$ or core. In another embodiment, a "linker" comprises any possible chemical moiety capable of connecting at least two other chemical moieties which are adjacent to such linker. In another embodiment, the monomeric unit of the anti-microbial active unit comprises a first and/or second linker/s ($L_4$ or $L_5$) and an anti-microbial group. In another embodiment, $L_4$ and/or $L_5$ are/is the backbone (they are e.g. alkylene, polypeptide or oligosiloxane ($—Si(OH)_2—O—$ or $—Si(CH_3)_2—O—$) moieties) of the anti-microbial active unit. In some embodiments, the linker comprises a functional group. In another embodiment, the linker comprises two (same or different) functional groups. In another embodiment, the functional group comprises phosphate, phosphonate, siloxane, silane, ether, acetal, hydroxyl, amide, amine, anhydride, ester, ketone, or aromatic ring or rings functionalized with any of the preceding moieties. Each possibility represents a separate embodiment of this invention.

In another embodiment, $L_4$, $L_5$, $L_6$, $X_3$, $X_4$, $X_5$, $X_6$ or any combination thereof is a C1 to C18 alkylene, alkenylene, alkynylene or aryl substituted with at least one carboxyl moiety, wherein the carboxyl end is attached to the core. It may be derived from a C1 to C18 alkylene substituted with at least one carboxyl moiety and having an amino end which is modified to anti-microbial active group [$—^+N(R_4)(R_5)(R_6)$, $—^+N(R_4')(R_5')(R_6')$,

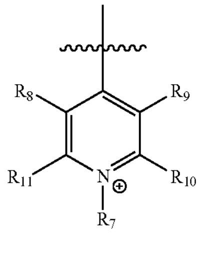

or

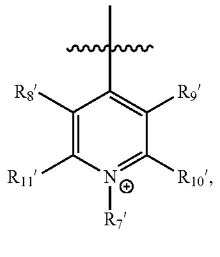

, defined in structures (I) and (IE)]. This linker may be derived from an amino acid of natural or synthetic source having a chain length of between 2 and 18 carbon atoms (polypeptide), or an acyl halide of said amino acid. Non-limiting examples for such amino acids are 18-amino octadecanoic acid and 18-amino stearic acid. In another embodiment, $L_4$, $L_5$, $L_6$, $X_3$, $X_4$, $X_5$, $X_6$ or any combination thereof is a C1 to C18 alkylene substituted with at least one amine, amide or pyridinium ( 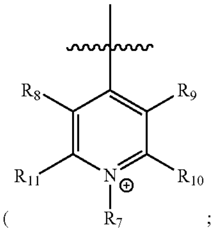 ; or 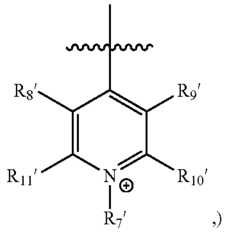 ,)

moiety.

In another embodiment, $L_4$, $L_5$, $L_6$, $X_3$, $X_4$, $X_5$, $X_6$ or any combination thereof is a C1 to C18 alkylene, alkenylene, alkynylene, arylene or aryl. This linker may be derived from a di-halo alkylene or di-haloarylene, which is functionalized at each end with the core and anti-microbial active group, respectively, by replacement of the halogen moiety to a functional group that binds to the core and replacement of the halogen moiety to obtain —$^+N(R_4)(R_5)(R_6)$ or —$^+N(R_4')(R_5')(R_6')$, which are defined in structures (I) to (II).

In another embodiment, $L_4$, $L_5$, $L_6$, $X_3$, $X_4$, $X_5$, $X_6$ or any combination thereof is an aromatic group derived from non-limiting examples of 4,4-biphenol, dibenzoic acid, dibenzoic halides, dibenzoic sulphonates, terephthalic acid, terephthalic halides, and terephthalic sulphonates. This linker is functionalized with the core and anti-microbial active group, respectively, through the functional group thereof (i.e., hydroxyl, carboxy or sulfonate). In another embodiment, this linker is directly attached to the core at one end or indirectly, via a third linker ($L_6$) and is modified at the other end to anti-microbial active group [—$^+N(R_4)(R_5)(R_6)$, —$^+N(R_4')(R_5')(R_6')$,

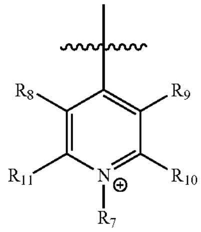 or 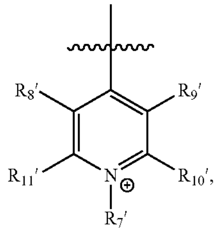

defined in structures (I) and (IE)].

In another embodiment, $L_4$, $L_5$, $L_6$, $X_3$, $X_4$, $X_5$, $X_6$ or any combination thereof, is a siloxane or silane group derived and/or selected from non-limiting examples of trialkoxyalkylsilane, trialkoxyarylsilane, trihaloalkylsilane, trihaloarylsilane, 3-aminopropyltriethoxysilane (APTES), (3-glycidyloxypropyl)trimethoxysilane and N-2-aminoethyl-3-aminopropyl trimethoxysilane. This linker is functionalized with the core and anti-microbial active group, respectively, through the functional group thereof (i.e., hydroxyl, siloxane, carboxy, amide or sulfonate). In another embodiment, this linker is directly attached to the core at one end directly or indirectly, via a third linker ($L_6$) and is modified at the other end to anti-microbial active group [—$^+N(R_4)(R_5)(R_6)$, —$^+N(R_4')(R_5')(R_6')$,

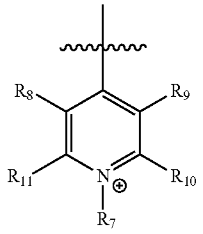 or 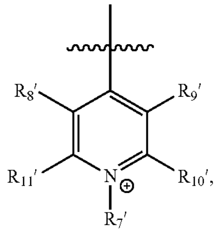

defined in structures (I) and (IE)].

This linker is functionalized with the core and anti-microbial active group, respectively, through the functional group thereof (i.e., hydroxyl, siloxane, carboxy, amide or sulfonate). In another embodiment, this linker is directly attached to the core at one end or indirectly, via a third linker ($L_6$) and is modified at the other end to anti-microbial active [—$^+N(R_4)(R_5)(R_6)$, —$^+N(R_4')(R_5')(R_6')$,

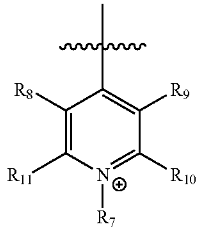 or 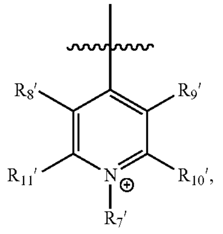

defined in structures (I) and (IE)].

In another embodiment, a monomeric unit (as described in e.g. FIGS. 1B-1C and formulas IE and I-VII) within the anti-microbial active unit of this invention is represented by the structure of formula IF1 or IF2:

(IF1)

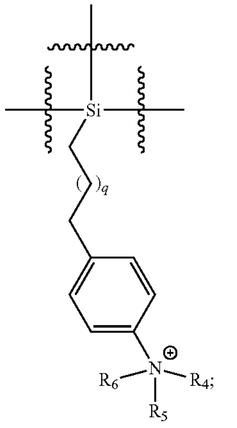 or

-continued (IF2)

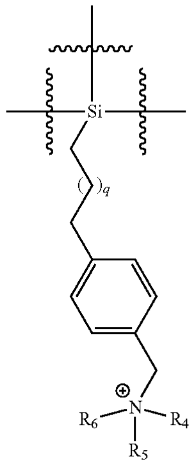

wherein $R_4$ and $R_5$ are independently methyl, $CF_3$, perhaloalkyl, aryl, benzyl, 2,2-disubstituted $C_3$-$C_{20}$ alkyl, 2,2,2-trisubstituted ethyl, —$CH_2C$(═O)OR, —$CH_2C$(═O)OC(═O)R, —$CH_2C$(═S)OR, —$CH_2C$(═O)SR, —C(═O)OR, —C(═O)OC(═O)R, —C(═S)OR, —C(═O)SR, —C(═O)—R, —C(═S)—R, —$CH_2C$(═O)R, —$CH_2C$(═S)R, —$CH_2CF_3$, —$CH_2NO_2$, 1-alkenyl, 1-alkynyl, 2-alkenyl, 2-alkynyl or any combination thereof;

$R_6$ is methyl, $CF_3$, perhaloalkyl, 2,2-disubstituted $C_3$-$C_{20}$ alkyl, 2,2,2-trisubstituted ethyl, —$CH_2C$(═O)OR, —$CH_2C$(═O)OC(═O)R, —$CH_2C$(═S)OR, —$CH_2C$(═O)SR, —C(═O)OR, —C(═O)OC(═O)R, —C(═S)OR, —C(═O)SR, —C(═O)—R, —C(═S)—R, —$CH_2C$(═O)R, —$CH_2C$(═S)R, —$CH_2CF_3$, —$CH_2NO_2$, terpenoid moiety, cycloalkyl, aryl, phenyl, benzyl, heterocycle, a conjugated alkyl, 1-alkenyl, 1-alkynyl, 2-alkenyl, 2-alkynyl or any combination thereof;

R is alkyl, aryl, cycloalkyl, heterocycle or any combination thereof;

q is an integer between 0 and 16; and wherein said monomeric unit is chemically bound to the surface of an inorganic core directly or via a third linker (L6).

In another embodiment, a monomeric unit (as described in e.g. FIGS. 1B-1C and formulas IE and I-VII) within the anti-microbial active unit of this invention is represented by the structure of formula IG1 or IG2:

(IG1)

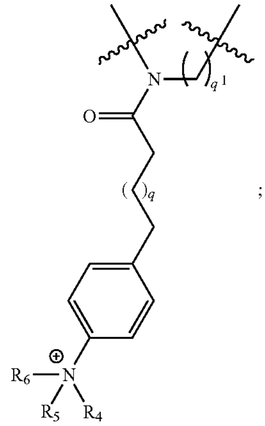

; or (IG2)

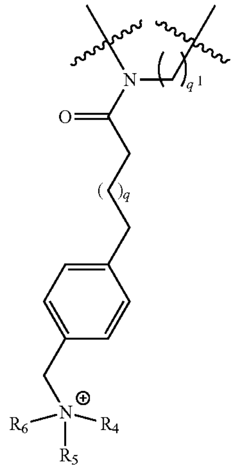

wherein $R_4$-$R_6$ are as described hereinabove;

q and $q^1$ are independently an integer between 0 and 16; and wherein said monomeric unit is chemically bound to the surface of an inorganic core directly or via a third linker (L6).

In another embodiment, a linker molecule which may be used in the processes of preparing the anti-microbial particles of this invention is represented by the structure of formula IH1 or IH2:

(IH1)

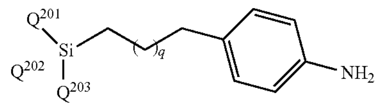

(IH2)

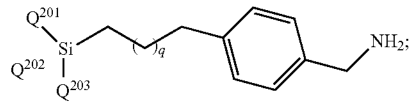

; or wherein $Q^{201}$, $Q^{202}$ and $Q^{203}$ are independently selected from the group consisting of alkoxy, methyl, ethyl, hydrogen, sulfonate and halide, wherein at least one of $Q^{201}$, $Q^{202}$ and $Q^{203}$ is selected from ethoxy, methoxy, sulfonate (e.g., mesyl, tosyl) and halide;

q is an integer between 0 and 16;

the linker molecule is capable of being chemically bound to the surface of the inorganic core through the silicon atom; and the anti-microbial active group is introduced by functionalizing the primary amine to obtain an anti-microbial active quaternary ammonium group as described above.

In another embodiment, a linker molecule which may be used in the processes of preparing the anti-microbial particles of this invention is represented by the structure of formula IJ:

(IJ)

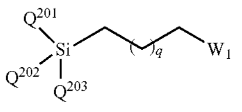

wherein $Q^{201}$, $Q^{202}$ and $Q^{203}$ are independently selected from the group consisting of alkoxy, methyl, ethyl, hydrogen, sulfonate and halide, wherein at least one of $Q^{201}$, $Q^{202}$ and $Q^{203}$ is selected from ethoxy, methoxy, sulfonate (e.g., mesyl, tosyl) and halide;

$W_1$ is selected from the group consisting of arylene-$NH_2$, benzylene-$NH_2$, halide, sulfonate and hydroxyl;

q is an integer between 0 and 16;

said linker is capable of being chemically bound to the surface of said inorganic core through the silicon atom; and the anti-microbial active group is introduced by substituting the group W with an anti-microbial active group, or converting the group W to an anti-microbial active group.

The particles of this invention demonstrate an enhanced anti-microbial activity. Without being bound by any theory or mechanism, it can be postulated that such activity originates from the presence of closely packed anti-microbial groups on a given core's surface, as well as high density of particles packed on the surface of a host material. This density increases as each anti-microbial active unit in the particles of this invention comprise increasing number of anti-microbial active groups and it yields a high local concentration of active functional groups, which results in high effective concentration of the anti-microbial active groups and enables the use of a relatively small amount of particles to achieve effective bacterial annihilation. The close packing of the anti-microbial groups is due to, inter alia, numerous anti-microbial active units protruding from each particle surface. Accordingly, the anti-microbial groups cover large fraction of the particle's available surface area (width dimension covering the surface). The surface density of the anti-microbial group results in high effective concentration promoting anti-microbial inhibitory effect. According to the principles of this invention, high surface density dictates high anti-microbial efficiency.

The term "nanoparticle" as used herein refers to a particle having a diameter of less than about 1,000 nm. The term "microparticle" as used herein refers to a particle having a diameter of about 1,000 nm or larger.

The anti-microbial particles of this invention are characterized by having a diameter between about 5 to about 100,000 nm, and thus encompass both nanoparticulate and microparticulate compositions. Preferred are particles between about 10 to about 50,000 nm. In other embodiments, the particles are more than 1,000 nm in diameter. In other embodiments, the particles are more than 10,000 nm in diameter. In other embodiment, the particles are between 1,000 and 50,000 nm in diameter. In other embodiment, the particles are between 5 and 250 nm in diameter. In other embodiment, the particles are between 5 and 500 nm in diameter. In another embodiment, the particles are between 5 and 1000 nm in diameter. It is apparent to a person of skill in the art that other particles size ranges are applicable and are encompassed within the scope of this invention.

Anti-Microbial Active Groups Comprising Terpenoid Groups

In one embodiment, the anti-microbial active group of this invention contains at least one terpenoid group. In another embodiment, the anti-microbial active group is selected from: (a) a tertiary amine ($R_3$ and/or $R_3'$ is nothing) or tertiary ammonium ($R_3$ and/or $R_3'$ is H) comprising at least one terpenoid moiety; and (b) a quaternary ammonium group comprising at least one terpenoid moiety. In another embodiment, when the anti-microbial active group of this invention contains at least one terpenoid group and/or $R_1$, $R_2$, $R_3$ and/or $R_1'$, $R_2'$, $R_3'$ of the anti-microbial active groups as defined hereinabove are terpenoid moieties—the core of the particles of this invention is a polyhedral oligomeric silsesquioxane (POSS).

In some embodiments, the anti-microbial active group of formula (1) to (6) is selected from: (a) a tertiary amine ($R_3$ and/or $R_3'$ is nothing) or tertiary ammonium ($R_3$ and/or $R_3'$ is H), wherein the nitrogen atom of each tertiary amine/ammonium having at least one bond to $X_1$ or $X_2$ and one bond to a terpenoid moiety; (b) a tertiary amine ($R_3$ and/or $R_3'$ is nothing), or tertiary ammonium ($R_3$ and/or $R_3'$ is H), the nitrogen atom of each tertiary amine/ammonium having one bond to $X_1$ or $X_2$ and two bonds to terpenoid moieties which may be the same or different from each other, or a salt of said tertiary amine; (c) a quaternary ammonium group the nitrogen atom of each quaternary ammonium group having at least one bond to $X_1$ or $X_2$ and one or two bonds to terpenoid moieties which may be the same or different from each other; Each possibility represents a separate embodiment of this invention.

In one embodiment, $R_6$, $R_8$-$R_{11}$, $R_6'$ and/or $R_{8'}$-$R_{11}$, of the anti-microbial active groups [—$^+N(R_4)(R_5)(R_6)$, —$^+N(R_4')(R_5')(R_6')$,

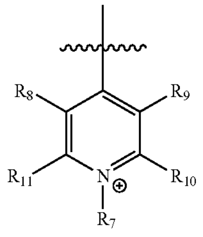 or 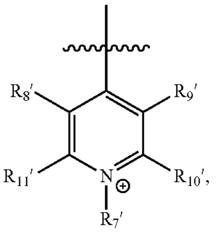

defined in structures (I) and (IE)] are the terpenoid moieties.

In another embodiment, when the anti-microbial active group of this invention contains at least one terpenoid group and/or $R_6$, $R_8$-$R_{11}$, $R_6$, and/or $R_8'$-$R_{11}'$ of the anti-microbial active groups as defined hereinabove are terpenoid moieties—the core of the particles of this invention is a polyhedral oligomeric silsesquioxane (POSS).

The term "terpenoid", also known as "isoprenoid" refers to a large class of naturally occurring compounds that are derived from five-carbon isoprene units. A “terpenoid moiety” is derived from a terpenoid.

In some embodiments, the terpenoid moiety is a “terpenoidyl”, i.e. directly bonded to one group (e.g. cinnamyl:

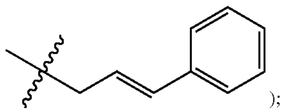 [SMILES: *C/C=C/c1ccccc1]

);

or a “terpenoidylene”, i.e. directly bonded to two groups (e.g. cinnamylene, e.g.

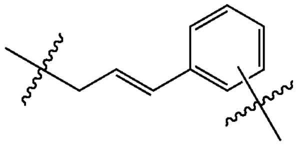

).

In one embodiment, the terpenoid moiety is directly bonded to more than two groups. In one embodiment, the terpenoid moiety is a cinammyl or cinnamylene group derived from cinnamaldehyde, cinnamic acid, curcumin, viscidone or cinnamyl alcohol. In another embodiment, the terpenoid moiety is a bornyl or a bornylene group derived from camphor, bornyl halide or bornyl alcohol. In another embodiment, the terpenoid moiety is derived from citral. In another embodiment, the terpenoid moiety is derived from perilaldehyde. Each possibility represents a separate embodiment of this invention.

Cinnamaldehyde is a natural aldehyde extracted from the genus *Cinnamomum*. It is known for its low toxicity and its effectiveness against various bacteria and fungi.

Camphor is found in the wood of the camphor laurel (*Cinnamomum camphora*), and also of the kapur tree. It also occurs in some other related trees in the laurel family, for example *Ocotea usambarensis*, as well as other natural sources. Camphor can also be synthetically produced from oil of turpentine. Camphor can be found as an R or S enantiomer, a mixture of enantiomers and a racemic mixture. Each possibility represents a separate embodiment of this invention.

Citral, or 3,7-dimethyl-2,6-octadienal or lemonal, is a mixture of two diastereomeric terpenoids. The two compounds are double bond isomers. The E-isomer is known as geranial or citral A. The Z-isomer is known as neral or citral B. Citral is known to have anti-microbial activity.

Perillaldehyde, also known as perilla aldehyde, is a natural terpenoid found most in the annual herb perilla, as well as in a wide variety of other plants and essential oils.

Other examples of terpenoids include, but are not limited to: curcuminoids found in turmeric and mustard seed, citronellal found in Cymbopogon (lemon grass) and carvacrol, found in *Origanum vulgare* (oregano), thyme, pepperwort, wild bergamot and *Lippia graveolens*. Each possibility represents a separate embodiment of this invention.

In accordance with the above embodiment, the anti-microbial active terpenoid moieties are selected from the group consisting of:

(i)

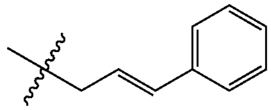

;

(ii)

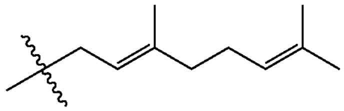

;

(iii)

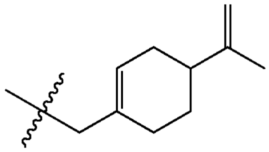

;

(iv)

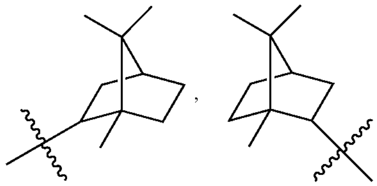

or any combination thereof;

(v)

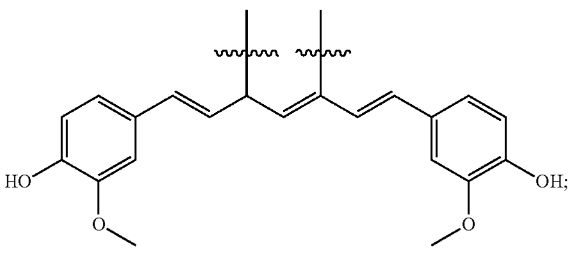

;

(vi)

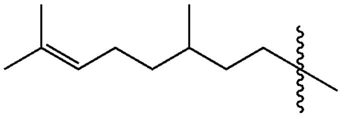

; and (vii)

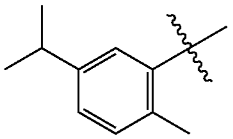

.

Each possibility represents a separate embodiment of this invention.

Non-limiting examples of anti-microbial active quaternary ammonium groups in accordance with the principles of this invention are:

-continued
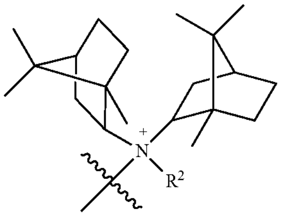
;
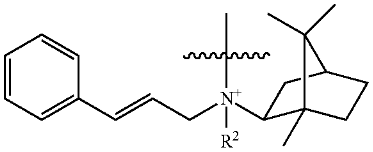
;
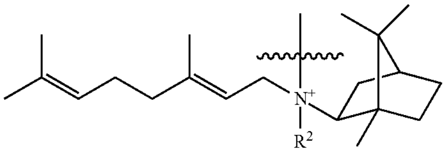
;
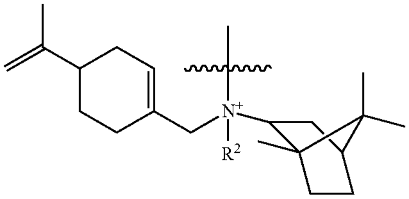
;
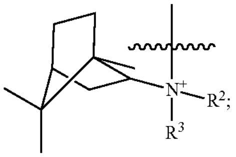
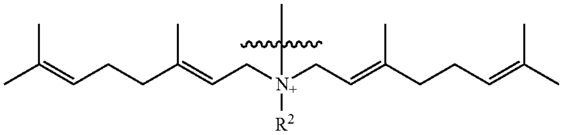
;
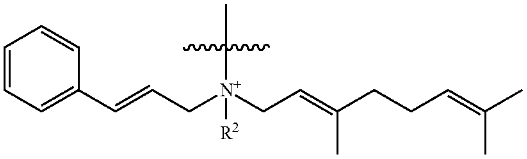
;
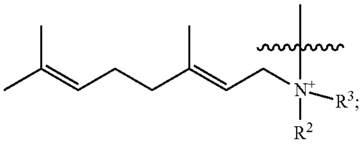
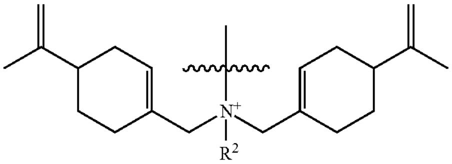
;
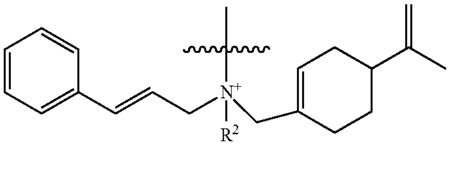
;
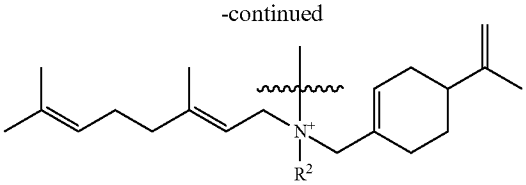
;
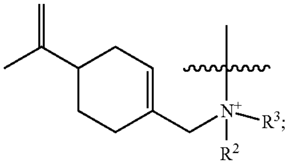
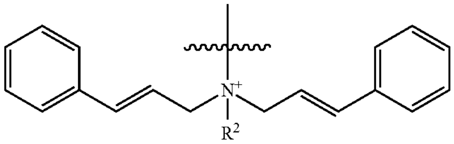
;
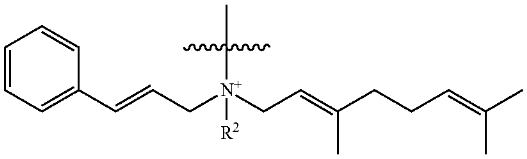
;
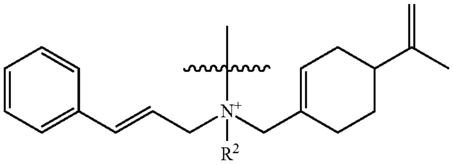
;
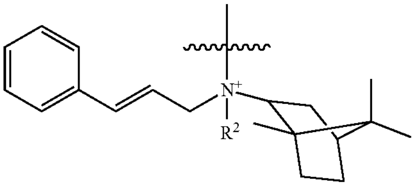
;
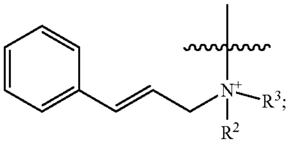
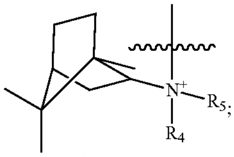
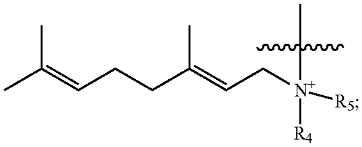
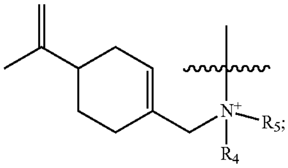
and
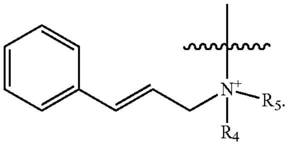
wherein
$R^2$ is alkyl, terpenoid, cycloalkyl, aryl, heterocycle, alkenyl, alkynyl or any combination thereof;
$R^3$ is alkyl, terpenoid moiety, cycloalkyl, aryl, heterocycle, alkenyl, alkynyl or any combination thereof;

$R_4$ and $R_5$ are independently methyl, $CF_3$, perhaloalkyl, aryl, benzyl, 2,2-disubstituted $C_3$-$C_{20}$ alkyl, 2,2,2-trisubstituted ethyl, $—CH_2C(=O)OR$, $—CH_2C(=O)OC(=O)R$, $—CH_2C(=S)OR$, $—CH_2C(=O)SR$, $—C(=O)OR$, $—C(=O)OC(=O)R$, $—C(=S)OR$, $—C(=O)SR$, $—C(=O)—R$, $—C(=S)—R$, $—CH_2C(=O)R$, $—CH_2C(=S)R$, $—CH_2CF_3$, $—CH_2NO_2$, 1-alkenyl, 1-alkynyl, 2-alkenyl, 2-alkynyl or any combination thereof; and R is alkyl, aryl, cycloalkyl, heterocycle or any combination thereof.

Non-limiting examples of functional anti-microbial active tertiary amine groups or its protonated form in accordance with the principles of this invention are:

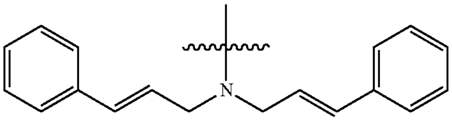
;

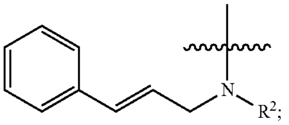

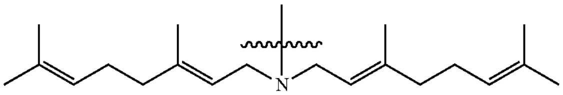
;

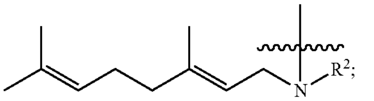

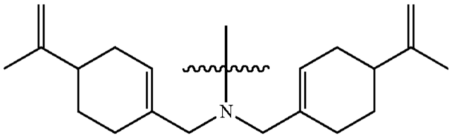
;

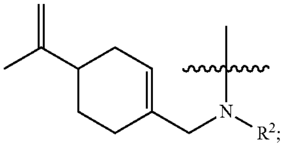

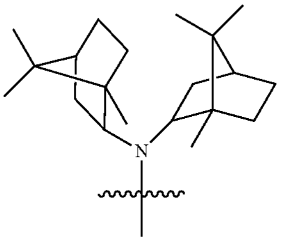
;

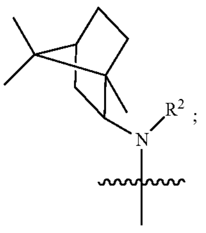

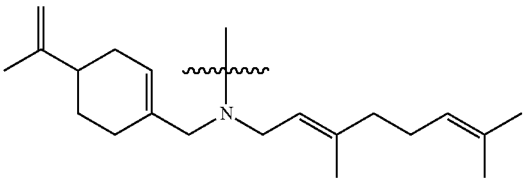
;

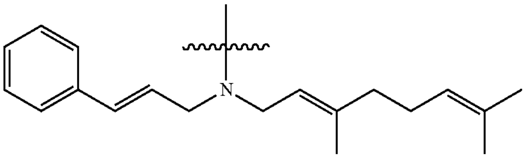
;

-continued

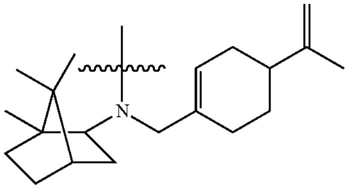
;

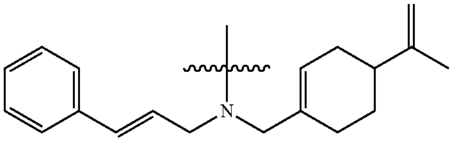
;

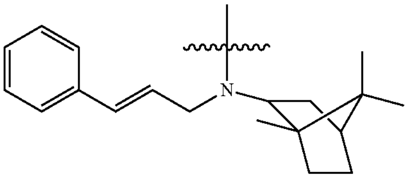
; and

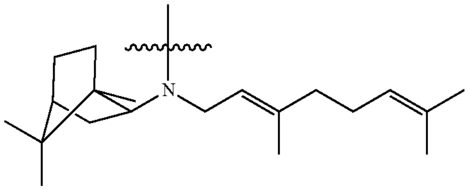
.

wherein $R^2$ is alkyl, terpenoid, cycloalkyl, aryl, heterocycle, alkenyl, alkynyl or any combination thereof.

The anti-microbial active group of this invention may be in the form of a quaternary ammonium or pyridinium salt, as described hereinabove. Since an such groups are positively charged, their charge is balanced with an anion. Non-limiting examples of anions include: a halide, e.g. fluoride, chloride, bromide or iodide and fluoride, bicarbonate, nitrate, phosphate, acetate, fumarate, succinate, mesylate, triflate, tosylate, tetrafluoroborate, hexafluorophosphate and sulfate. Each possibility represents a separate embodiment of this invention.

Anti-Microbial Active Groups Comprising One Long Alkyl Group.

In one embodiment, the anti-microbial active group of this invention contains one alkyl group which have from 4 to 24 carbon atoms as $R_8$-$R_{11}$ and/or $R_{8'}$-$R_{11'}$ of the anti-microbial active groups [

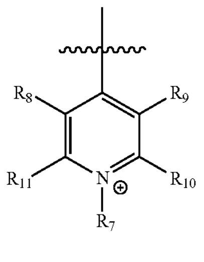
or
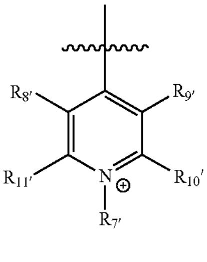
, defined in structures (I) and (IE)].

The term "quaternary ammonium group" refers to a group of atoms consisting of a nitrogen atom with four substituents (different than hydrogen) attached thereto. In another embodiment, a "quaternary ammonium group" refers to a group of atoms consisting of a nitrogen atom with four groups wherein each of the group is attached to the nitrogen through a carbon atom. The term "long alkyl group" or chain refers to such an alkyl group or chain which is substituted on the nitrogen atom of the quaternary ammonium group or found as substituent to the pyridinium and which has between 4 and 24 carbon atoms. In some currently preferred embodiments, the alkyl group is an alkyl group having 4 to 18 carbon atoms. In some currently preferred embodiments, the alkyl group is an alkyl group having 4 to 8 carbon atoms. In some currently preferred embodiments, the alkyl group is an alkyl group having 4 to 10 carbon atoms. In other currently preferred embodiments, the alkyl group is an alkyl group having 6, 7, or 8 carbon atoms, with each possibility representing a separate embodiment of this invention.

Organic Polymeric Cores

In some embodiments, the core of the anti-microbial particles is an organic polymeric core. In one embodiment, the organic core comprises at least one aliphatic polymer. An “aliphatic polymer” as used within the scope of this invention refers to a polymer made of aliphatic monomers that may be substituted with various side groups, including (but not restricted to) aromatic side groups. Aliphatic polymers that may be included in particles according to this invention comprise nitrogen atoms (as well as other heteroatoms) as part of the polymeric backbone. In one embodiment, the core of the particles is an organic polymeric core including an amine which can be substituted with $R_1$, $R_2$ and/or $R_3$ as defined for structure 1; or including an imine which is chemically modified to amine and then substituted with $R_1$, $R_2$ and/or $R_3$ as defined for structure 1. In one embodiment, the core of the particles is an organic polymeric core including amines which can be substituted with $R_4$, $R_5$, $R_6$, $R_{4'}$, $R_{5'}$ and/or $R_{6'}$ as defined for structure 1; or including an imine which is chemically modified to amine and then substituted with $R_4$, $R_5$, $R_6$, $R_{4'}$, $R_{5'}$ and/or $R_{6'}$ as defined for structure 1. Non-limiting examples of aliphatic polymers are polystyrene (PS), polyvinylchloride (PVC), polyethylene imine (PEI), polyvinyl amine (PVA), poly(allyl amine) (PAA), poly(aminoethyl acrylate), polypeptides with pending alkyl-amino groups, and chitosan. Each possibility represents a separate embodiment of this invention. In one currently preferred embodiment, the polymer is polyethylene imine (PEI).

In another embodiment, the organic core comprises at least one aromatic polymer selected from the following group: polystyrene, aminomethylated styrene polymers, aromatic polyesters, preferably polyethylene terephthalate, and polyvinyl pyridine.

In another embodiment, the polymeric core may be linked to anti-microbial active part directly (i.e. in structures (1)-(3): $L_3$ is a bond) or via a linker. In another embodiment, the polymeric core may be linked to anti-microbial active part directly (i.e. in structures (I), (IE) and (II)-(VII): $L_6$ is a bond) or via a linker. Each possibility represents a separate embodiment of this invention.

In one embodiment, the organic polymeric core includes a combination of two or more different organic polymers. In another embodiment, the organic polymeric core includes a copolymer.

In some embodiments, anti-microbial active unit is linked to the organic polymeric core directly ($L_3$ or $L_6$ is a bond) or via a linker ($L_3$ or $L_6$). In these embodiments, the linker may be selected from:

(a) a C1 to C18 alkylene substituted with at least one carboxyl moiety. This linker may be derived from an alkylene substituted with at least one carboxyl moiety and at least one amino moiety, wherein the carboxyl end is attached to the core and the amino end is modified to anti-microbial active group [$—^+N(R_1)(R_2)(R_3)$, $—^+NH(R_1)(R_2)$, $—N(R_1)(R_2)—^+N(R_1')(R_2')(R_3')$, $—^+NH(R_1')(R_2')$ or $—N(R_1')(R_2')$ (defined in structures (1) to (6); or $—^+N(R_4)(R_5)(R_6)$, $—^+N(R_4')(R_5')(R_6')$,

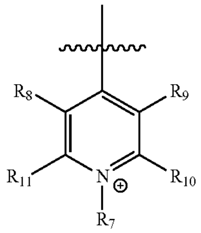

or

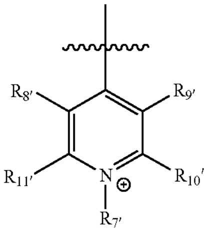

, defined in structures (I) and (IE)]. This linker may be derived from an amino acid of natural or synthetic source having a chain length of between 2 and 18 carbon atoms, or an acyl halide of said amino acid. Non-limiting examples for such amino acids are 18-amino octadecanoic acid and 18-amino stearic acid;

(b) a C1 to C18 alkylene. This linker may be derived from a di-halo alkylene, which is functionalized at each end with the core and anti-microbial active group, respectively, by replacement of the halogen moiety to a functional group that will bind to the core and replacement of the halogen moiety to obtain [$—^+N(R_1)(R_2)(R_3)$, $—^+NH(R_1)(R_2)$, $—N(R_1)(R_2)—^+N(R_1')(R_2')(R_3')$, $—^+NH(R_1')(R_2')$ or $—N(R_1')(R_2')$ (defined in structures (1) to (6); or $—^+N(R_4)(R_5)(R_6)$ or $—^+N(R_4')(R_5')(R_6')$, defined in structures (I) and (IE)]; and (c) aromatic molecules derived from 4,4-biphenol, dibenzoic acid, dibenzoic halides, dibenzoic sulphonates, terephthalic acid, terephthalic halides, and terephthalic sulphonates. This linker is functionalized with the core and anti-microbial active group, respectively, through the functional group thereof (i.e., hydroxyl, carboxy or sulfonate). In another embodiment, this linker is attached to the core at one end and is modified at the other end to anti-microbial active group [$—^+N(R_1)(R_2)(R_3)$, $—^+NH(R_1)(R_2)$, $—N(R_1)(R_2)—^+N(R_1')(R_2')(R_3')$, $—^+NH(R_1')(R_2')$ or $—N(R_1')(R_2')$ (defined in structures (1) to (6); or $—^+N(R_4)(R_5)(R_6)$, $—^+N(R_4')(R_5')(R_6')$,

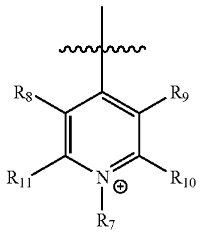

or

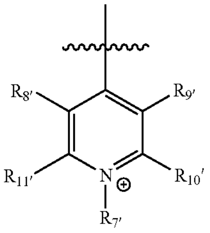

, defined in structures (I) and (IE)]. In another embodiment, the linker comprises alkyl, alkenyl, alkyl phosphate, alkyl siloxanes, carboxylate, epoxy, acylhalides and anhydrides, or combination thereof, wherein the functional group is attached to the core. Each possibility represents a separate embodiment of this invention.

Various polymeric chains may provide a range of properties that themselves may be an accumulation of the various polymer properties, and may even provide unexpected synergistic properties. Examples of such mixed polyamine particles include: crosslinking of aliphatic and aromatic polyamines such as polyethyleneimine and poly(4-vinyl pyridine) via a dihaloalkane; mixture of linear short chain and branched high molecular weight polyethyleneimines; interpenetrating compositions of polyamine within a polyamine scaffold such as polyethyleneimine embedded within crosslinked polyvinyl pyridine particles, or even interpenetrating a polyamine into a low density non-amine scaffold such as polystyrene particles. In other words, the use of polyamine combinations for the purpose of forming particles, either by chemical crosslinking or physical cross-linking (interpenetrating networks) may afford structures of varying properties (such as being able to better kill one bacteria vs. another type of bacteria). Such properties may be additive or synergistic in nature.

In one specific embodiment, the organic polymeric core is cross-linked with a cross-linking agent. The preferred degree of cross-linking is from 1% to 20%, when crosslinking of from about 2% to about 5% is preferable. The crosslinking may prevent unfolding of the polymer and separation of the various polymeric chains that form the particle.

Crosslinking, as may be known to a person skilled in the art of organic synthesis and polymer science, may be affected by various agents and reactions that are per se known in the art. For example, crosslinking may be affected by alkylating the polymer chains with dihaloalkane such as dibromoethane, dibromocyclohexane, or bis-bromomethylbenzene. Alternatively, crosslinking by reductive amination may be used. In this method a polyamine with primary amines is reacted with a diketone or with an alkane dialdehyde to form an imine crosslinker which is then further hydrogenated to the corresponding amine. This amine is further reacted to form an antimicrobial effective quaternary ammonium group. In such a method, instead of dihaloalkanes or dialdehydes, tri or polyhaloalkanes or polyaldehydes or polyketones are used.

The preferred polymers useful for making the polymeric core according to this invention are those having chains made of 30 monomer units, preferably 100 monomer units that may be crosslinked using less than 10% of crosslinking agent. The longer the polymers are, the fewer crosslinking bonds are needed to afford an insoluble core. Branched polymers are preferred for crosslinking as small amount of crosslinking is required to form insoluble core.

In some embodiments, at least about 10% of the amine groups in the organic polymeric core are the anti-microbial active tertiary amine/ammonium or quaternary ammonium groups or salts thereof, as described herein.

In one embodiment, the anti-microbial particles according to this invention have functional groups that are capable of reacting with a host polymer or with monomers thereof. Such functional groups are designed to allow the particles to be bound chemically to a hosting material.

Inorganic Cores

In some embodiments, the core of the anti-microbial particles of this invention is an inorganic core comprising one or more inorganic materials. Inorganic cores have a few advantages over organic polymeric cores: 1) higher stability at elevated temperature; 2) higher chemical stability towards various solvent and reagents; 3) improved mechanical strength; 4) better handling qualities in composites due to their amphipathic nature; and 5) lower cost.

An additional advantage of inorganic cores relates to the insertion of the functionalized particles into a polymeric material within a polymeric matrix (host). In contrast to organic cores which are produced by radical polymerization (e.g. acrylate resins), inorganic cores do not interfere with the polymerization process and hence do not jeopardize the mechanical properties of the finalized substrate, as opposed to organic polymeric cores which tend to interfere with the polymerization reaction. silica dioxide, glass powder, ceramics or polymer material In one embodiment, the inorganic core comprises silica, glass, glass powder, metal, metal oxide, ceramic material or a zeolite. Each possibility represents a separate embodiment of this invention.

In one embodiment, the core of the particles of this invention comprises silica ($SiO_2$). The silica may be in any form known in the art, non-limiting examples of which include polyhedral oligomeric silsesquioxane (POSS), amorphous silica, dense silica, aerogel silica, porous silica, mesoporous silica and fumed silica.

The surface density of active groups onto particle surface have proportional impact on its anti-microbial activity. This is applicable both to organic and inorganic particles in same manner. In another embodiment, the core of the particles of this invention comprises glasses or ceramics of silicate ($SiO_4^{-4}$). Non-limiting examples of silicates include aluminosilicate, borosilicate, barium silicate, barium borosilicate and strontium borosilicate.

In another embodiment, the core of the particles of this invention comprises surface activated metals selected from the group of: silver, gold, platinum, palladium, copper, zinc and iron.

In another embodiment, the core of the particles of this invention comprises metal oxides selected from the group of: zirconium dioxide, titanium dioxide, vanadium dioxide, zinc oxide, copper oxide and magnetite.

The inorganic core typically has a solid uniform morphology with low porosity or a porous morphology having pore size diameter of between about 1 to about 30 nm.

In another embodiment, the core of the particles of this invention comprises natural or artificial Zeolites.

In one embodiment, non-limiting examples of ceramic materials include: oxides (e.g. zinc oxide, boron oxide, zirconium oxide), carbides (e.g. silicon carbide, titanium carbide), nitrides (e.g. titanium nitride, boron nitride) and borides (e.g. magnesium diboride)

In one embodiment, the core may be attached to the anti-microbial unit directly (i.e. in structures (1)-(3): $L_3$ is a bond or in structures (I), (IE) and (II)-(VII): $L_6$ is a bond), or via a linker ($L_3$ or $L_6$). Preferably a silica ($SiO_2$) based inorganic core may be attached to the anti-microbial part through a linker ($L_3$ or $L_6$), while glasses or ceramicas of silicate ($SiO_4$-4), metals or metal oxides may be attached to anti-microbial unit directly (i.e. in structures (1)-(3): $L_3$ is a bond or in structures (I), (IE) and (II)-(VII): $L_6$ is a bond).

In some embodiments, the inorganic core is directly (i.e. in structures (1)-(3): $L_3$ is a bond or in structures (I), (IE) and (II)-(VII): $L_6$ is a bond) attached to the anti-microbial unit. In other embodiments, the inorganic core is attached to the anti-microbial unit through a linker. In some embodiments, the linker is selected from the following groups: a C1 to C18 alkylene; a C1 to C18 alkylene substituted with at least one silane or alkoxysilane moiety; a C1 to C18 alkylene substituted with at least one phosphate moiety; a C1 to C18 alkylene substituted with at least one anhydride moiety; a C1 to C18 alkylene substituted with at least one carboxylate moiety; and a C1 to C18 alkylene substituted with at least one glycidyl moiety. Each possibility represents a separate embodiment of this invention.

The inorganic core of the particle as described above may generally be in a form selected from a sphere, amorphous polygonal, shallow flake-like and a rod. In some representative embodiments, the inorganic core is spherical and has a diameter between about 5 to about 100,000 nm. In some representative embodiments, the inorganic core is spherical and has a diameter between about 1000-100,000 nm. In some representative embodiments, the inorganic core is spherical and has a diameter between about 100-1000 nm with pore diameter of about 1 to about 100 nm. In another embodiment, the inorganic spherical core has a pore diameter of about 1 to about 50 nm. In another embodiment, the inorganic spherical core has a pore diameter of about 1 to about 30 nm. In another embodiment, the inorganic particle is in a form of a rod, having a diameter of between about 5 to about 1,000 nm and length between about 10 to about 1,000,000 nm. In another embodiment, a length of between 50 to 100,000 nm. In another embodiment, a length of between 100 to 250,000 nm. In another embodiment, a length of between 200 to 500,000 and a pore diameter of about 1 to about 50 nm. Each possibility represents a separate embodiment of this invention.

Processes of Preparing the Anti-Microbial Particles

Preparation of Anti-Microbial Particles, Comprising One Monomeric Unit Per One Anti-Microbial Active Part The particles of this invention may be prepared in accordance to a variety of processes, depending on the nature of the core, the anti-microbial active group, and the presence or absence of linkers. Some non-limiting examples of preparation methods are provided below.

In one embodiment, this invention provides processes for preparing anti-microbial particles, wherein the particles comprise one monomeric unit per one anti-microbial active unit. In the following, such processes will be presented in detail.

Figure 2:
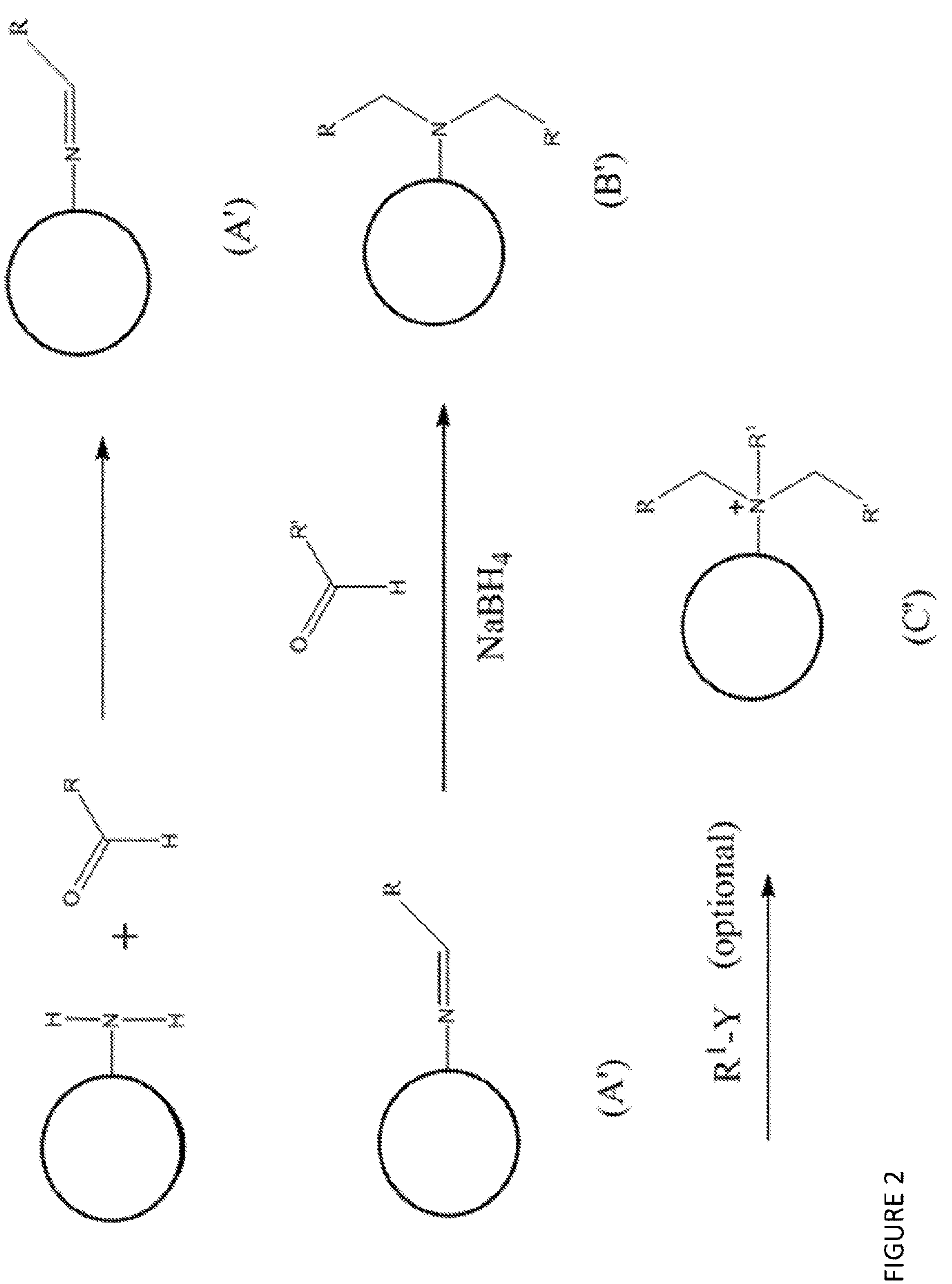
FIG. 2 depicts a representative scheme for the preparation of standard particles according to this invention wherein the anti-microbial active group is a tertiary amine or a quaternary ammonium group comprising at least one terpenoid moiety and the anti-microbial unit has one monomeric unit (a monomeric backbone, as presented in FIG. 1B); the circles represent the organic or inorganic core; and $R^1$—Y—$R^1$ is a $C_1$-$C_4$ alkyl and Y is a leaving group such as halogen or sulfonate.

A representative method for preparing particles according to this invention wherein the anti-microbial active group is a tertiary amine or a quaternary ammonium group comprising at least one terpenoid moiety is represented in FIG. 2, for standard particles. In accordance with FIG. 2, a core as defined herein is functionalized with a primary amine. The primary amine reacts with an aldehyde to yield initially an imine (Schiff base) intermediate of formula (A'), which is then reacted with a second aldehyde under reductive amination conditions to yield a tertiary amine of formula (B'). RC(═O)H and R'C(═O)H each represent an aldehyde which is a terpenoid or which is derived from a terpenoid. RC(═O)H and R'C(═O)H may be the same or different from each other. Conversion of the tertiary amine to the quaternary ammonium group is optional, and involves reaction of the tertiary amine with a group $R^1$—Y wherein $R^1$ is a $C_1$-$C_4$ alkyl and Y is a leaving group such as halogen or sulfonate.

It is understood that the group

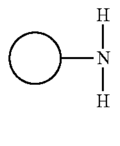

may represents any one or more of the following:

1. An organic core directly bound to $NH_2$.
2. An organic core bound to $NH_2$ through a linker as described herein.
3. An inorganic core directly bound to $NH_2$.
4. An inorganic core bound to $NH_2$ through a linker as described herein.

The exemplified reaction (FIG. 2) may be a "one pot synthesis", or it may include two sequential reactions with isolation of an intermediate formed in the first step. The first step is the formation of intermediate (A'), which is an imine (Schiff base), by reacting an amine functionalized core with a terpenoid moiety in the presence of a reducing agent, in this case cinnamyl in the presence of $NaBH_4$. The imine functionalized core can be isolated at this stage if desired. Alternatively, further reacting intermediate (A') with a terpenoid moiety in the presence of a reducing agent yields a tertiary amine comprising two terpenoid moieties (B'). In order to obtain the quaternary ammonium, additional alkylation step is performed as described in FIG. 2. Particles with enhanced thermal stability can be prepared in a similar fashion as described above and illustrated in FIG. 2 for standard particles, with a few notable differences: for standard particles R and R' are terpenoid moieties, where for particles with enhanced thermal stability, R and R' are each independently methyl, $CF_3$, perhaloalkyl, aryl, —C(═O)OR, —C(═O)OC(═O)R, —C(═S)OR, —C(═O)SR, —C(═O)—R, —C(═S)—R, 1-alkenyl or 1-alkynyl, where R is alkyl, aryl, cycloalkyl, heterocycle or any combination thereof; $R^1$ is a methyl, $CF_3$, perhaloalkyl, aryl, benzyl, 2,2-disubstituted $C_3$-$C_{20}$ alkyl, 2,2,2-trisubstituted ethyl, —$CH_2$C(═O)OR, —$CH_2$C(═O)OC(═O)R, —$CH_2$C(═S)OR, —$CH_2$C(═O)SR, —C(═O)OR, —C(═O)OC(═O)R, —C(═S)OR, —C(═O)SR, —C(═O)—R, —C(═S)—R, —$CH_2$C(═O)R, —$CH_2$C(═S)R, —$CH_2CF_3$, —$CH_2NO_2$, 1-alkenyl, 1-alkynyl, 2-alkenyl, 2-alkynyl or any combination thereof; where R is alkyl, aryl, cycloalkyl, heterocycle or any combination thereof. In this case of particles with enhanced thermal stability—the final reaction with $R^1$—Y is mandatory and not optional, in order to arrive at ammonium.

Figure 3:
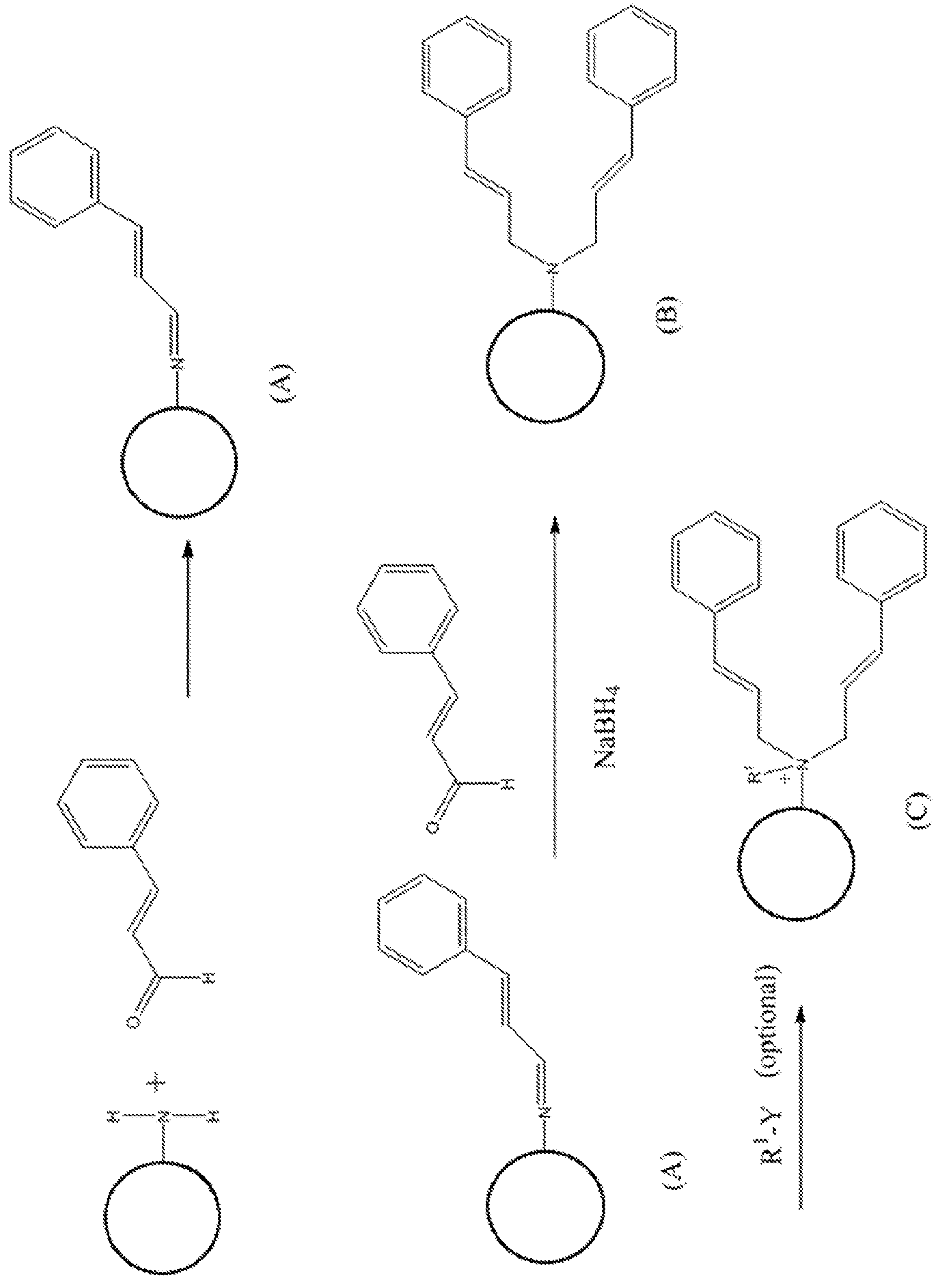
FIG. 3 depicts a representative scheme for the preparation of a standard particle of this invention having cinnamyl groups with a core (represented by a circle) via amino-functional linker wherein the anti-microbial unit has one monomeric unit (a monomeric backbone, as presented in FIG. 1B). Conversion of the tertiary amine to the quaternary ammonium group is optional, and involves reaction of the tertiary amine with a group $R^1$—Y wherein $R^1$ is a $C_1$-$C_4$ alkyl and Y is a leaving group such as halogen or sulfonate.

The process for the preparation of standard particles and presented in FIG. 3, uses cinnamaldehyde, but is applicable to other aldehydes. Thus, in some embodiments, this invention provides a particle comprising (i) an inorganic core or an organic polymeric core; and (ii) an imine moiety chemically bound to the core, preferably at a surface density of at least one imine group per 10 sq. nm, wherein the imine group comprises a terpenoid moiety. The imine moiety is generally represented by the structure of formula (B') in FIG. 2. A more specific embodiment is the structure of formula (B) in FIG. 3. It is understood by a person of skill in the art that other imine intermediate compounds comprising other terpenoids groups as described herein, are also encompassed by this invention.

Figure 4A:
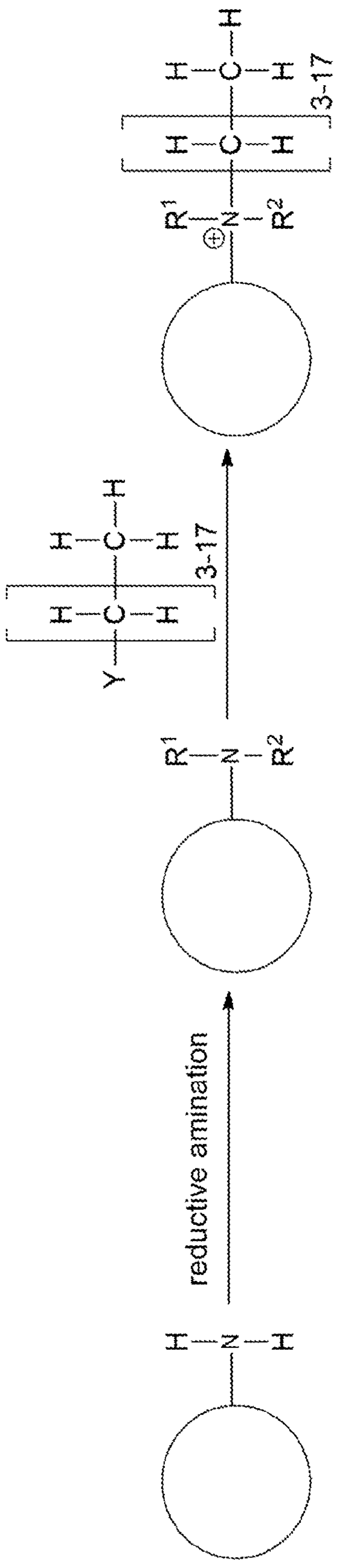
FIGS. 4A-4C depicts a representative scheme of three pathways for the preparation of quaternary ammonium salts (QAS) functionalized standard particle wherein the anti-microbial unit has one monomeric unit (a monomeric backbone, as presented in FIG. 1B); the circles represents organic or inorganic core.
Figure 4B:
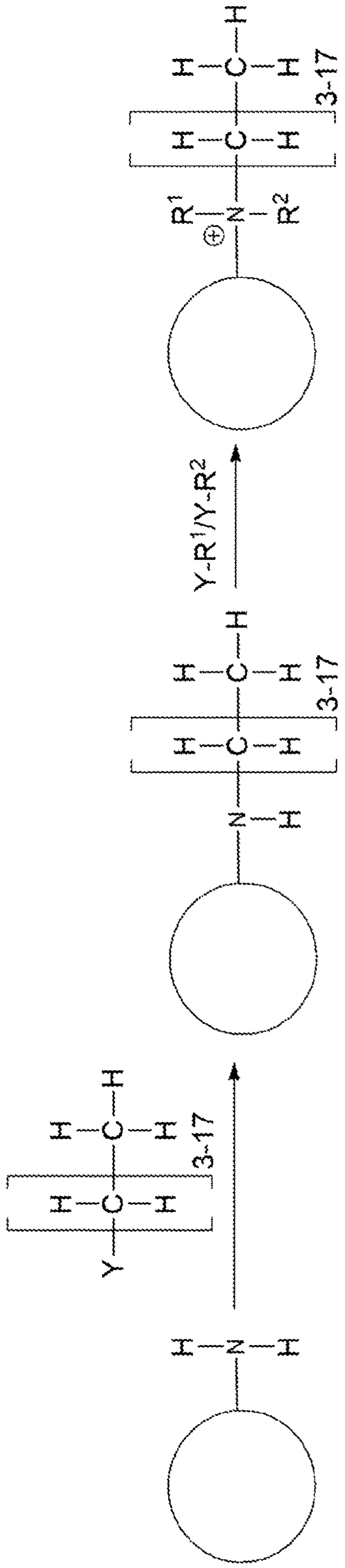
Figure 4C:
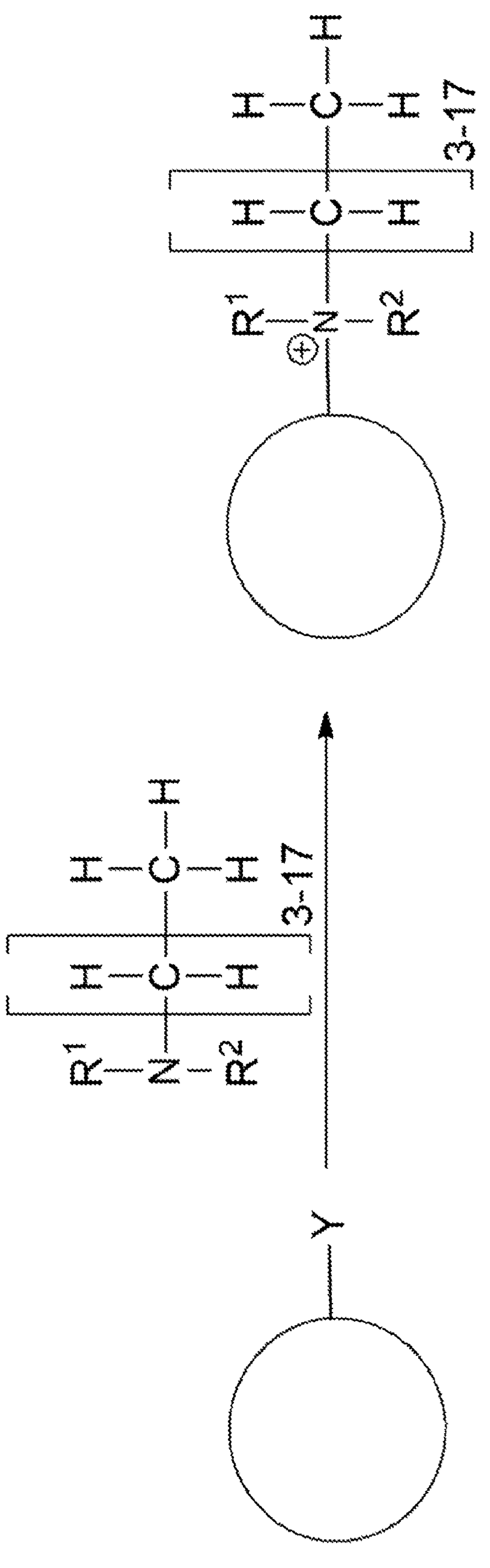

A representative method for preparing standard particles wherein the anti-microbial active group is a quaternary ammonium group containing one alkyl group having 4 to 18 carbon atoms is presented in FIGS. 4A-4C. The method includes three pathways to prepare quaternary ammonium salts (QAS) functionalized particle. FIG. 4A) by first utilizing reductive amination to achieve tertiary amine, followed by an alkylation reaction, FIG. 4B) by stepwise alkylation reactions; and FIG. 4C) by reacting a linker functionalized with a leaving group (e.g., Cl or other halogen) with tertiary amine. $R^1$ and $R^2$ represent $C_1$-$C_4$ alkyls such as methyl, ethyl, propyl or isopropyl. $R^1$ and $R^2$ may be different or the same group. Y represents any leaving group, for example Cl, Br or I, or a sulfonate (e.g., mesyl, tosyl).

It is understood that that the group

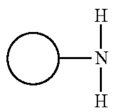

has any one of the meanings as described above for FIGS. 2 and 3.

It is understood that that the group

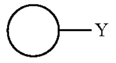

may represents any one or more of the following:

1. An organic core directly bound to Y.
2. An organic core bound to Y through a linker as described herein.
3. An inorganic core directly bound to Y.
4. An inorganic core bound to Y through a linker as described herein.

Figure 5A:
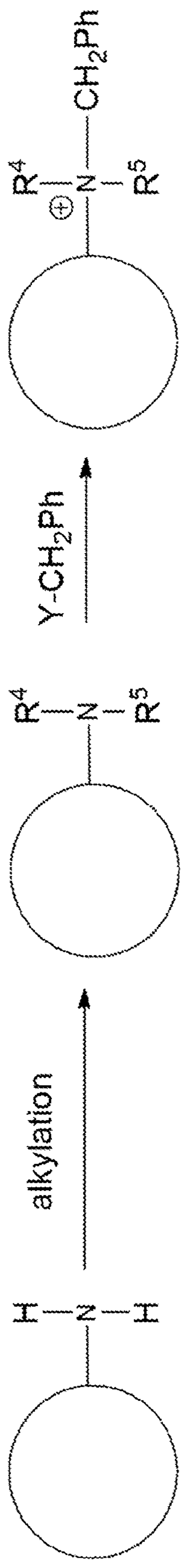
FIGS. 5A-5C depicts a representative scheme of three pathways for the preparation of quaternary ammonium salts (QAS) functionalized particle with enhanced thermal stability wherein the anti-microbial unit has one monomeric unit (a monomeric backbone, as presented in FIG. 1B); the circles represents organic or inorganic core.
Figure 5B:
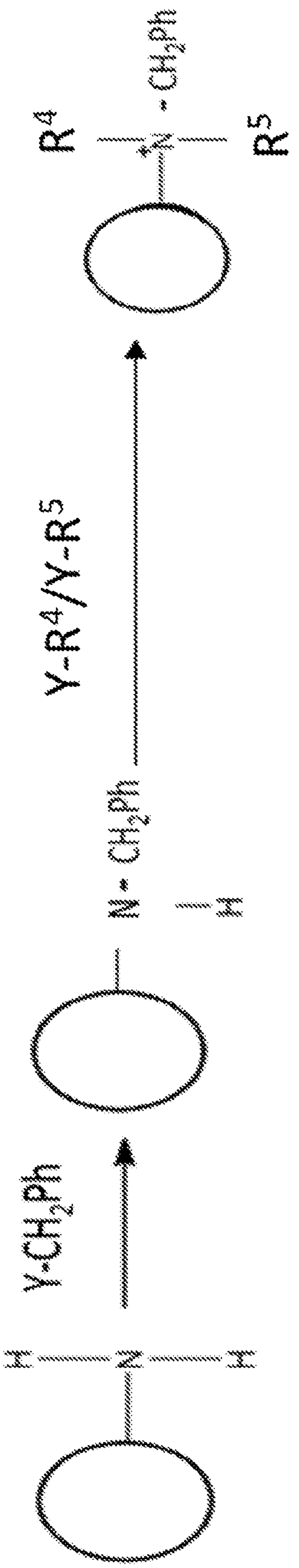
Figure 5C:
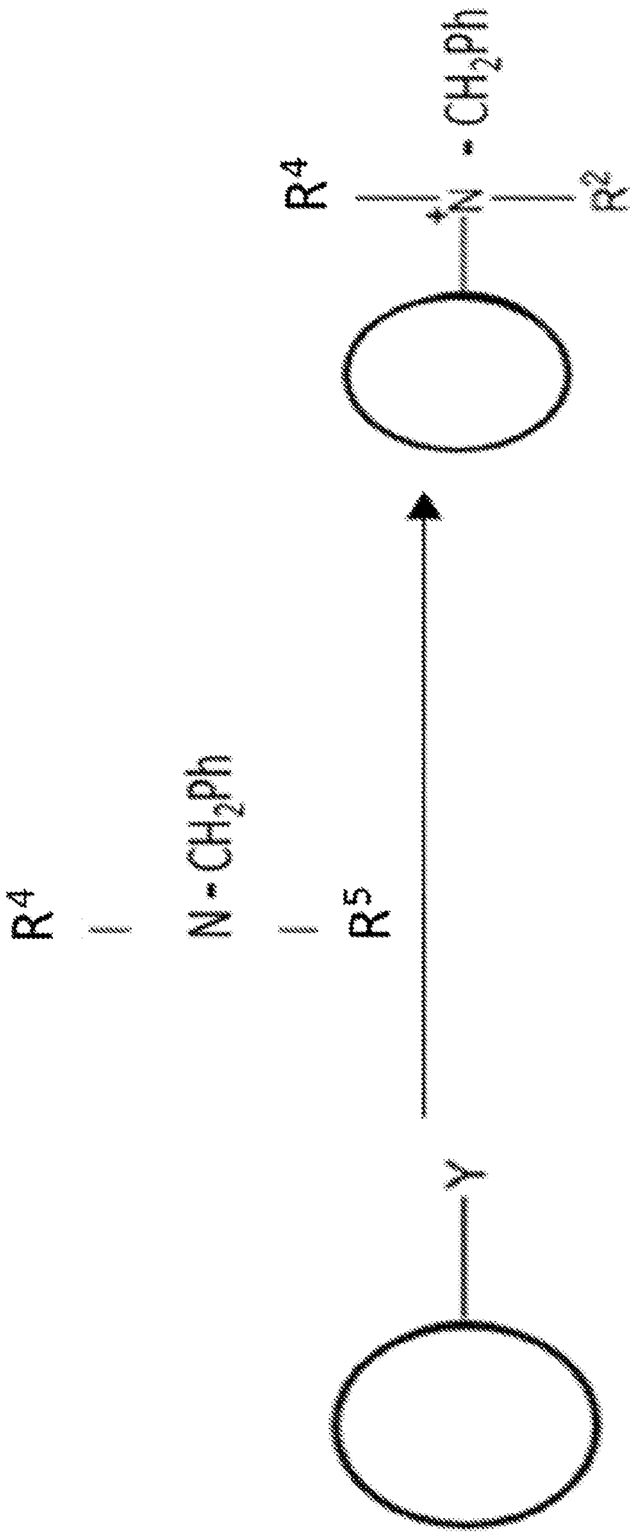

Similar method of preparing particles with enhanced thermal stability is represented in FIGS. 5A-5C. The method includes three pathways to prepare quaternary ammonium salts (QAS) functionalized particle. FIG. 5A) by reaction with $R_1$—Y/$R_2$—Y to achieve tertiary amine, followed by benzylation reaction; FIG. 5B) by a similar pathway as in FIG. 5A), done in the reversed order; and FIG. 5C): by reacting a linker functionalized with a leaving group (e.g., Cl or other halogen) with tertiary amine. $R_4$ and $R_5$ are independently methyl, $CF_3$, perhaloalkyl, aryl, benzyl, 2,2-disubstituted $C_3$-$C_{20}$ alkyl, 2,2,2-trisubstituted ethyl, —$CH_2C$(═O)OR, —$CH_2C$(═O)OC(═O)R, —$CH_2C$(═S)OR, —$CH_2C$(═O)SR, —C(═O)OR, —C(═O)OC(═O)R, —C(═S)OR, —C(═O)SR, —C(═O)—R, —C(═S)—R, —$CH_2C$(═O)R, —$CH_2C$(═S)R, —$CH_2CF_3$, —$CH_2NO_2$, 1-alkenyl, 1-alkynyl, 2-alkenyl, 2-alkynyl or any combination thereof. Y represents any leaving group, for example Cl, Br or I, or a sulfonate (e.g., mesyl, tosyl).

Figure 6:
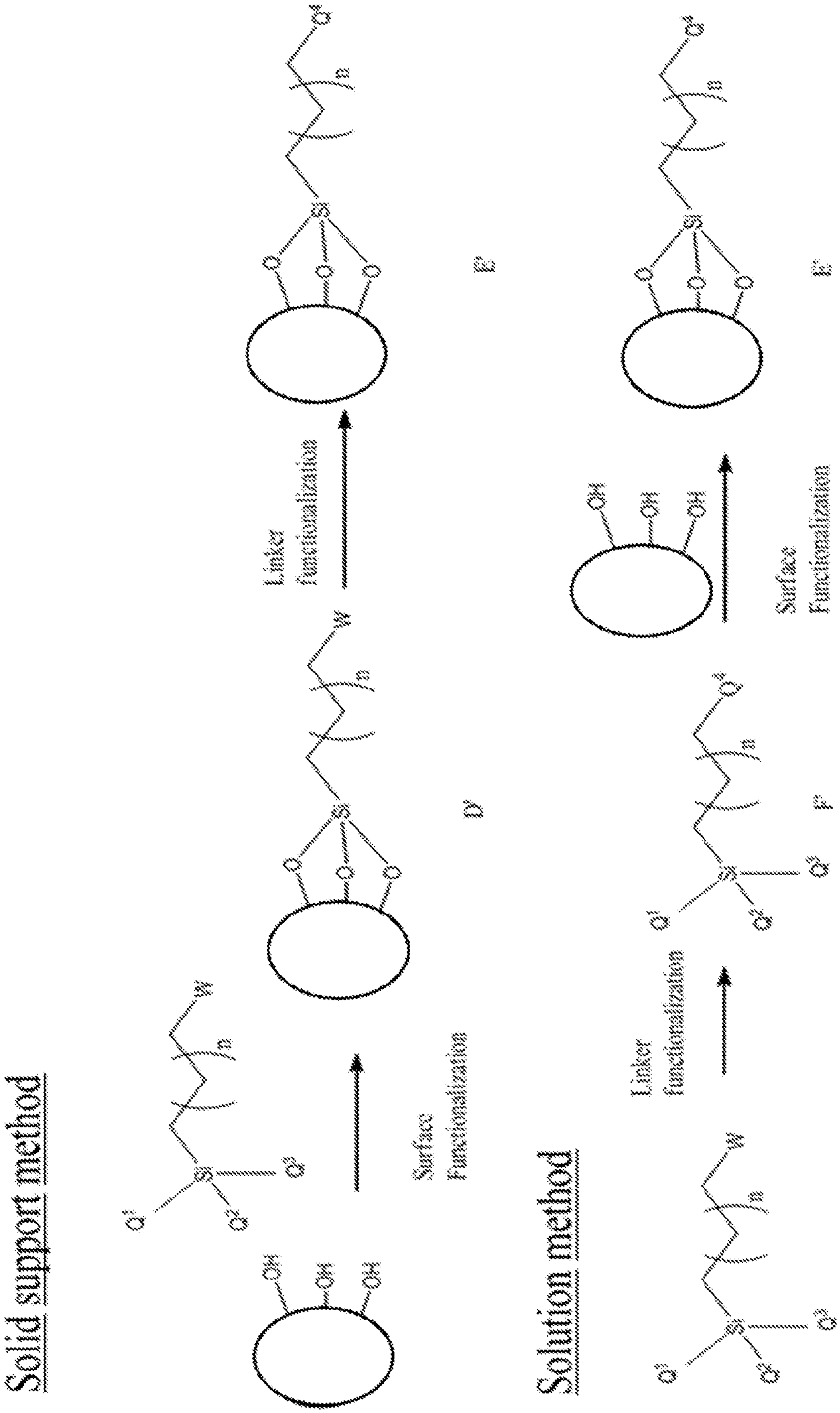
FIG. 6 depicts schemes of solid support and solution methods for the preparation of standard particles of this invention wherein the anti-microbial unit has one monomeric unit (a monomeric backbone, as presented in FIG. 1B). The circles represent an organic or inorganic core. $Q^1$, $Q^2$ and $Q^3$ are independently selected from the group consisting of ethoxy, methoxy, methyl, ethyl, hydrogen, sulfonate and halide, wherein at least one of $Q^1$, $Q^2$ and $Q^3$ is a leaving group selected from ethoxy, methoxy, sulfonate (e.g., mesyl, tosyl) and halide. For the sake of clarity the scheme presents a case where $Q^1$, $Q^2$ and $Q^3$ represent leaving groups; $Q^4$ represents an anti-microbial group; W is selected from the group consisting of $NH_2$, halide, sulfonate and hydroxyl; and n is an integer between 1 and 16.

Core functionalization can occur by a solid support method, or a solution method Solid Support as Method of Preparation of Anti-Microbial Particles Comprising One Monomeric Unit Per One Anti-Microbial Active Part Preparation of functionalized standard particles is conducted in two general steps. First, the linker molecule is allowed to condense onto particles surface (surface functionalization) via hydrolysis of leaving groups to give an intermediate of formula (FIG. 6, D'). Second, functional sites of the linker molecule undergo further functionalization (linker functionalization) as mentioned in any ones of (FIGS. 2-5) to give a functionalized particle of formula E' of FIG. 6. The circles in FIG. 6 represent an organic or inorganic core; $Q^1$, $Q^2$ and $Q^3$ are independently selected from the group consisting of ethoxy, methoxy, methyl, ethyl, hydrogen, sulfonate and halide, wherein at least one of $Q^1$, $Q^2$ and $Q^3$ is a leaving group selected from ethoxy, methoxy, sulfonate (e.g., mesyl, tosyl) and halide; W is selected from the group consisting of $NH_2$, halide, sulfonate and hydroxyl; and n is an integer between 1 and 16. For the sake of clarity the scheme presents a case where $Q^1$, $Q^2$ and $Q^3$ represent leaving groups; $Q^4$ represents an anti-microbial group. Similar process is used for the preparation of functionalized particles with enhanced thermal stability with the difference that W accommodates the same substituents with the exception that the $NH_2$ moiety is replaced with an arylene-$NH_2$ or benzylene-$NH_2$ moiety.

Solution Method as Method of Preparation of Anti-Microbial Particles Comprising One Monomeric Unit Per One Anti-Microbial Active Part In this method, the linker molecule is first functionalized with antimicrobial active group to give an intermediate of formula (FIG. 6, F'). In the second stage intermediate (F') is allowed to settle onto particle's solid surface (surface functionalization) to give a functionalized particle of formula (FIG. 6, E').

Figure 7:
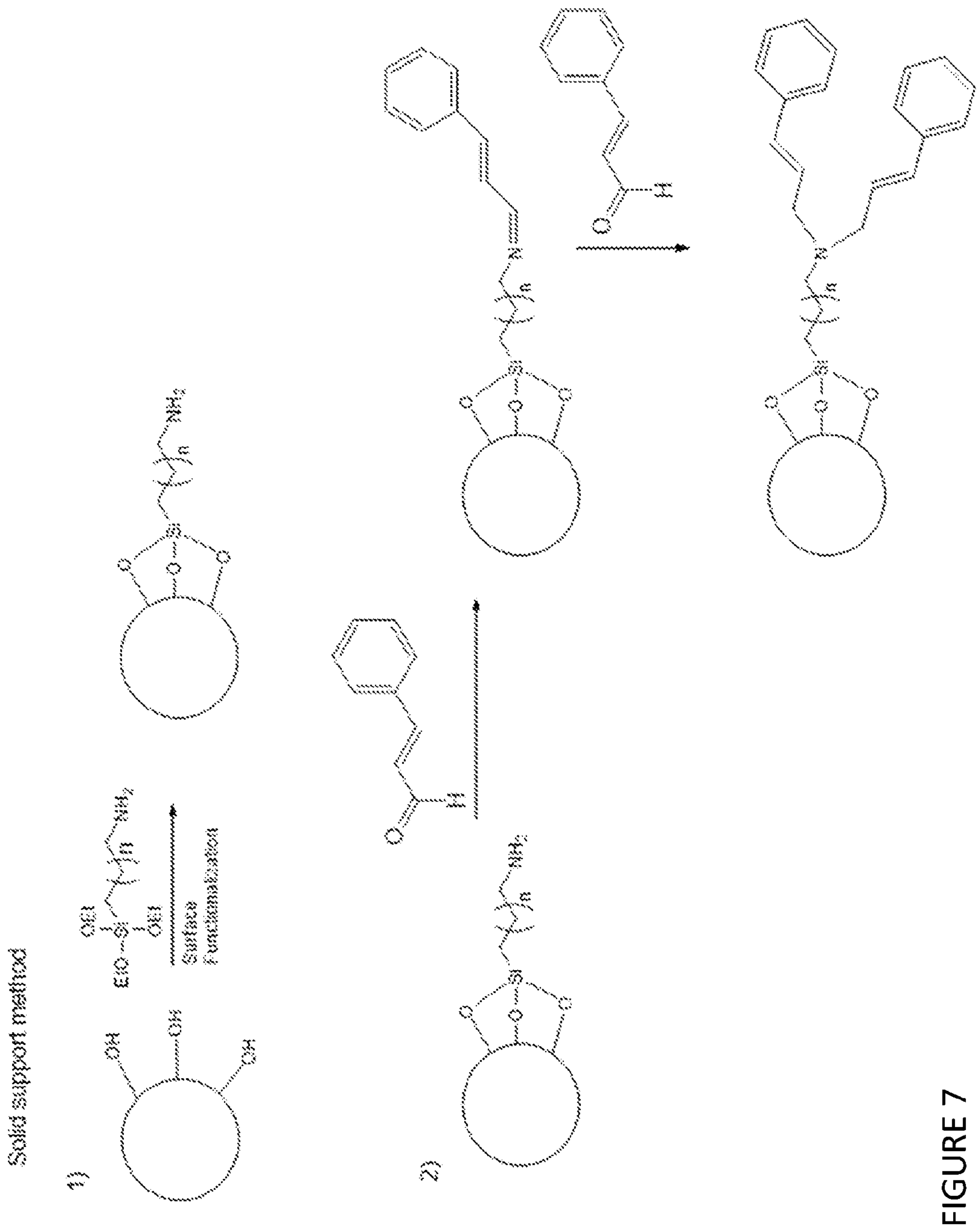
FIG. 7 depicts a representative scheme for the preparation of standard particles having di-cinnamyl groups with core particle (represented as a circle) functionalized utilizing a 12-(triethoxysilyl)-dodecan-1-amine linker by both solid support method and solution method, wherein the antimicrobial part has one monomeric unit (a monomeric backbone, as presented in FIG. 1B). n is an integer of 1 to 16.

This process is exemplified in FIG. 7 for cinnamaldehyde standard particles, but is applicable to other aldehydes.

Preparation of Anti-Microbial Particles, Comprising More than One Monomeric Unit Per One Anti-Microbial Active Unit In one embodiment, this invention provides processes for preparing particles of the composites of this invention, wherein the particles comprise more than one monomeric unit per one anti-microbial active unit. In the following, such processes will be presented in detail.

Figure 8:
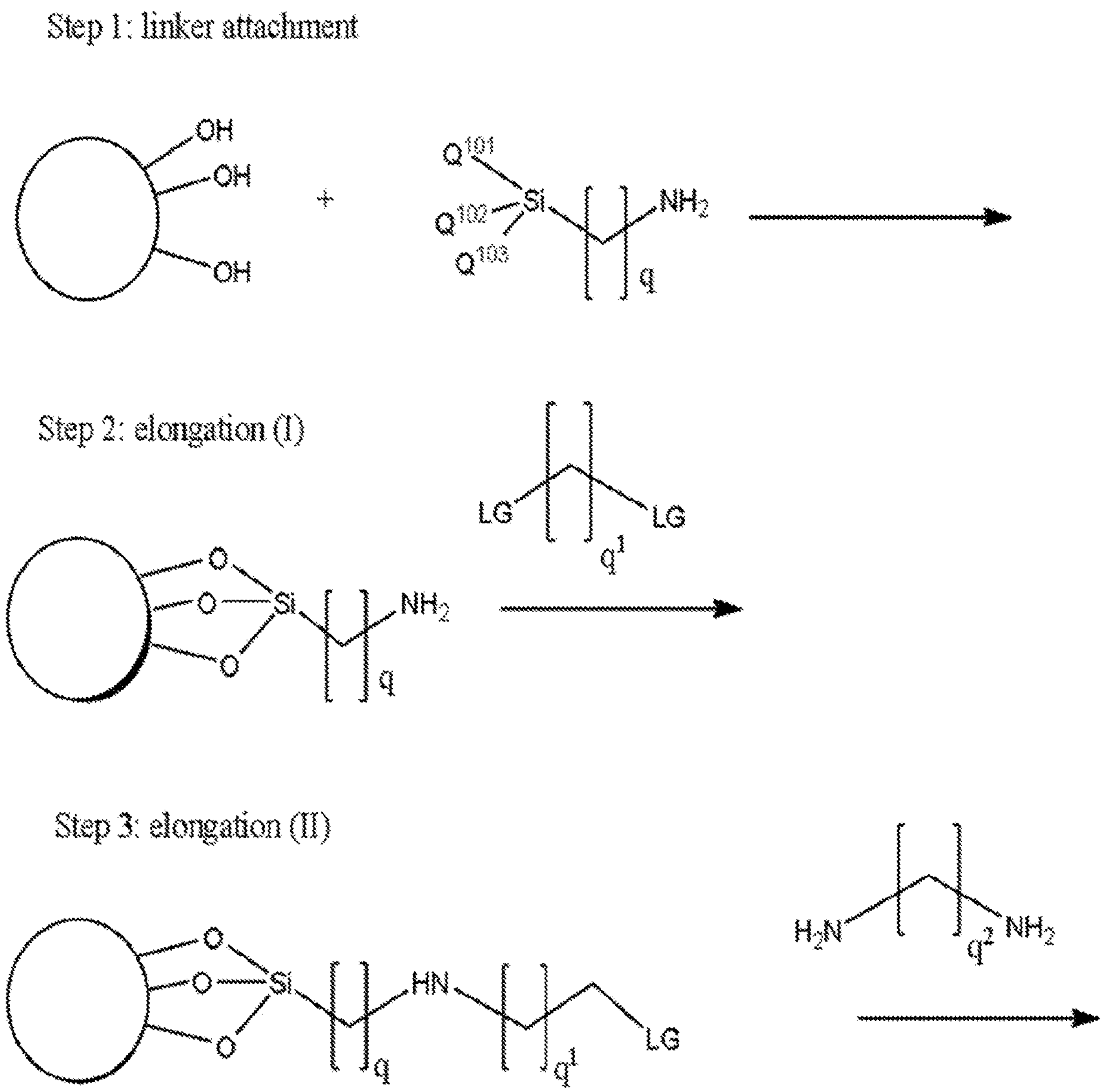
FIG. 8 depicts a representative scheme for the preparation of standard particles by a solid support method, wherein the anti-microbial unit has an oligomeric or polymeric backbone (more than one monomeric unit). The circles represent a core. The starting material is a core terminated on the surface with hydroxyl groups; $Q^{101}$, $Q^{102}$ and $Q^{103}$ and independently alkoxy, alkyl or aryl; LG is Cl, Br, I, mesylate, tosylate or triflate; Hal is Cl, Br or I; q, $q^1$, $q^2$ and $q^3$ are independently an integer between 0-16; $R^1$ and $R^2$ are each independently alkyl, terpenoid, cycloalkyl, aryl, heterocycle, a conjugated alkyl, alkenyl or any combination thereof; and $R^3$ is nothing, hydrogen, alkyl, terpenoid moiety, cycloalkyl, aryl, heterocycle, alkenyl, alkynyl or any combination thereof.
Figure 9:
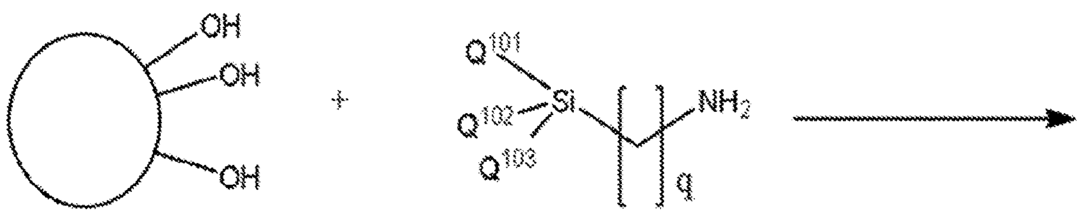
FIG. 9 depicts a representative scheme for the preparation of particles with enhanced thermal stability by a solid support method, wherein the anti-microbial unit has an oligomeric or polymeric backbone (more than one monomeric unit). The circles represent a core. The starting material is a core terminated on the surface with hydroxyl groups; $Q^{101}$, $Q^{102}$ and $Q^{103}$ are each independently alkoxy, alkyl or aryl; LG is Cl, Br, I, mesylate, tosylate or triflate; Hal is Cl, Br or I; q, $q^1$, $q^2$ and $q^3$ are each independently an integer between 0-16; $R_4$ and $R_5$ are each independently methyl, $CF_3$, perhaloalkyl, aryl, benzyl, 2,2-disubstituted $C_3$-$C_{20}$ alkyl, 2,2,2-trisubstituted ethyl, $—CH_2C(=O)OR$, $—CH_2C(=O)OC(=O)R$, $—CH_2C(=S)OR$, $—CH_2C(=O)SR$, $—C(=O)OR$, $—C(=O)OC(=O)R$, $—C(=S)OR$, $—C(=O)SR$, $—C(=O)—R$, $—C(=S)—R$, $—CH_2C(=O)R$, $—CH_2C(=S)R$, $—CH_2CF_3$, $—CH_2NO_2$, 1-alkenyl, 1-alkynyl, 2-alkenyl, 2-alkynyl or any combination thereof; and $R_6$ is methyl, $CF_3$, perhaloalkyl, 2,2-disubstituted $C_3$-$C_{20}$ alkyl, 2,2,2-trisubstituted ethyl, $—CH_2C(=O)OR$, $—CH_2C(=O)OC(=O)R$, $—CH_2C(=S)OR$, $—CH_2C(=O)SR$, $—C(=O)OR$, $—C(=O)OC(=O)R$, $—C(=S)OR$, $—C(=O)SR$, $—C(=O)—R$, $—C(=S)—R$, $—CH_2C(=O)R$, $—CH_2C(=S)R$, $—CH_2CF_3$, $—CH_2NO_2$, terpenoid moiety, cycloalkyl, aryl, phenyl, benzyl, heterocycle, a conjugated alkyl, 1-alkenyl, 1-alkynyl, 2-alkenyl, 2-alkynyl or any combination thereof.
Figure 9:
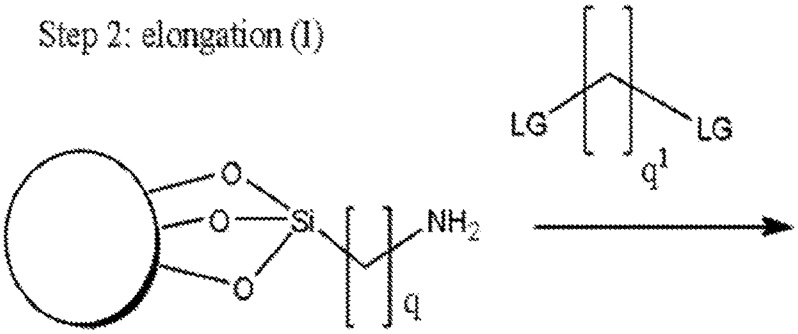
Figure 9:
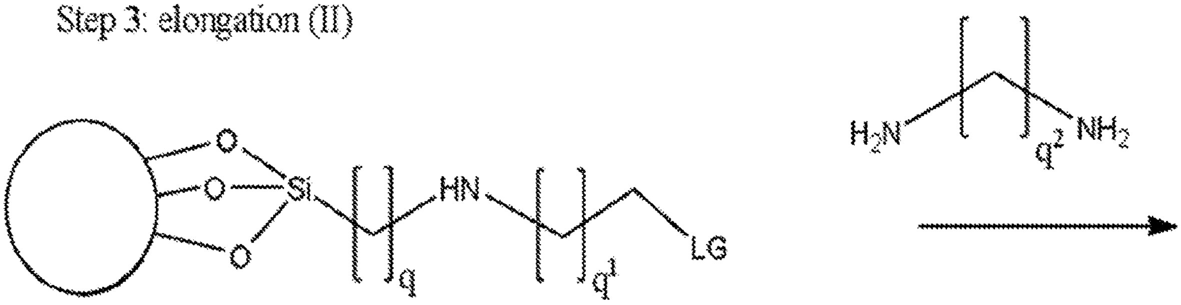
Figure 10A:
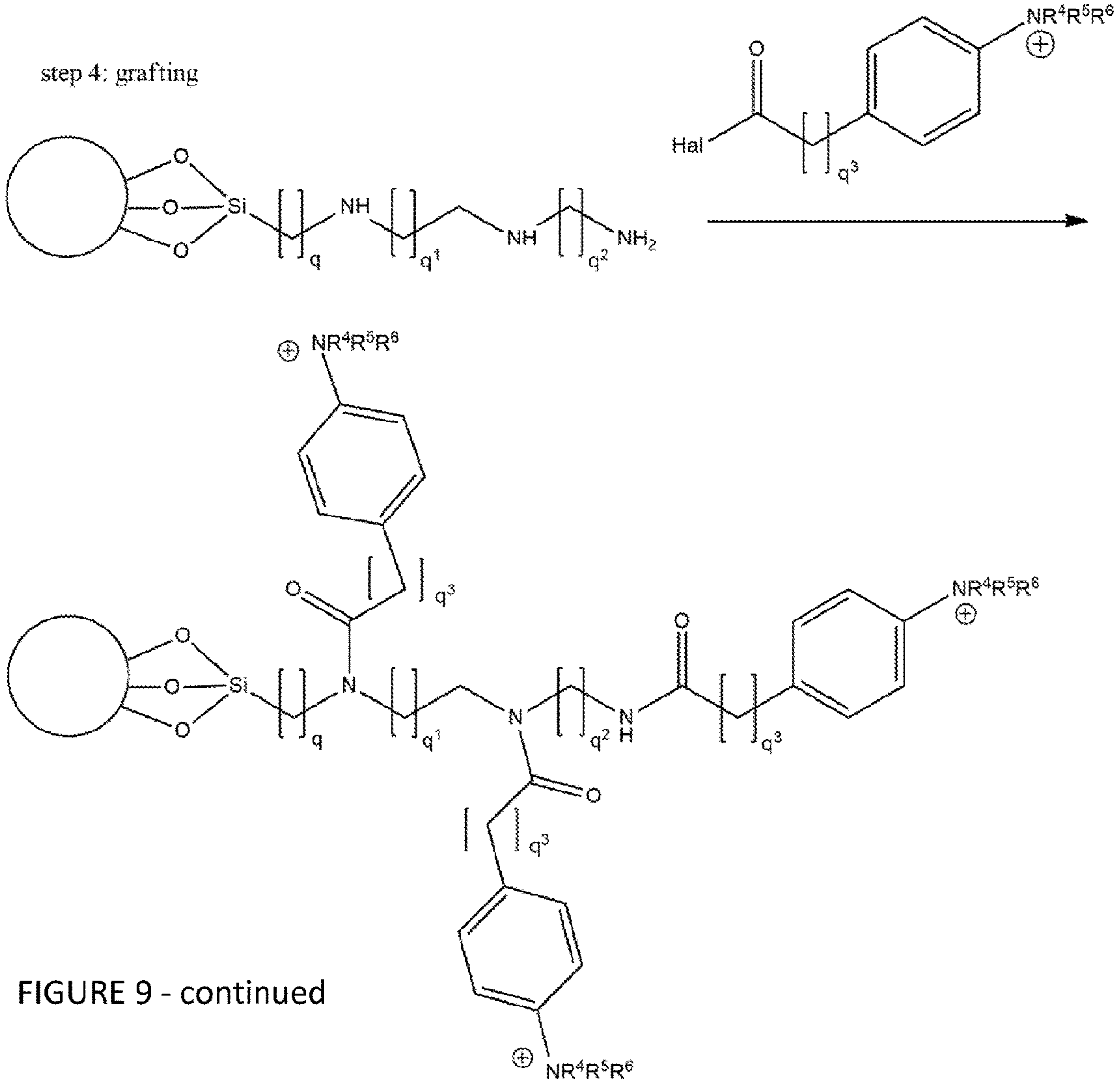
FIGS. 10A-10C depict self-polymerization of trialkoxysilane linker of a standard particle.
Figure 10A:
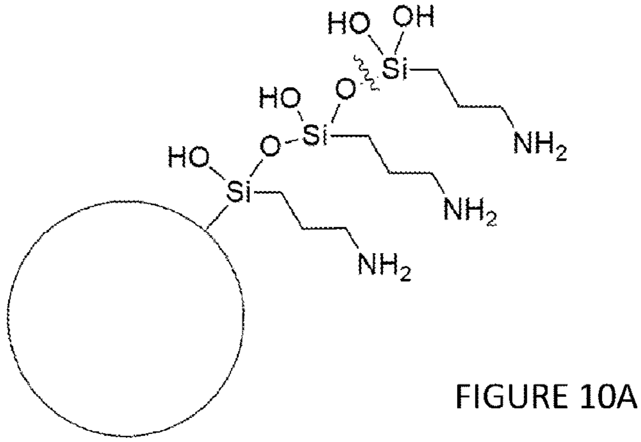
Figure 11A:
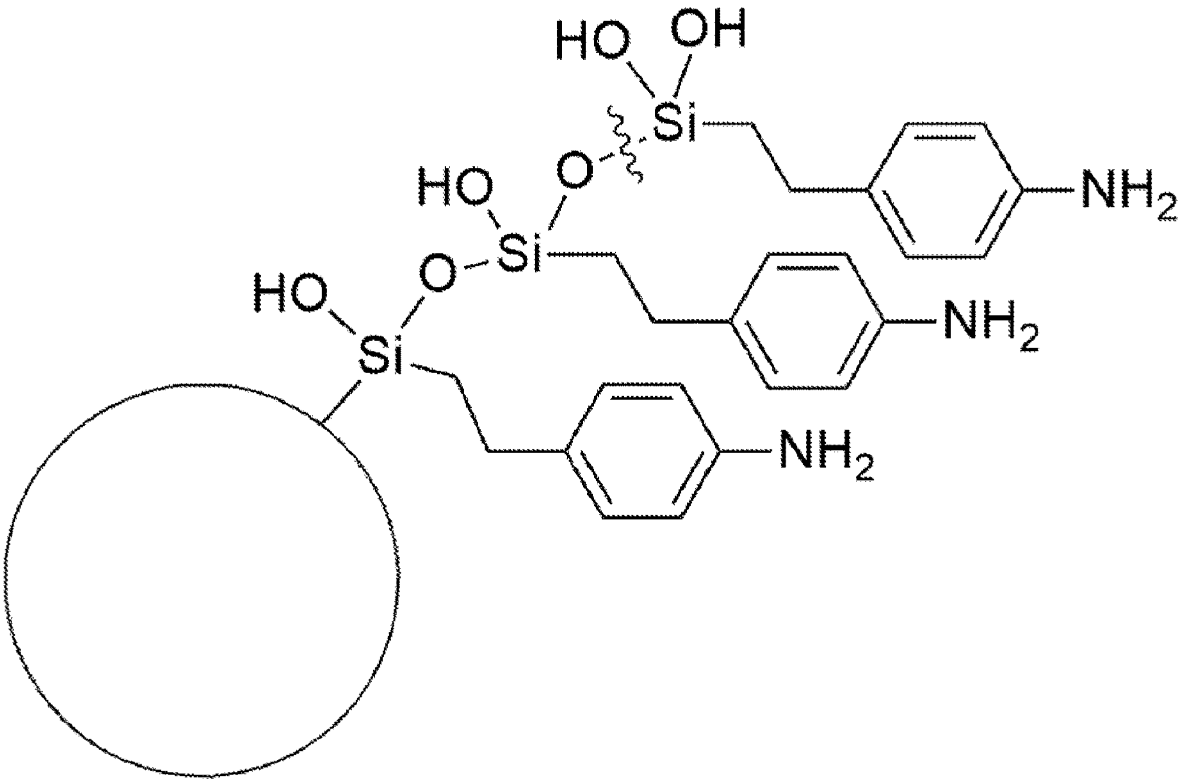
FIGS. 11A-11C depict self-polymerization of trialkoxysilane linker of a particle with enhanced thermal stability.

Solid Support as Method of Preparation of Anti-Microbial Particles Comprising More than One Monomeric Unit Per One Anti-Microbial Active Unit The solid support method comprises a few stages. First, for standard particle, the linker molecule (dilute solutions of a few percent) is allowed to condense onto particles surface (surface functionalization) via (acid catalyzed) hydrolysis of leaving groups, resulting in the attachment of the linker to the core (FIG. 8, step 1). Second, the attached linker is elongated. In another embodiment, this stage is achieved synthetically via one step or more. In another embodiment, elongation is achieved by consecutive addition of difunctionalized alkane and diaminoalkane, wherein amines (of attached linker and diaminoalkane) attack electrophilic centers of the difunctionalized alkane (FIG. 8, steps 2 and 3). In another embodiment, such consecutive addition is optionally repeated for 1-10 times. Finally, the anti-microbial active group (usually attached to an alkylene chain) is grafted to resulting attached and elongated linker. In another embodiment, grafting is accomplished when amines on the attached and elongated linker attack acyl halide moiety of the molecule of the anti-microbial active group which is grafted (FIG. 8, step 4). Similar process is presented for particles with enhanced thermal stability (FIG. 9), where the ammonium end of the anti microbial active group is replaced with an anilinium end and $R^1$-$R^3$ are replaced with $R^4$-$R^6$. In FIG. 8, $R^1$ and $R^2$ are each independently alkyl, terpenoid, cycloalkyl, aryl, heterocycle, a conjugated alkyl, alkenyl or any combination thereof; and $R^3$ is nothing, hydrogen, alkyl, terpenoid moiety, cycloalkyl, aryl, heterocycle, alkenyl, alkynyl or any combination thereof. In FIG. 9, $R_4$ and $R_5$ are each independently methyl, $CF_3$, perhaloalkyl, aryl, benzyl, 2,2-disubstituted $C_3$-$C_{20}$ alkyl, 2,2,2-trisubstituted ethyl, —$CH_2C$(═O)OR, —$CH_2C$(═O)OC(═O)R, —$CH_2C$(═S)OR, —$CH_2C$(═O)SR, —C(═O)OR, —C(═O)OC(═O)R, —C(═S)OR, —C(═O)SR, —C(═O)—R, —C(═S)—R, —$CH_2C$(═O)R, —$CH_2C$(═S)R, —$CH_2CF_3$, —$CH_2NO_2$, 1-alkenyl, 1-alkynyl, 2-alkenyl, 2-alkynyl or any combination thereof; and $R_6$ is methyl, $CF_3$, perhaloalkyl, 2,2-disubstituted $C_3$-$C_{20}$ alkyl, 2,2,2-trisubstituted ethyl, —$CH_2C$(═O)OR, —$CH_2C$(═O)OC(═O)R, —$CH_2C$(═S)OR, —$CH_2C$(═O)SR, —C(═O)OR, —C(═O)OC(═O)R, —C(═S)OR, —C(═O)SR, —C(═O)—R, —C(═S)—R, —$CH_2C$(═O)R, —$CH_2C$(═S)R, —$CH_2CF_3$, —$CH_2NO_2$, terpenoid moiety, cycloalkyl, aryl, phenyl, benzyl, heterocycle, a conjugated alkyl, 1-alkenyl, 1-alkynyl, 2-alkenyl, 2-alkynyl or any combination thereof In another embodiment, the same trialkoxysilane linker molecule (of FIGS. 8-9) is used initially, however in a higher concentration (≥10% by wt) and it initially self-polymerizes (FIGS. 10A and 11A for standard and thermally stable enhanced particles, respectively) under basic catalysis. Functionalization of the solid supported linker progresses similarly as in the procedures described hereinabove for particles that comprise one monomeric unit per one anti-microbial active unit (FIGS. 2-7).

Figure 12:
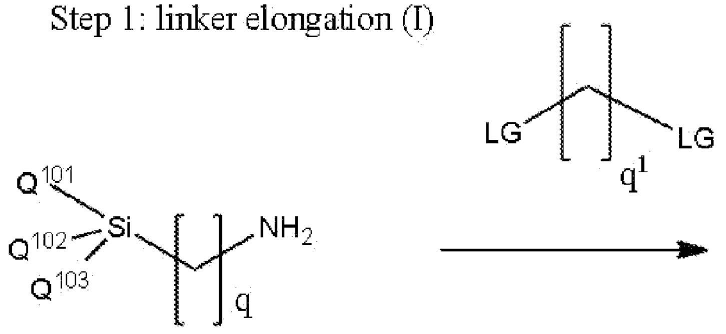
FIG. 12 depicts a representative scheme for the preparation of standard particles in a solution method, wherein the anti-microbial unit has more than one monomeric unit (i.e has an oligomeric or polymeric backbone). The circles represent a core. The starting material is a core terminated on the surface with hydroxyl groups; $Q^{101}$, $Q^{102}$ and $Q^{103}$ and independently alkoxy, alkyl or aryl; LG is Cl, Br, I, mesylate, tosylate or triflate; Hal is Cl, Br or I; q, $q^1$, $q^2$ and $q^3$ are independently an integer between 0-16; $R^1$ and $R^2$ are each independently alkyl, terpenoid, cycloalkyl, aryl, heterocycle, a conjugated alkyl, alkenyl or any combination thereof; and $R^3$ is nothing, hydrogen, alkyl, terpenoid moiety, cycloalkyl, aryl, heterocycle, alkenyl, alkynyl or any combination thereof.
Figure 12:
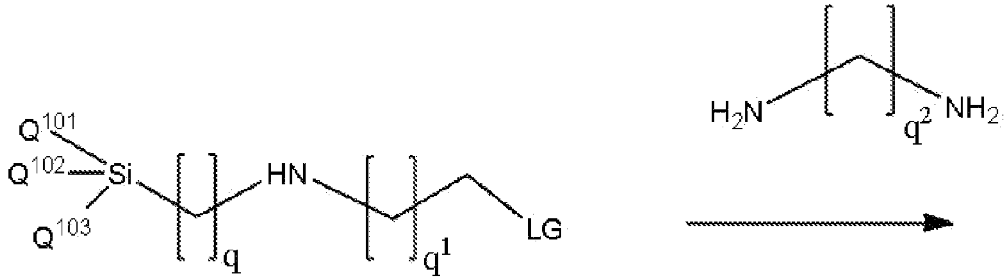
Figure 12:
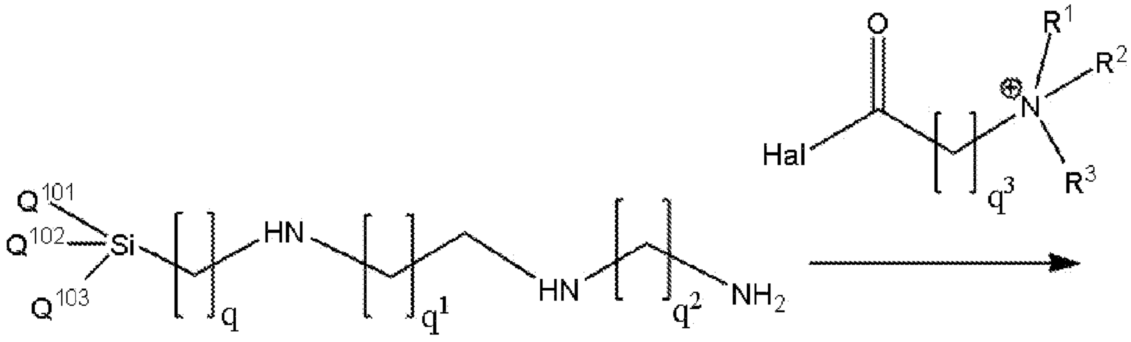
Figure 13:
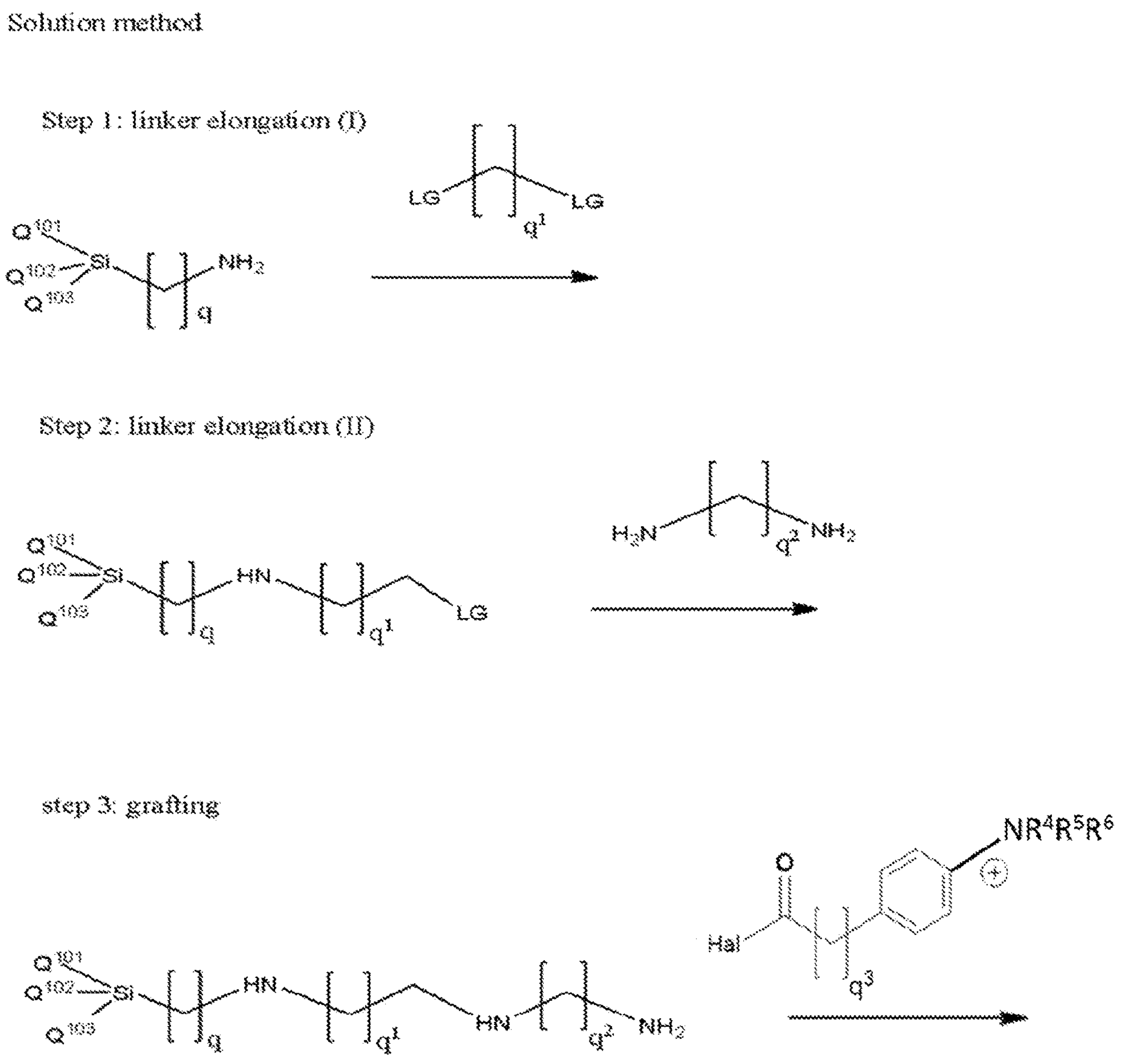
FIG. 13 depicts a representative scheme for the preparation of particles with enhanced thermal stability in a solution method, wherein the anti-microbial unit has more than one monomeric unit (i.e has an oligomeric or polymeric backbone). The circles represent a core. The starting material is a core terminated on the surface with hydroxyl groups; $Q^{101}$, $Q^{102}$ and $Q^{103}$ and independently alkoxy, alkyl or aryl; LG is Cl, Br, I, mesylate, tosylate or triflate; Hal is Cl, Br or I; q, $q^1$, $q^2$ and $q^3$ are independently an integer between 0-16; $R_4$ and $R_5$ are each independently methyl, $CF_3$, perhaloalkyl, aryl, benzyl, 2,2-disubstituted $C_3$-$C_{20}$ alkyl, 2,2,2-trisubstituted ethyl, $—CH_2C(=O)OR$, $—CH_2C(=O)OC(=O)R$, $—CH_2C(=S)OR$, $—CH_2C(=O)SR$, $—C(=O)OR$, $—C(=O)OC(=O)R$, $—C(=S)OR$, $—C(=O)SR$, $—C(=O)—R$, $—C(=S)—R$, $—CH_2C(=O)R$, $—CH_2C(=S)R$, $—CH_2CF_3$, $—CH_2NO_2$, 1-alkenyl, 1-alkynyl, 2-alkenyl, 2-alkynyl or any combination thereof; and $R_6$ is methyl, $CF_3$, perhaloalkyl, 2,2-disubstituted $C_3$-$C_{20}$ alkyl, 2,2,2-trisubstituted ethyl, $—CH_2C(=O)OR$, $—CH_2C(=O)OC(=O)R$, $—CH_2C(=S)OR$, $—CH_2C(=O)SR$, $—C(=O)OR$, $—C(=O)OC(=O)R$, $—C(=S)OR$, $—C(=O)SR$, $—C(=O)—R$, $—C(=S)—R$, $—CH_2C(=O)R$, $—CH_2C(=S)R$, $—CH_2CF_3$, $—CH_2NO_2$, terpenoid moiety, cycloalkyl, aryl, phenyl, benzyl, heterocycle, a conjugated alkyl, 1-alkenyl, 1-alkynyl, 2-alkenyl, 2-alkynyl or any combination thereof.

Solution Method as Method of Preparation of Anti-Microbial Particles Comprising More than One Monomeric Unit Per One Anti-Microbial Active Unit The solution method comprises a few stages. The first step involves elongation of the linker molecule. In another embodiment, this step is achieved synthetically via one step or more. In another embodiment, elongation is achieved by consecutive addition of difunctionalized alkane and diaminoalkane wherein amines (of linker and diaminoalkane) attack electrophilic centers of the difunctionalized alkane (FIGS. 12 and 13 for standard and thermally stable enhanced particles, respectively: steps 1 and 2). In another embodiment, such consecutive addition is optionally repeated for 1-10 times. In the second stage, the anti-microbial active group (usually attached to an alkylene chain) is grafted to resulting elongated linker. In another embodiment, grafting is accomplished when amines on the elongated linker attack acyl halide moiety of the molecule of the anti-microbial active group which is grafted (FIGS. 12 and 13, step 3). Finally, the elongated, anti-microbial active linker is attached to the core via functionalization thereof. In this step, the linker molecule (dilute solutions of a few percent) is allowed to condense onto particles surface (surface functionalization) via (acid catalyzed) hydrolysis of leaving groups, resulting in the attachment of the linker to the core (FIGS. 12 and 13, step 4).

Figure 14:
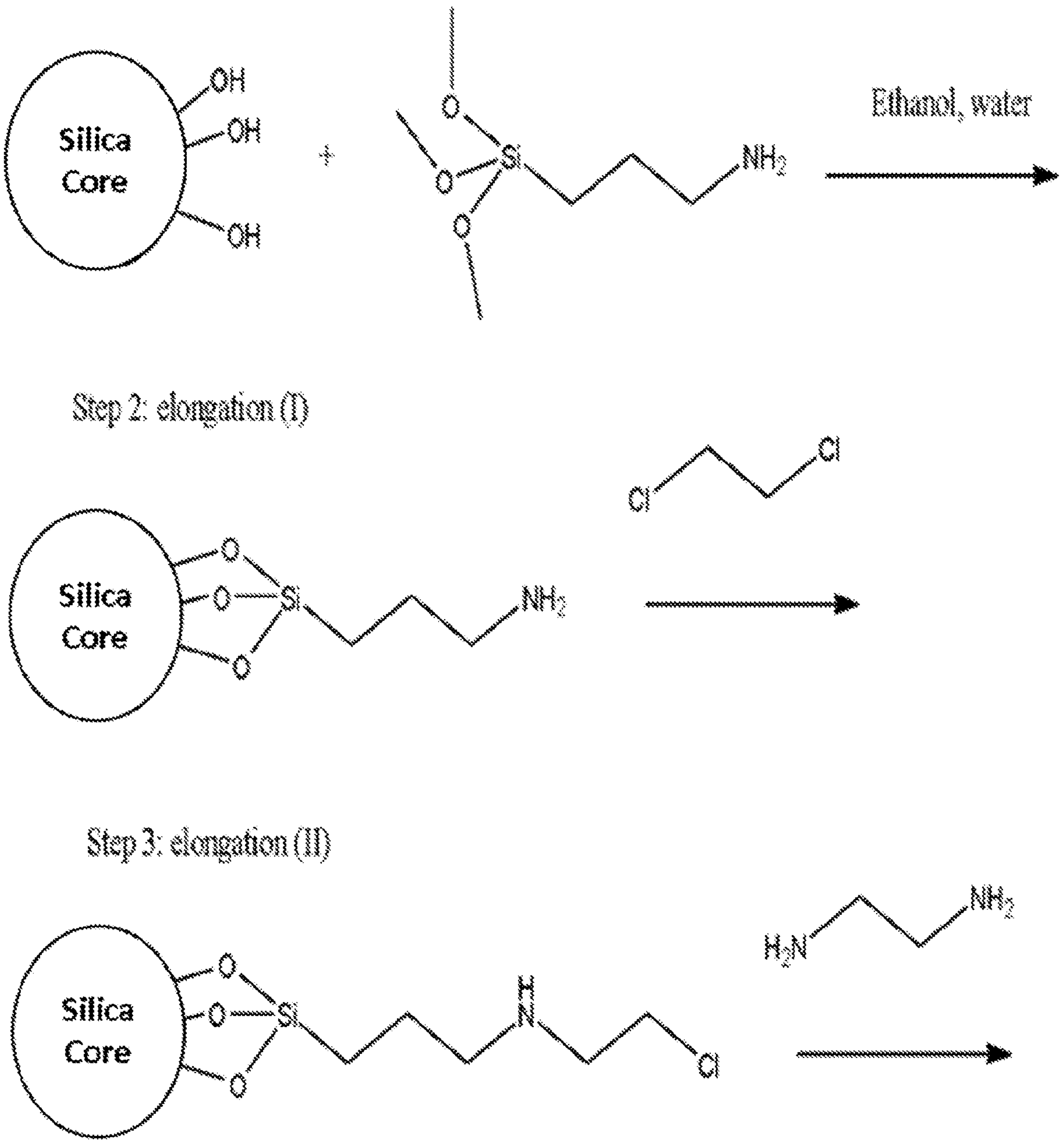
FIG. 14 depicts a scheme for the preparation of silica based anti-microbial standard particles comprising dimethylethylammonium as the anti-microbial active group, in a solid support method, wherein the anti-microbial unit has more than one monomeric unit (i.e has an oligomeric or polymeric backbone).
Figure 15:
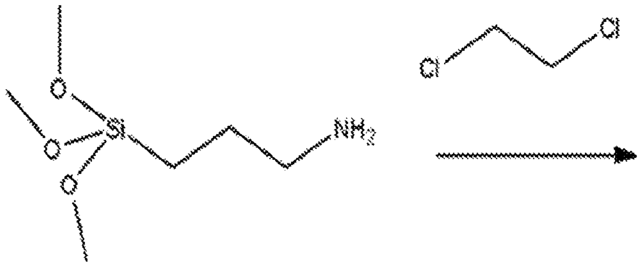
FIG. 15 depicts a scheme for the preparation of silica based anti-microbial standard particles comprising dimethylethylammonium as the anti-microbial active group, in a solution method, wherein the anti-microbial unit has more than one monomeric unit (i.e has an oligomeric or polymeric backbone).
Figure 15:
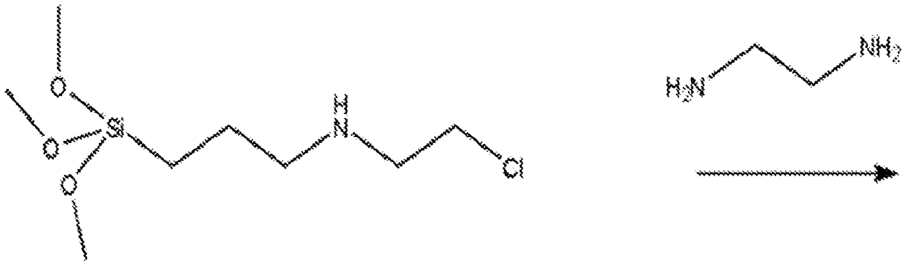
Figure 15:
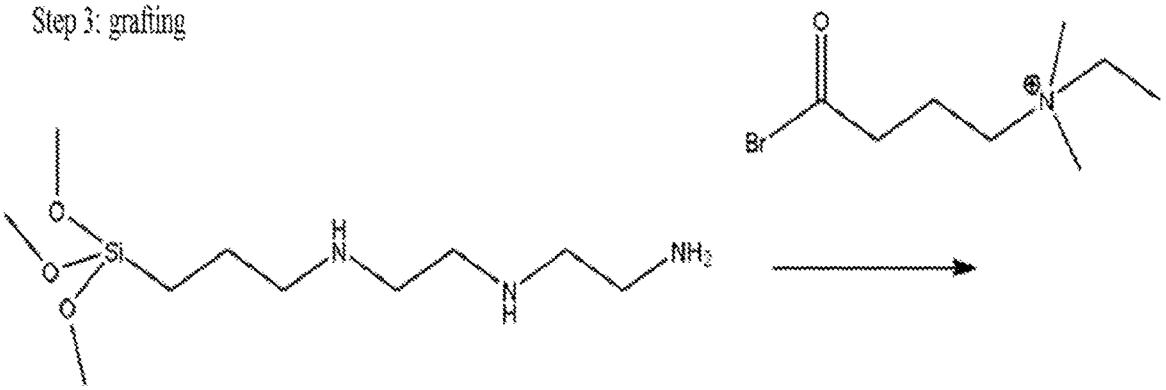
Figure 16:
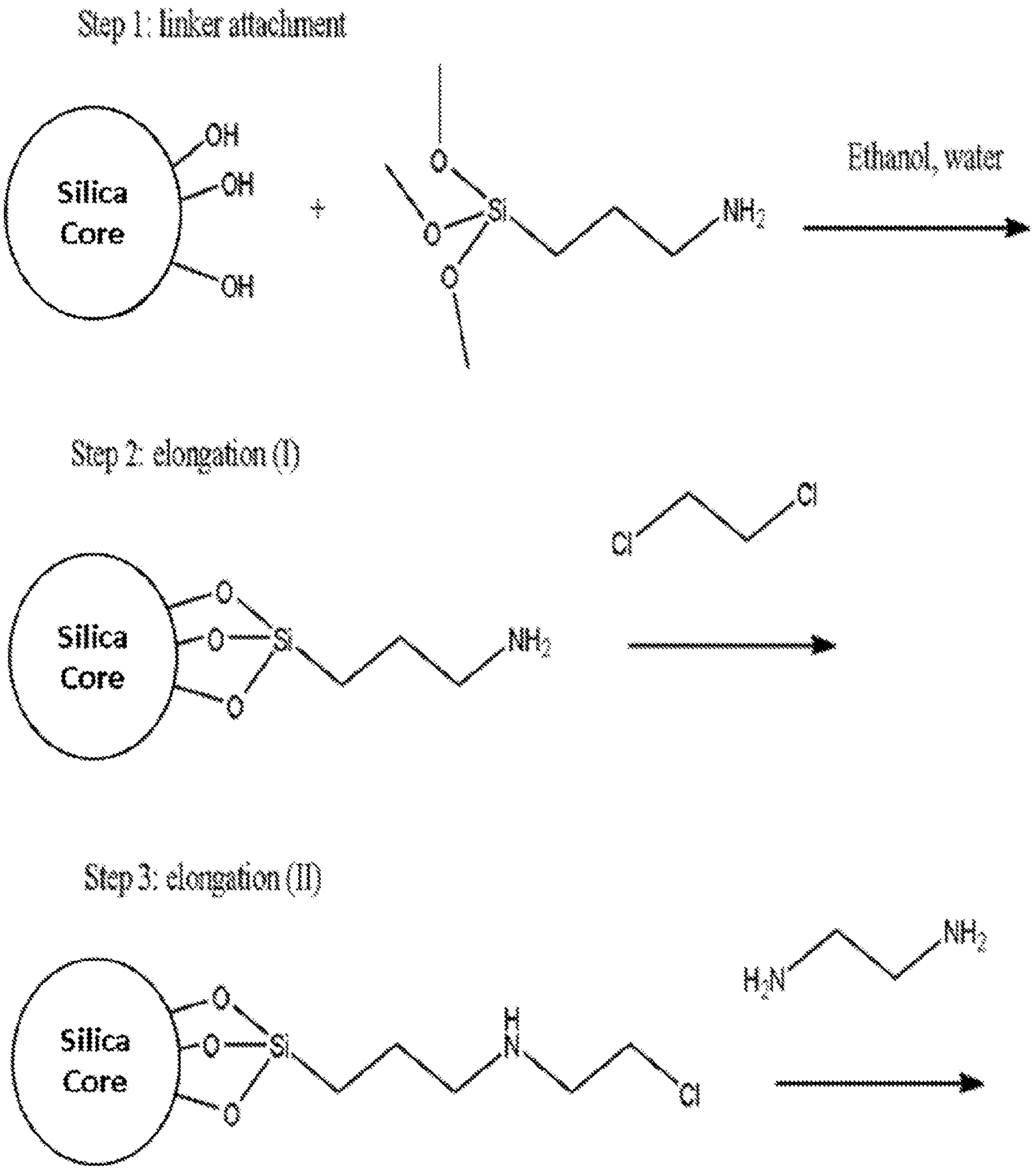
FIG. 16 depicts a scheme for the preparation of silica based anti-microbial particles with enhanced thermal stability comprising dimethylbenzylammonium as the anti-microbial active group, in a solid support method, wherein the anti-microbial unit has more than one monomeric unit (i.e has an oligomeric or polymeric backbone).
Figure 17:
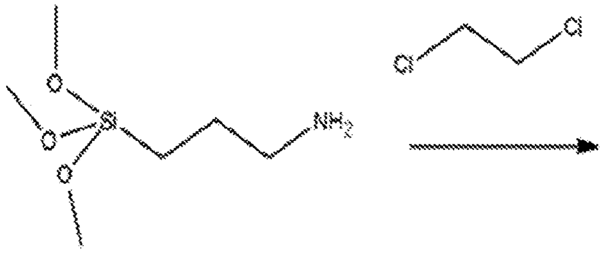
FIG. 17 depicts a scheme for the preparation of silica based anti-microbial particles with enhanced thermal stability comprising dimethylbenzylammonium as the anti-microbial active group, in a solution method, wherein the anti-microbial unit has more than one monomeric unit (i.e has an oligomeric or polymeric backbone).
Figure 17:
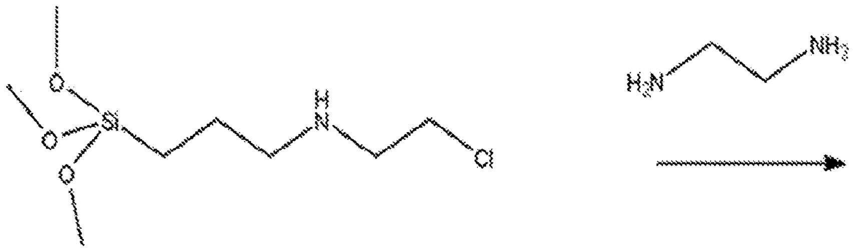
Figure 17:
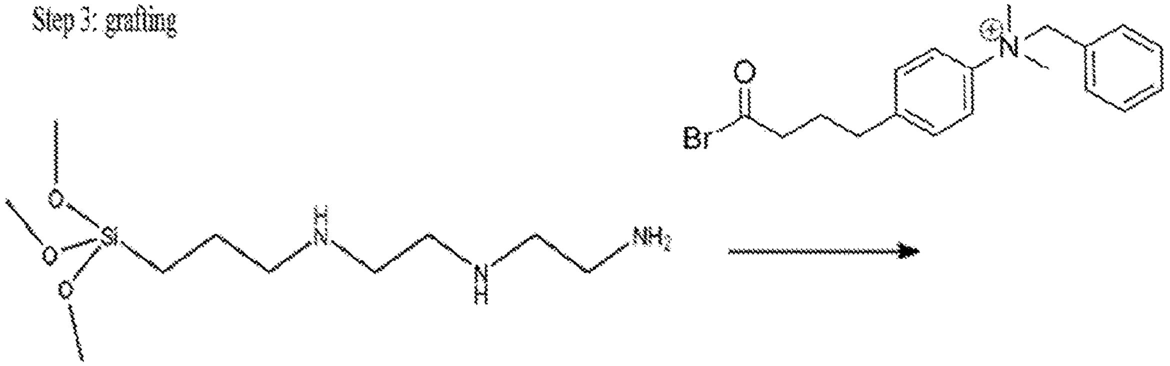

This process is exemplified in FIGS. 14-15 for silica standard particles functionalized with dimethylethylammonium, Similarly, the process is exemplified in FIGS. 16-17—for silica particles with enhanced thermal stability functionalized with dimethybenzylammonium, but is applicable to other hydroxyl-terminated cores and anti-microbial active groups. The processes of FIGS. 14-17 are applicable to other hydroxyl-terminated cores and anti-microbial active groups.

Figure 10B:
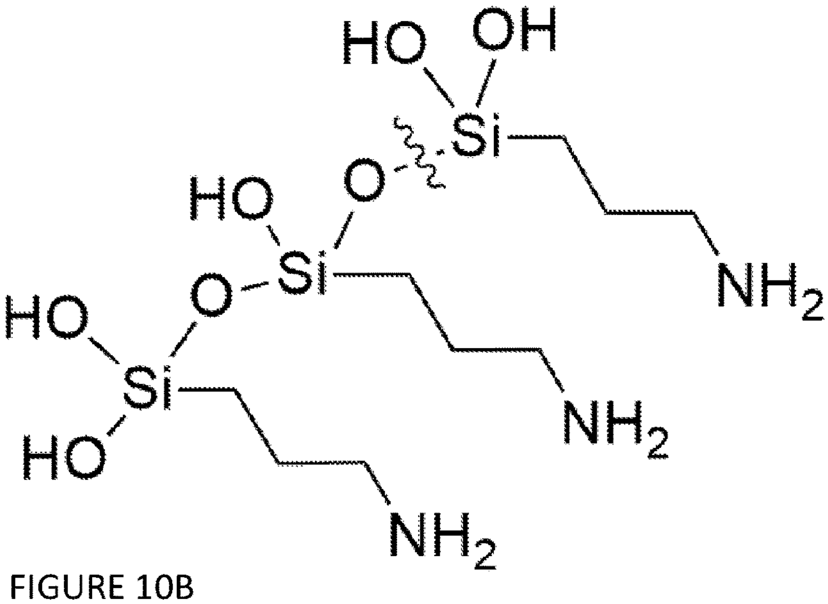
Figure 10C:
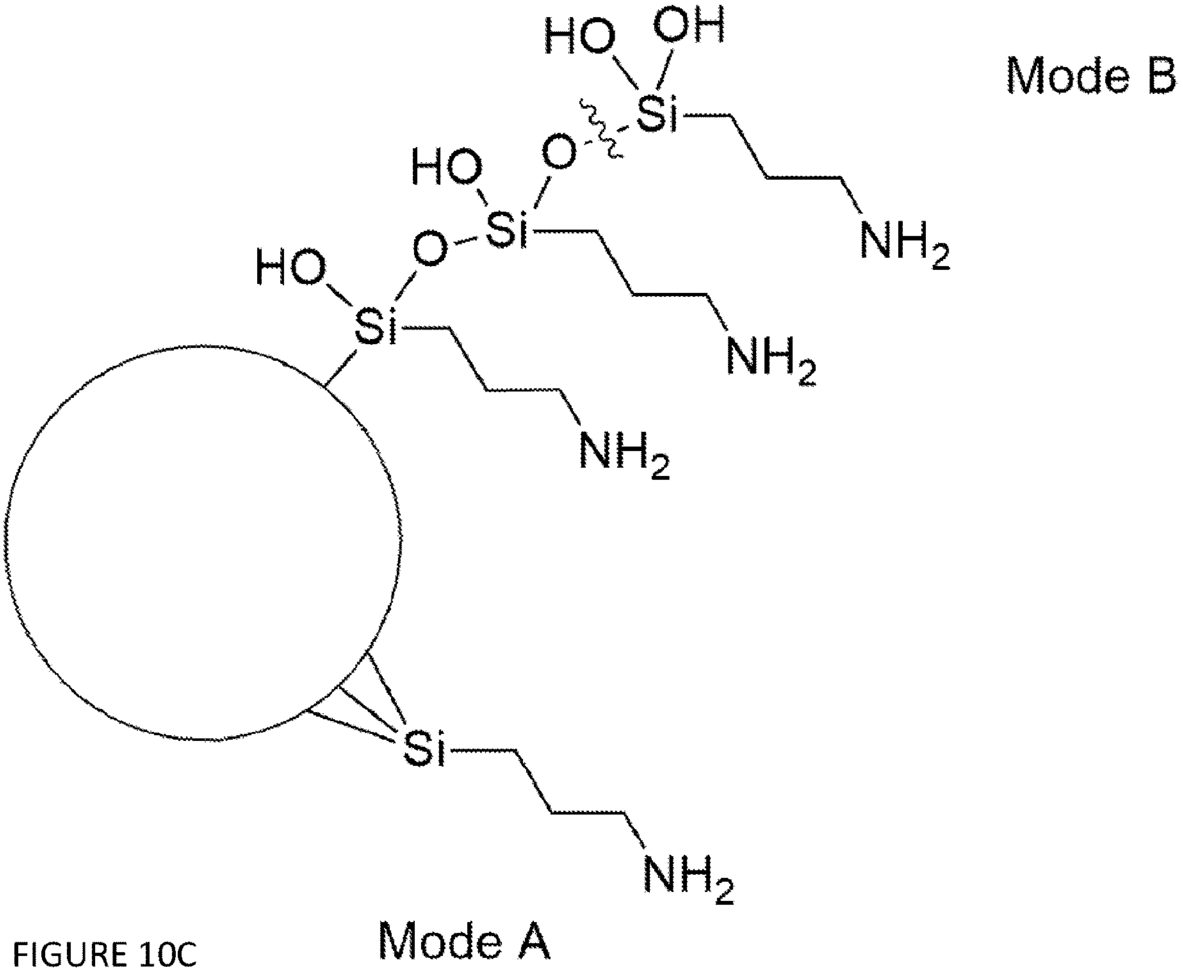
Figure 11B:
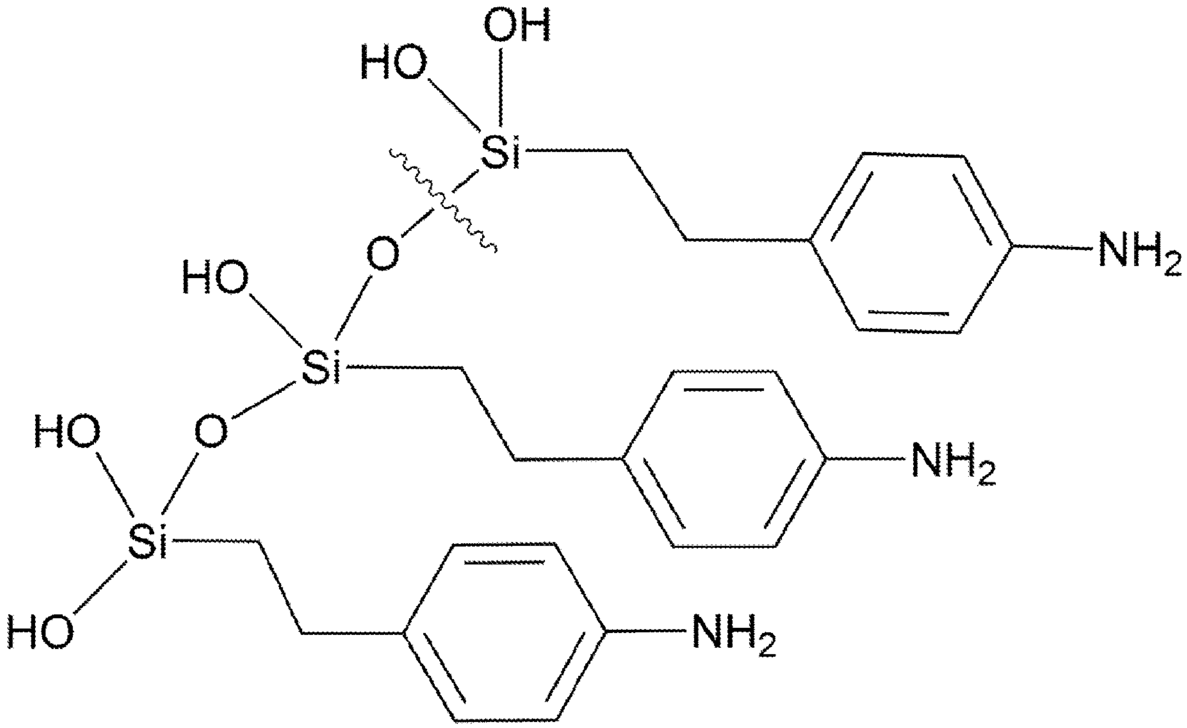
Figure 11C:
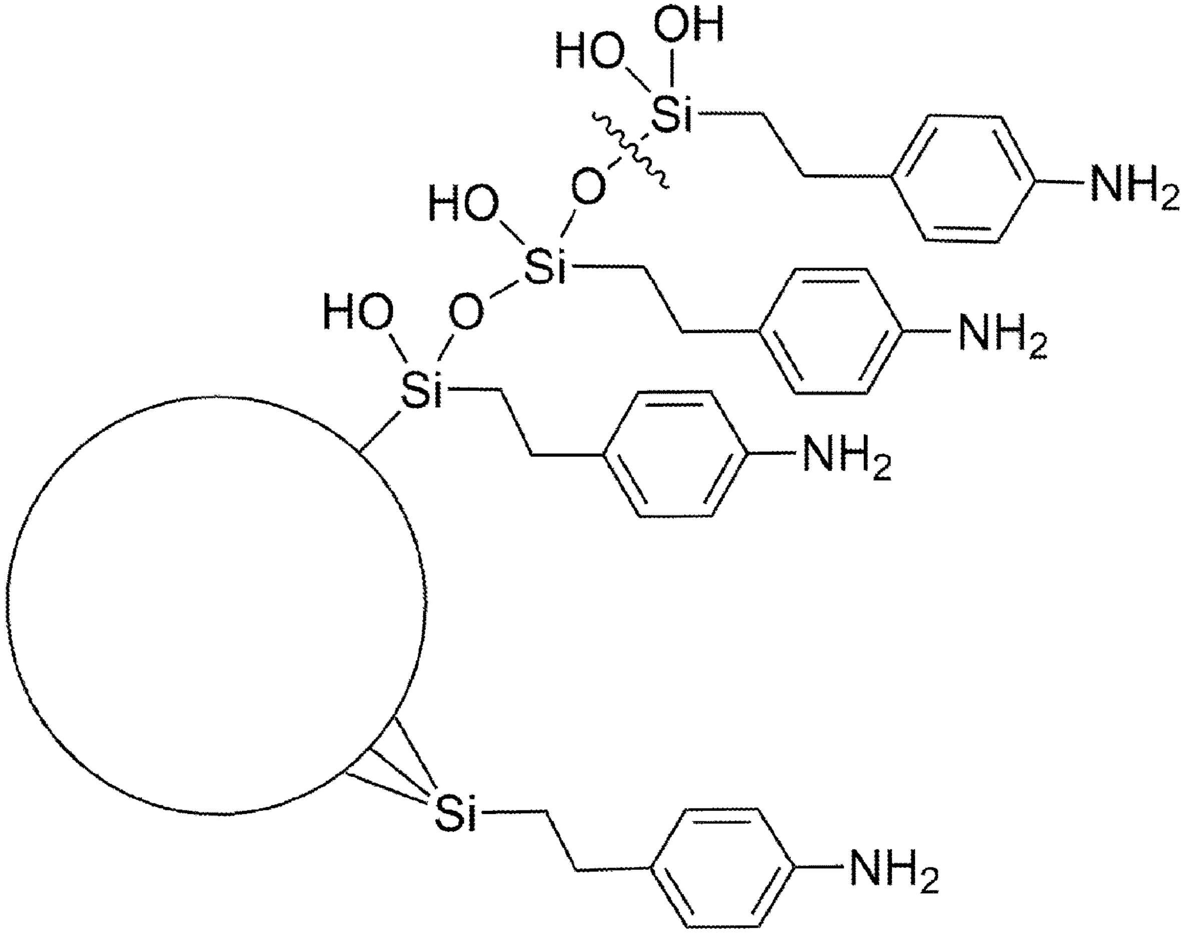

In another embodiment, the same trialkoxysilane linker molecule is used initially, however in a higher concentration (≥10% by weight) and it initially self-polymerizes (FIGS. 10B and 11B for standard and thermally stable enhanced particles, respectively) under basic catalysis. Functionalization of the linker progresses similarly as in the procedures described hereinabove for particles that comprise one monomeric unit per one anti-microbial active part (FIGS. 2-7).

Preparation of Core Particles

In some embodiments, the particles of the composites of this invention which comprise one or more monomeric units per one anti-microbial active part, comprise cores which are prepared according to the following.

Porous silica materials can be prepared by reaction of $SiCl_4$ with alcohol or water, followed by drying using centrifugation and/or heating utilizing airflow or under vacuum conditions. Dense fumed silica particles (pyrogenic) were prepared by pyrolysis of $SiCl_4$.

An alternative preparation method of silica core material can be carried by the hydrolysis of tetraethylorthosilicate (TEOS) or tetramethyl orthosilicate (TMS) in the presence of alcohol or water solution and under basic (Stober) or acidic catalytic conditions.

Mesoporous silica particles can be prepared by hydrolysis of TEOS or TMS at low temperatures, preferably in a temperature not exceeding 60° C., followed by dehydration by centrifugation and/or evaporation under airflow or vacuum conditions.

Dense particles can be prepared utilizing intense heating in a process called calcination. Typically, such process takes place at high temperatures at about 250° C.

Uses of the Coating of this Invention

According to another aspect of the invention there is provided a method for inhibition of bacteria, comprising contacting the bacteria with a coated substrate of this invention, comprising the anti-microbail particle(s) described hereinabove. The term "inhibition" is referred to destruction, i.e. annihilation, of at least 99% of the bacteria, preferably 99.9%, most preferably 99.99% of the bacteria; reduction in the growth rate of the bacteria; reduction in the size of the population of the bacteria; prevention of growth of the bacteria; causing irreparable damage to the bacteria; destruction of a biofilm of such bacteria; inducing damage, short term or long term, to a part or a whole existing biofilm; preventing formation of such biofilm; inducing biofilm management; or bringing about any other type of consequence which may affect such population or biofilm and impose thereto an immediate or long term damage (partial or complete). In another embodiment, this invention provides coated substrates, for use in a method for inhibition of bacteria, as described above.

The term "biofilm" refers to a population of biological species (bacteria) attached to a solid surface.

In a preferred embodiment, the inhibition is achieved by contacting the bacteria with a coated substrate according to this invention which contains up to 5% w/w or more preferably up to 1% particles.

In one embodiment, the invention is directed to a packaging composition comprising a coated substrate of this invention. In another embodiment, the coating of the coated substrate is a thermoplastic polymer and/or hydrogel embedded with anti-microbial particles. In another embodiment, the thermoplastic polymer and/or hydrogel is embedded with a mixture of two or more different particles. In another embodiment, the packaging composition is used in the packaging of food, beverage, pharmaceutical ingredients, medical devices, surgical equipment before operation, pre operation equipment, cosmetics, and sterilized equipment/materials. Each possibility represents a separate embodiment of this invention.

In one embodiment, the packaging composition comprises a coated substrate which comprises thermoplastic polymer and/or hydrogel embedded with the particles as referred hereinabove. In another embodiment, the thermoplastic polymer is polyvinylchloride (PVC), polyethylene, polypropylene, silicone, epoxy resin or acrylic polymers. In another embodiment, the thermoplastic polymer is poly methylmethacrylate or polyurethane. Each possibility represents a separate embodiment of this invention.

In another embodiment, the packaging composition further comprises binders, coatings, lubricants and disintegrants. In another embodiment, non-limiting examples of binders include saccharides, gelatin, polyvinylpyrolidone (PVP) and polyethylene glycol (PEG). In another embodiment, non-limiting examples of coatings include hydroxypropylmethylcellulose, polysaccharides and gelatin. In another embodiment, non-limiting examples of lubricants include talc, stearin, silica and magnesium stearate. In another embodiment, non-limiting examples of disintegrants include crosslinked polyvinylpyrolidone, crosslinked sodium carboxymethyl cellulose (croscarmellose sodium) and modified starch sodium starch glycolate. Each possibility represents a separate embodiment of this invention.

In one embodiment, the packaging composition is used for packaging pharmaceutical ingredients. In another embodiment, non-limiting examples of pharmaceutical ingredients include analgesics, antibiotics, anticoagulants, antidepressants, anti-cancers, antiepileptics, antipsychotics, antivirals, Sedatives and antidiabetics. In another embodiment, non-limiting examples of analgesics include paracetamol, non-steroidal anti-inflammatory drugs (NSAIDs), morphine and oxycodone. In another embodiment, non-limiting examples of antibiotics include penicillin, cephalosporin, ciprofloxacin and erythromycin. In another embodiment, non-limiting examples of anticoagulants include warfarin, dabigatran, apixaban and rivaroxaban. In another embodiment, non-limiting examples of Antidepressants include sertraline, fluoxetine, citalopram and paroxetine. In another embodiment, non-limiting examples of anti-cancers include Capecitabine, Mitomycin, Etoposide and Pembrolizumab. In another embodiment, non-limiting examples of antiepileptics include Acetazolamide, Clobazam, Ethosuximide and lacosamide. In another embodiment, non-limiting examples of antipsychotics include Risperidone, Ziprasidone, Paliperidone and Lurasidone. In another embodiment, non-limiting examples of antivirals include amantadine, rimantadine, oseltamivir and zanamivir. In another embodiment, non-limiting examples of sedatives include Alprazolam, Clorazepate, Diazepam and Estazolam. In another embodiment, non-limiting examples of antidiabetics include glimepiride, gliclazide, glyburide and glipizide. Each possibility represents a separate embodiment of this invention.

In one embodiment, the packaging composition is used in the packaging of food ingredients. In another embodiment, non-limiting examples of food ingredients packaged with the packaging material of the invention include fresh food, preservatives, sweeteners, color additives, flavors and spices, nutrients, emulsifiers, binders and thickeners. In another embodiment, non-limiting examples of fresh food include: meat, poultry, fish, dairy products, fruits and vegetables. In another embodiment, non-limiting examples of preservatives include Ascorbic acid, citric acid, sodium benzoate, calcium propionate, sodium erythorbate, butylated hydroxy toluene (BHT), silver, chlorhexidine, trichlozan and sodium nitrite. In another embodiment, non-limiting examples of sweeteners include Sucrose (sugar), glucose, fructose, sorbitol, mannitol and corn syrup. In another embodiment, non-limiting examples of color additives include Orange B, Citrus Red No. 2, annatto extract, beta-carotene, grape skin extract, cochineal extract or carmine and paprika oleoresin. In another embodiment, non-limiting examples of flavors and spices include monosodium glutamate, glycine slats, inosinic acid, isoamyl acetate, and limonene and allyl hexanoate. In another embodiment, non-limiting examples of nutrients include Thiamine hydrochloride, riboflavin (Vitamin $B_2$), niacin, niacinamide, folate or folic acid. In another embodiment, non-limiting examples of emulsifiers include Soy lecithin, mono- and diglycerides, egg yolks, polysorbates and sorbitan monostearate. In another embodiment, non-limiting examples of binders and thickeners include Gelatin, pectin, guar gum, carrageenan, xanthan gum and whey. Each possibility represents a separate embodiment of this invention.

In one embodiment, this invention provides a method for inhibiting or preventing biofilm formation or growth, comprising applying onto a susceptible or infected surface or a medical device a coated substrate of this invention.

In one embodiment, this invention provides a method for inhibiting or preventing biofilm formation or growth, comprising applying onto a susceptible or infected surface or a medical device a coating comprising anti-microbial particles and a matrix.

In another embodiment, this invention provides a coating of this invention for use in inhibiting or preventing a biofilm formation.

In one embodiment, this invention provides a method for inhibiting or preventing biofilm formation or growth comprising placing a medical device of this invention (comprising a coated substrate of this invention as referred hereinabove) on the surface to be treated. In another embodiment, the medical device is a wound dressing. In another embodiment, the wound dressing comprises/is the coated substrate which comprises the anti-microbial particles as described above and polymers and/or biopolymers. In another embodiment, non-limiting examples of the polymers and/or biopolymers include: carboxy methyl cellulose (CMC), cotton fibres, alginic acid and salts thereof (e.g. Ca/Na), gelatin, collagen, polyesters, nylons and fibres thereof, synthetic hydrogels, poloxamers, polyethylene glycol and polypropylene glycol.

In another embodiment, this invention provides a medical device of this invention (comprising a coated substrate of this invention as referred hereinabove) for use in inhibiting or preventing biofilm formation or growth.

In one embodiment, this invention provides a method for inhibition of bacteria, the method comprising the step of contacting the bacteria with the packaging composition (comprising a coated substrate of this invention as referred hereinabove) of this invention.

In another embodiment, this invention provides a packaging composition (comprising a coated substrate of this invention as referred hereinabove) for use in inhibiting bacteria.

In one embodiment, this invention provides a method for treating, breaking down or killing biofilm or bacteria within, comprising applying onto a susceptible or infected surface or a medical device the packaging composition (comprising a coated substrate of this invention as referred hereinabove) of this invention.

In another embodiment, this invention provides packaging composition (comprising a coated substrate of this invention as referred hereinabove) of this invention for use in treating, breaking down or killing biofilm or bacteria within.

Applications out of the medical field may for example be in clothing (e.g. for sports or outdoor activity; to prevent bacteria-induced sweat odor), athlete shoes or the inner part of a shoe wherein bacteria tend to collect, sportswear and clothing for outdoor activity, tooth brushes and any brush that are in contact with the human body, air and water filters, water treatment and distribution systems, pet cages as well as other veterinary items, etc.

Additional application would be substrates with a smooth coated surface (e.g. car paint as the coating). In one embodiment, substrate coated with a smooth coating (surface) is prepared by providing the coated substrate, melting the coating (only), spreading the melted coating on top of the substrate and cooling it to afford a substrate coated with a smooth coating.

In some embodiments, the anti-microbial coated substrates of this invention affect annihilation of at least about 99% of the contacted bacteria, preferably, at least about 99.99% of the contacted bacteria.

It was further surprisingly discovered that the particles within compositions/coated substrates/medical devices of this invention maintain high anti-microbial properties over time without leaching out and with no alteration of the properties of the hosting matrix. Such particles demonstrate enhanced anti-bacterial activity originating from the presence of closely packed anti-bacterial groups on a given particle's surface.

Medical Devices of this Invention

In one embodiment, this invention further provides a medical device comprising a coated substrate of this invention. In one embodiment, non-limiting examples for medical devices of this invention are catheters, stents, surgical mesh, breast implants, joint replacements, artificial bones, artificial blood vessels, artificial heart valves (cardiology), artificial skin, plastic surgery implants or prostheses, intra uterin devices (gynecology), neurosurgical shunts, contact lenses (ophthalmology), intraocular lenses, ocular prosthesis, uretral stents, coating for subcutaneous (such as orthopedic or dental) implants, insulin pumps, contraceptives, pacemakers, tubing and canulas used for intra venous infusion, tubing and canulas used for dialysis, surgical drainage tubing, urinary catheters, endotracheal tubes, wound covering (dressing and adhesive bandage) and treatment (e.g. gels, ointments, pastes and creams for wound care which reduce biofilm and bacteria to aid wound healing) materials, sutures, catheters of all kinds that are inserted temporarily or permanently in blood vessels as well as the urinary system, shunt for use in brain applications, surgical gloves, tips for ear examination, statoscope ends and other elements used by the medical personnel; tooth brushes, tooth pick, dental floss, interdental and tongue brushes, surgical sutures, metal surgical tools, non-surgical medical devices, dental, and orthopedic metal implants and wires and surgical drains, syringes, trays, tips, gloves and other accessories used in common medical and dental procedures. In another embodiment, the wound dressing comprises/is the coated substrate which comprises the anti-microbial particles as described above and polymers and/or biopolymers. In another embodiment, non-limiting examples of the polymers and/or biopolymers include: carboxy methyl cellulose (CMC), cotton fibres, alginic acid and salts thereof (e.g. Ca/Na), gelatin, collagen, polyesters, nylons and fibres thereof, synthetic hydrogels, poloxamers, polyethylene glycol and polypropylene glycol. In one embodiment, this invention further provides a medical device comprising a dental appliance. In one embodiment, this invention further provides a medical device comprising an orthodontic appliance. The dental appliance and the orthodontal appliance comprise the coated substrates of this invention. In some embodiments, the orthodontal appliance include an aligner for accelerating the tooth aligning, a bracket, a dental attachment, a bracket auxiliary, a ligature tie, a pin, a bracket slot cap, a wire, a screw, a micro-staple, cements for bracket and attachments and other orthodontic appliances, a denture, a partial denture, a dental implant, a periodontal probe, a periodontal chip, a film, or a space between teeth. In some embodiments, the dental appliance include a mouth guard, used to prevent tooth grinding (bruxer, Bruxism), night guard, an oral device used for treatment/prevention sleep apnea, teeth guard used in sport activities.

In one embodiment, this invention further provides a trans dermal medical device such as orthopedic external fixation screws and wires used for bone fixations and stabilization and trans mucosal elements used in dental implants such as healing caps, abutments (such as multiunit), for screw retained or for cement retained dental prosthesis.

In one embodiment, this invention further provides a medical device comprising an endoscope (rigid and flexible), including, and not limited to a colonoscope, gastroscope, duodenoscope, bronchoscope, cystoscope, ENT scopes, laporoscope, laryngoscope and similar instruments for examination or treatment the inside of the patient's body, including any parts thereof, as well as accessories and other devices used in the procedure which either come in contact with body tissue or fluids; tubes, pumps, containers and connectors (used inside or outside the body) through which fluids, air or gas may be pumped into or suctioned out from the patient and could become contaminated by the patient or transfer contaminants from other patients; items such as brushes, trays, covers, tubes, connectors cabinets and bags used for reprocessing, cleaning, transporting and storing such equipment and can transmit or host biological contaminants, as well as filters for air or water used in dental or medical procedures, hospital surfaces (such as floors, tabletops), drapes, curtains, linen, handles and the like.

The antimicrobial property may protect the patient and the medical staff from cross contamination from patient to patient or from patient to the examiner. Self-sterilizing packaging for medicines and items that enter the operation room are also beneficial.

The following examples are presented in order to more fully illustrate the preferred embodiments of this invention. They should in no way, however, be construed as limiting the broad scope of this invention.

EXAMPLES

Example 1

Antimicrobial Activity of Glass Slides Coated with Polyvinyl Alcohol with Anti-Microbial Particles Two solutions of polyvinyl alcohol (PVA) were prepared:

1. 0.98 gr of PVA, 0.02 gr of anti-microbial 2QA POSS particles (represented below) and 9.00 ml of deionized water; and
2. 9.00 ml of deionized water (control).

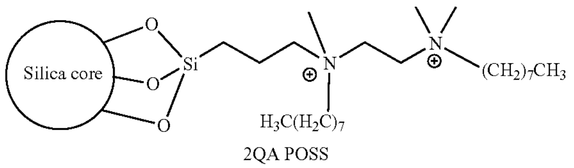

2QA POSS

Both samples were prepared by mixing until clear solution obtained using incubated shaker at 37° C.

Glass coverslips slides (2×2 cm) were coated with thin layer of prepared solutions, then water allowed to evaporate at 37° C. incubator overnight, resulting in uniform thin PVA film. 10 µl of *Enterococcus faecalis* (*E. faecalis*, ATCC 51299) in brain heart infusion broth (BHI), were applied onto dry PVA film, then spread over the samples' area. Subsequently, samples were incubated at 37° C. for 1 h to ensure full contact of the bacteria in the BHI with the PVA Surface. Samples were placed onto BHI agar sterile plates, when the inoculated PVA surface touched the agar. Plates were then incubated for 45 min, then treated slides removed and plates incubated at 37° C. overnight to develop the colonies imprinted from the samples.

Figure 18:
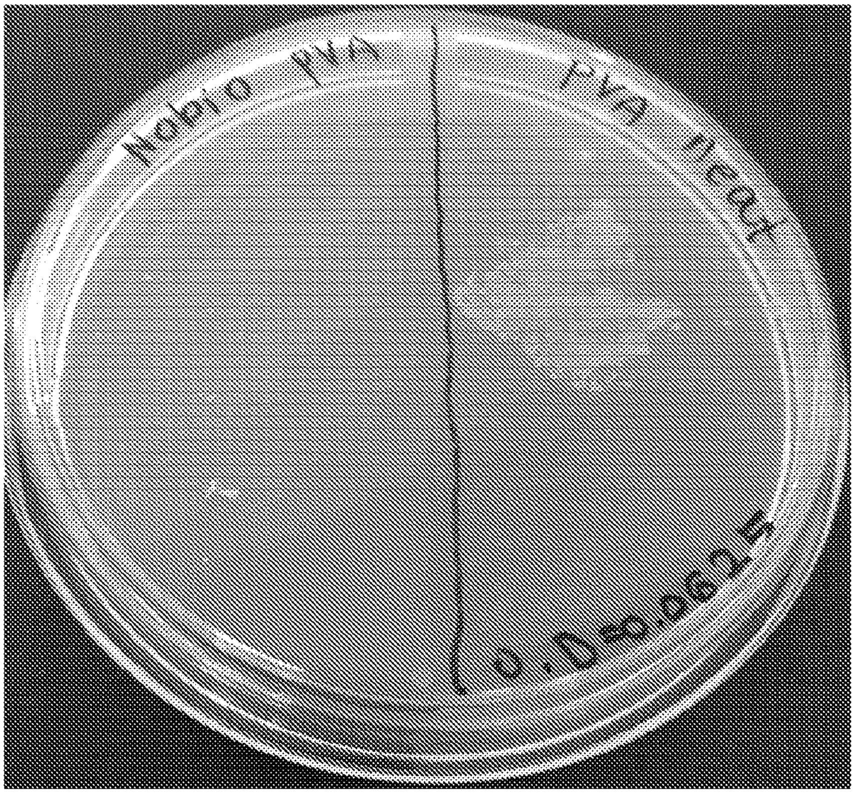
FIG. 18 depicts anti-microbial activity of glass coated with PVA containing 2% 2QA-POSS particles against *E. faecalis* when compared to glass coated with untreated PVA.

Each plate was divided into two parts, designated as Nobio (2QA POSS particles) and Control. Initial bacteria concentration that was used in this experiment was $2\times10^7$ CFU in 10 μl. Uncountable dense bacteria growth was observed for the control samples, while only few CFU detected at the Nobio side of the agar plate as shown in FIG. 18. The bacteria reduction for 2% Nobio particles in PVA was at least 6 logs.

In addition, 5 log reduction was found when these particles with polyvinylidene fluoride (PVDF) were dissolved in N-Methyl-2-pyrrolidone (NMP) and used in the same manner as above.

Example 2

Figure 19:
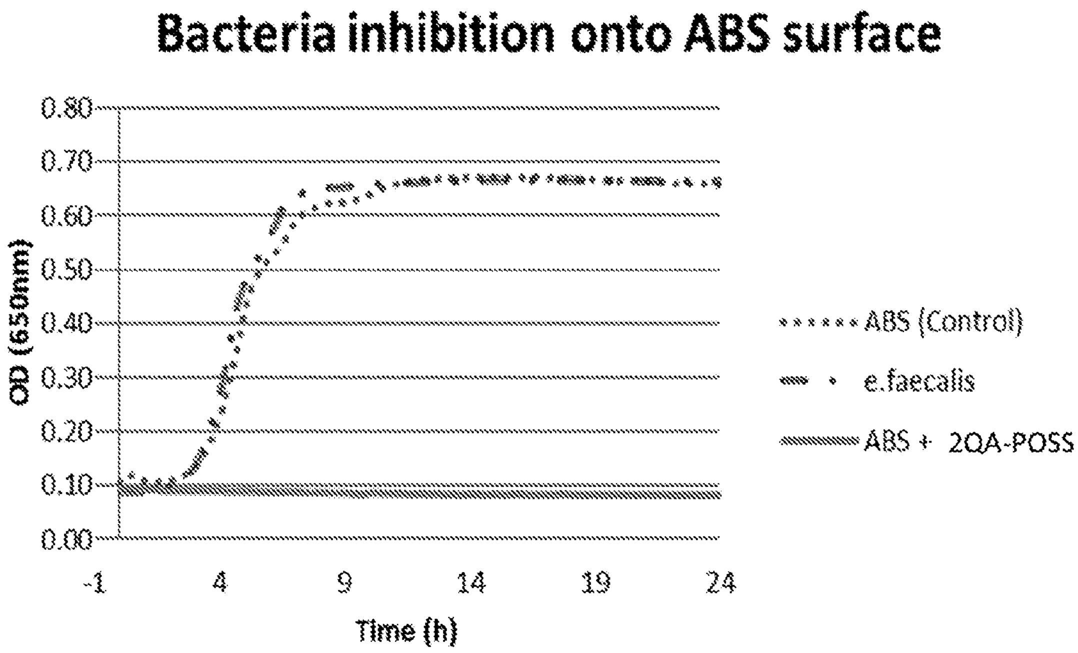
FIG. 19 depicts anti-microbial activity of acrylonitrile butadiene styrene (ABS) coated with ABS containing 2QA-POSS particles against *E. faecalis* when compared to untreated ABS.
Figure 20:
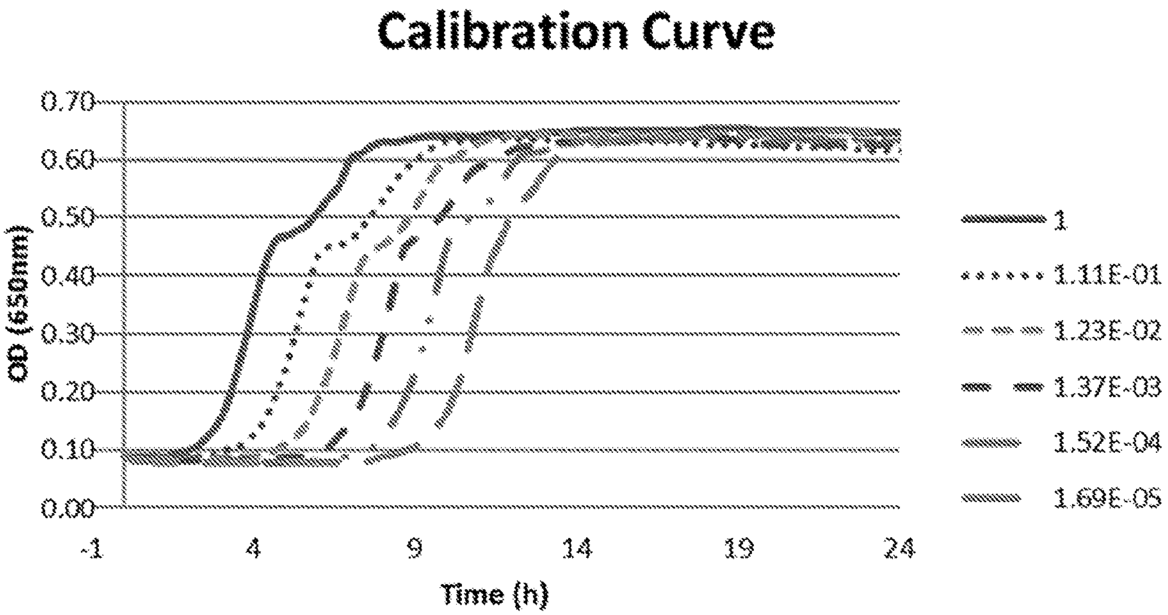
FIG. 20 depicts calibration curve, representing growing curves of *E. faecalis* that was used in the DCT test and performed simultaneously at serial dilutions of acrylonitrile butadiene styrene (ABS) coated with ABS containing 2QA-POSS particles.

Antimicrobial Activity of Acrylonitrile Butadiene Styrene (ABS) Coated with ABS with Anti-Microbial Particles Samples of acrylonitrile butadiene styrene (ABS) were coated with ABS and 2QA POSS particles (see Example 1) solution in dichloromethane (DCM). Than, all the DCM was evaporated, leaving thin layer of ABS coating with 2QA POSS particles. Coated ABS and untreated ABS (control) samples were tested for antibacterial characteristics according to the direct contact test (DCT) protocol (Weiss E I, S. M. F. Z., 1996. Assessment of antibacterial activity of endodontic sealers by a direct contact test. *Endod Dent Traumatol*., pp. 179-184). The results are represented in FIGS. 19-20. Bacteria growth inhibition of at least 5 logs observed for coated ABS samples. Zero inhibition was observed for control samples.

Figure 21:
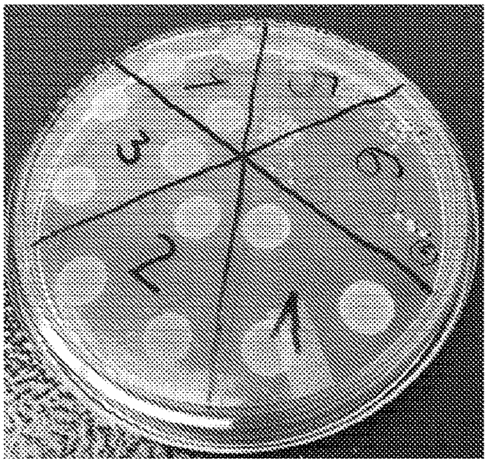
FIG. 21 depicts serial dilutions of *E. faecalis* that was used to test acrylonitrile butadiene styrene (ABS) coated with polymerized epoxy-amine blend containing 2QA-POSS particles.
Figure 22:
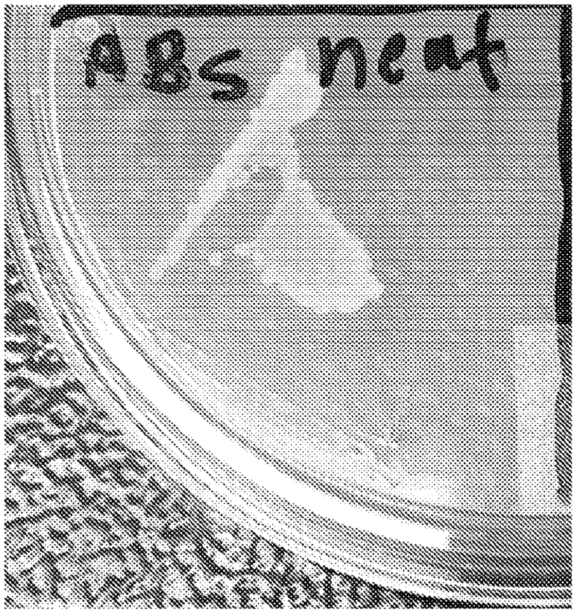
FIG. 22 depicts bacteria colonies growth after being imprinted from control (untreated) acrylonitrile butadiene styrene (ABS) fragments.
Figure 23:
FIG. 23 depicts imprints duplicated (F and C) from epoxy-amine blend coated ABS fragments with 2QA-POSS particles.

Samples of ABS fragments taken from commercial switch covers were coated by epoxy/amine blend and 2QA POSS particles and allowed to polymerize. Untreated samples were used as control. Bacteria suspension was applied onto the samples' surface and allowed to evaporate for 1 h. Samples then were imprinted onto the agar broth petri dish for 15 min. The bacteria colonies were visually examined. At least 5 logs inhibition of the bacteria growth was observed for the treated samples when compared to the control as shown in FIGS. 21-23.

Example 3

Antimicrobial Activity of Polyvinylchloride (PVC) Coated with PVC with Anti-Microbial Particles Polyvinylchloride (PVC) tube fragments (2 cm long) were dipped into solution of dissolved PVC with 2QA POSS (see Example 1) particles in Dichloromethane (PVC+2QA POSS). Subsequently, solvent was evaporated at 120° C. and transparent layer of PVC+2QA POSS particles over the original PVC tube, was obtained. Samples (n=8) were assessed for antibacterial activity according to the direct contact test (DCT) (Weiss E I, S. M. F. Z., 1996. Assessment of antibacterial activity of endodontic sealers by a direct contact test. *Endod Dent Traumatol*., pp. 179-184) using *Enterococcus faecalis* (*E. faecalis*) as the representative test organism. Untreated PVC tube and Polystyrene (the polymer of the microtiter plate), served as control surfaces. The inoculum size was at least $5\times10^6$ CFU of *E. faecalis*.

Figure 24:
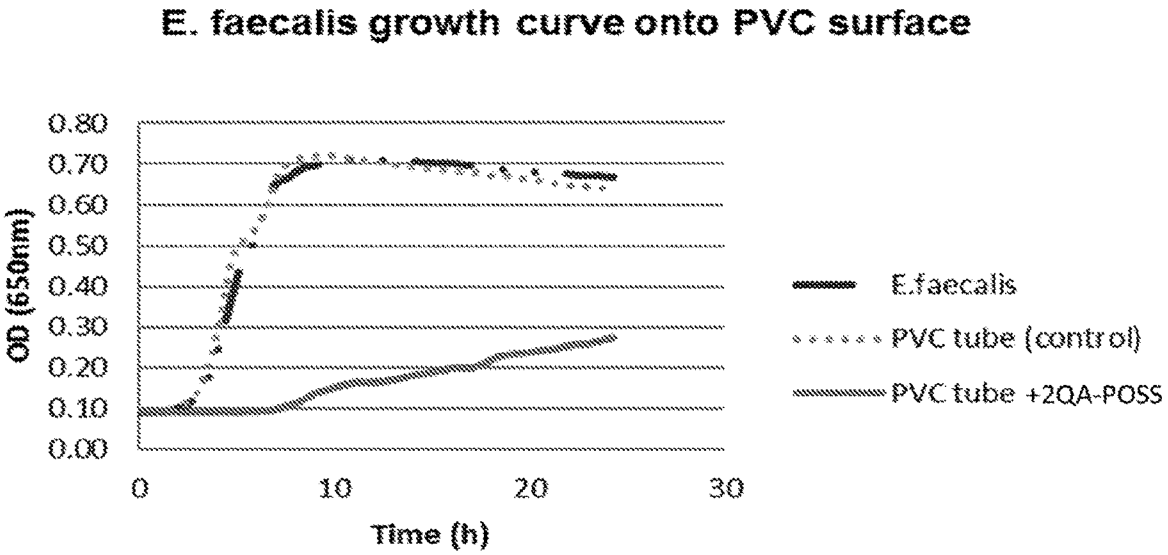
FIG. 24 depicts bacteria growth inhibition observed for polyvinylchloride (PVC) samples dip-coated with PVC+2QA-POSS particles when compared to untreated PVC tube fragments.
Figure 25:
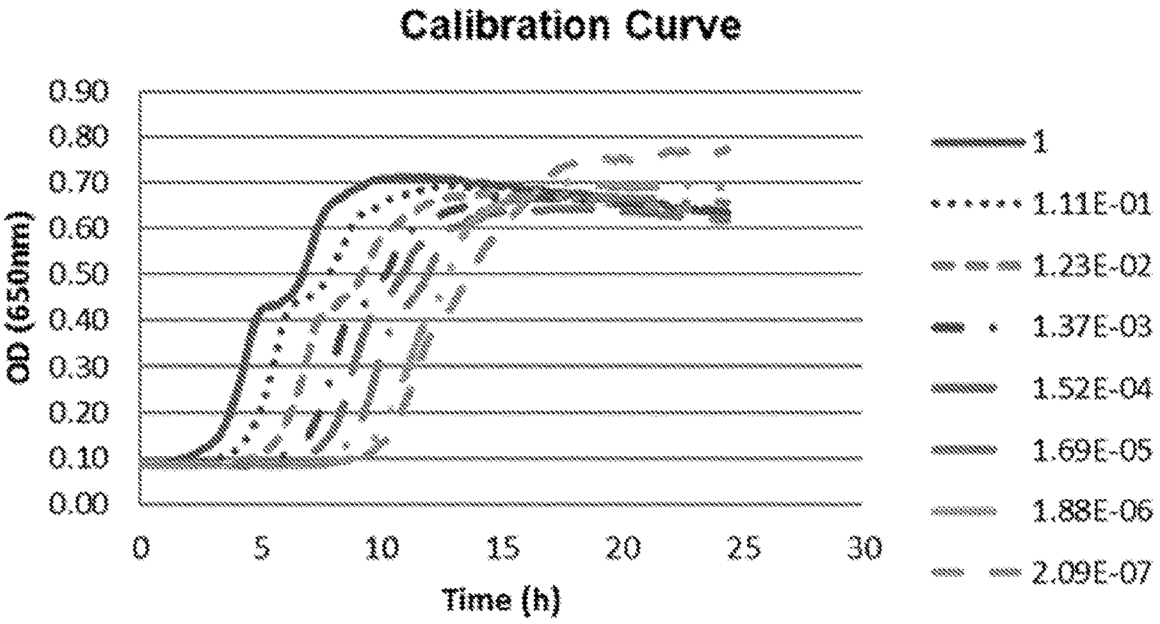
FIG. 25 depicts *E. faecalis* normal growth curve at X9 dilutions as measured in the microtiter plate shown in FIG. 24.

Results are depicted in FIG. 24. PVC dip-coated with PVC+2QA-POSS particles demonstrated complete inhibition of bacteria growth for approximately 8 hrs, correlating to at least 6 log reductions, according to the calibration curves (FIG. 25). Growth after 8 hrs was observed only on 2 out of 8 samples (graph depicts average for all 8 samples).

Example 4

Antimicrobial Activity of Methylmethacrylate Acrylonitrile Butadiene Styrene (MABS) Coated with MABS with Anti-Microbial Particles Methylmethacrylate acrylonitrile butadiene styrene (MABS) pellets were extruded using twin-cone compounder at 25 RPM, 220° C. Next, short fragments of obtained strand were press-molded to thin DCT specimens. Eight specimens were dipped in solution of MABS with 2QA-POSS particles in dichloromethane and then the solvent was evaporated at 120° C. and thin transparent layer of MABS containing 2QA-POSS particles (MABS+2QA-POSS) over the original MABS specimen was obtained. Eight untreated specimens were used as control group. Bacteria growth inhibition was examined by the DCT against *E. faecalis*. Untreated MABS and Polystyrene (the polymer of the microtiter plate), served as control surfaces. The inoculum size was at least $5\times10^6$ CFU of *E. faecalis*.

Figure 26:
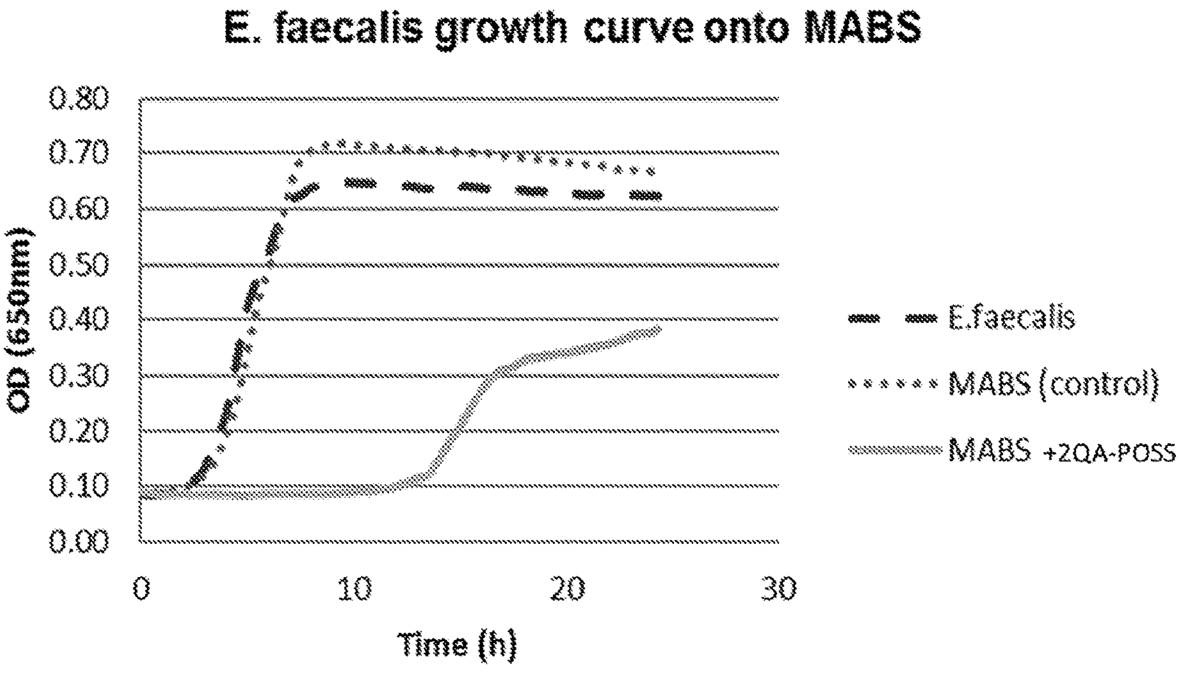
FIG. 26 depicts bacteria growth inhibition obtained for methylmethacrylate acrylonitrile butadiene styrene (MABS) samples coated with MABS and 2QA-POSS particles when compared to untreated PVC tube fragments.
Figure 27:
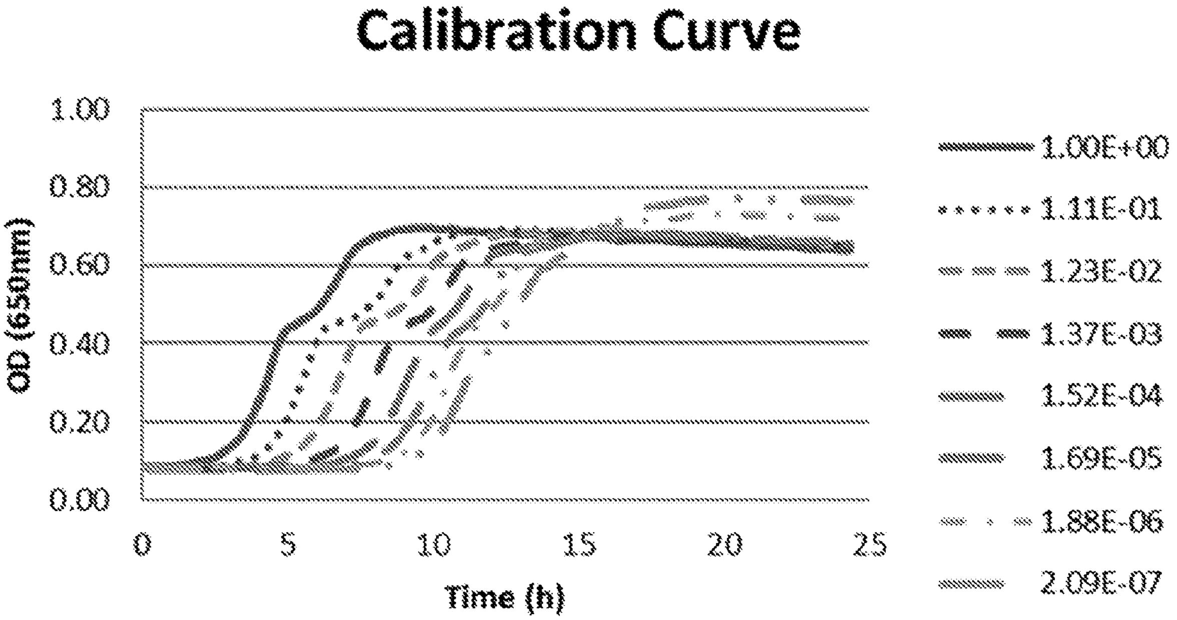
FIG. 27 depicts *E. faecalis* normal growth curve at X9 dilutions as measured in the microtiter plate shown in FIG. 26.

Results are summarized in FIG. 26. MABS coated with MABS+Nobio particles demonstrated complete inhibition of bacteria growth for approximately 12 hrs, correlating to more than 7 log reductions, according to the calibration curves (FIG. 27).

Example 5

Bacterial Growth of *E. faecalis* on Epoxy Coated ABS Coupons

Figure 28:
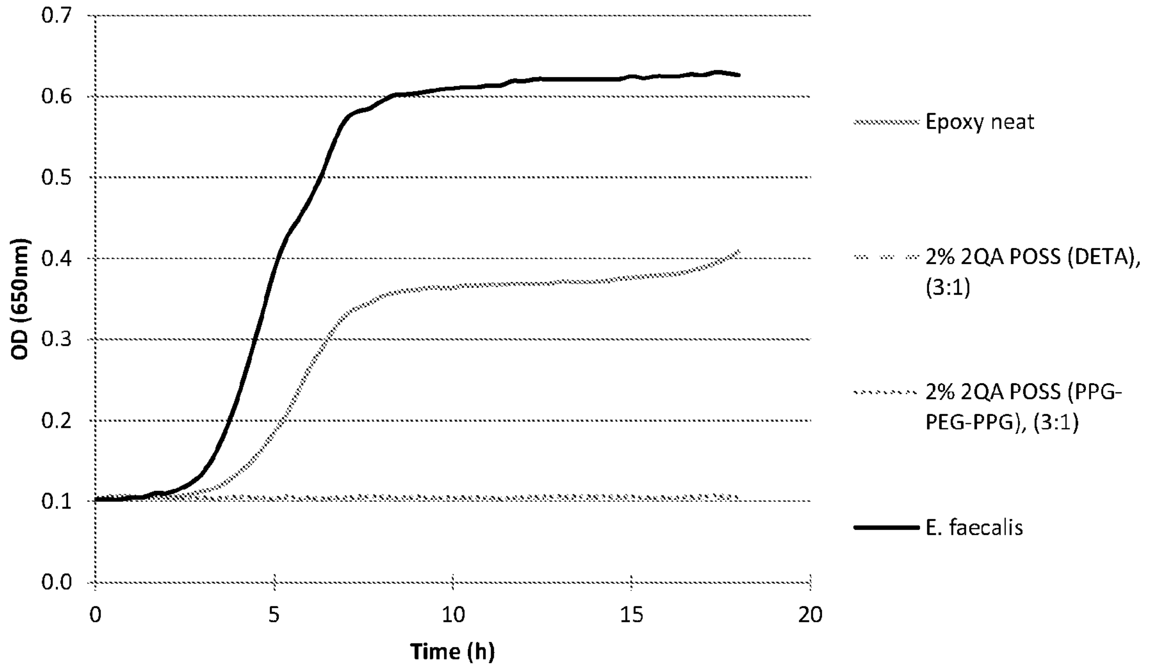
FIG. 28 depicts direct contact test (DCT) diagram of bacterial growth of *E. faecalis* on acrylonitrile-butadiene-styrene (ABS) coupons coated with epoxy with and without 2QA POSS particles (without initial dispersion). "DETA" is diethylenetriamine and "PPG-PEG-PPG" is polypropylene glycol-polyethylene glycol-polypropylene glycol diamine. Ratios in the legend refer to diglycidyl ether of bisphenol A (DGEBA) to PEG 400 Diglycidyl ether weight ratios.

Epoxy resin was produced by a reaction between two components: one part consists an amine functional group and the other part consists an epoxy functional group. When the two components reacted together, the epoxy ring was opened by a nucleophilic attach of the amine to produce a crosslinked network. 2QA POSS particles as described in Example 1 were dispersed once in diethylenetriamine (DETA) and in a different experiment, in triblock copolymer of polypropylene glycol-polyethylene glycol-polypropylene glycol (PPG-PEG-PPG) diamine. After full dispersion, a mixture of diglycidyl ether of bisphenol A (DGEBA) with PEG 400 Diglycidyl ether in a weight ratio of 3:1, was added. The mixture was then coated on acrylonitrile-butadiene-styrene (ABS) coupons and tested in the direct contact test (DCT) for antimicrobial activity. It can be seen in FIG. 28 that the neat sample (without 2QA POSS particles) shows a classic logarithmic bacteria growth while samples containing 2QA POSS demonstrate a complete inhibition of bacterial growth.

Figure 29:
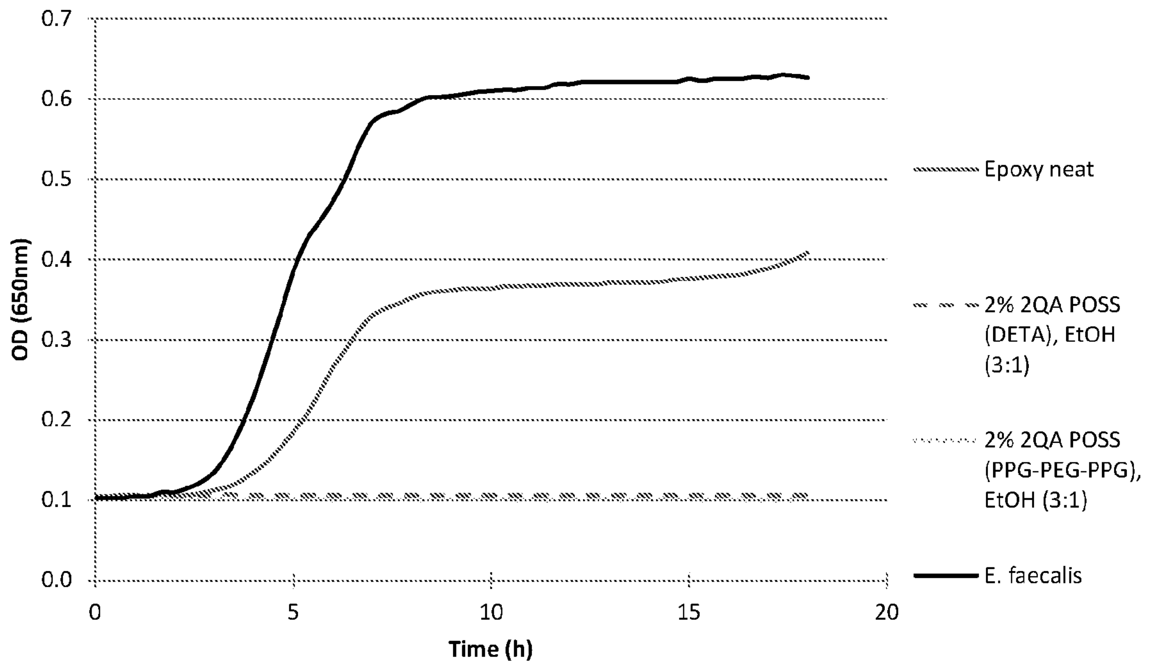
FIG. 29 depicts direct contact test (DCT) diagram of bacterial growth of *E. faecalis* on ABS coupons coated with epoxy with and without 2QA POSS particles (with initial dispersion of the particles in ethanol). "DETA" is diethylenetriamine and "PPG-PEG-PPG" is polypropylene glycol-polyethylene glycol-polypropylene glycol diamine. Ratios in the legend refer to diglycidyl ether of bisphenol A (DGEBA) to PEG 400 Diglycidyl ether weight ratios.
Figure 30:
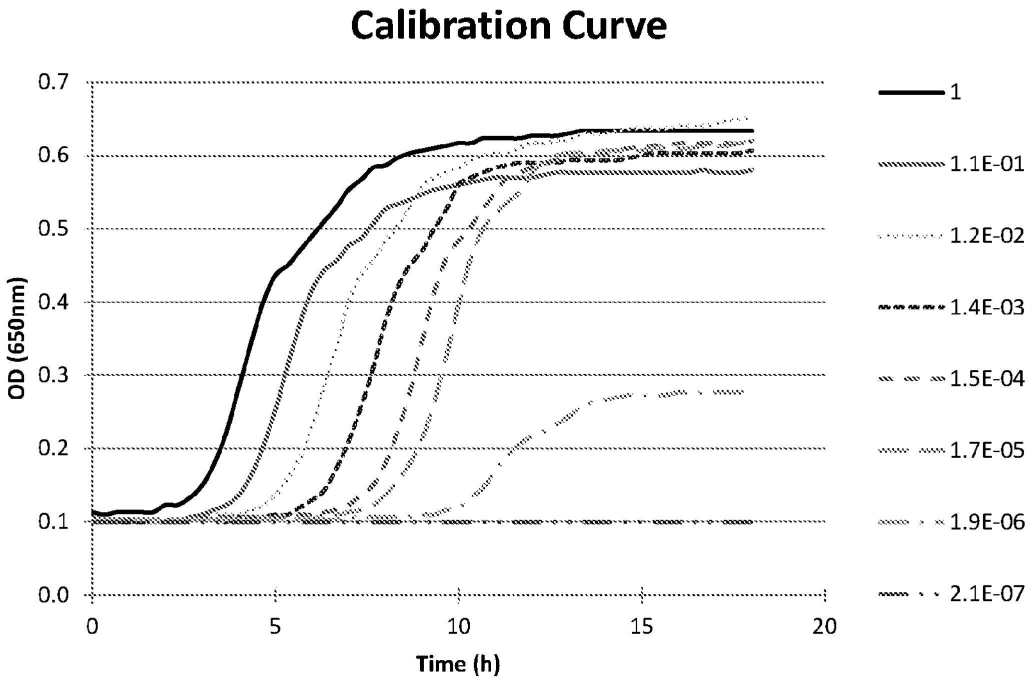
FIG. 30 depicts calibration curve for the direct contact test (DCT) illustrated in FIGS. 28-29 where the name of each curve ("1", "1.3E-01" . . . ) corresponds to *E. faecalis* relative concentration.

In additional experiment, 2QA POSS particles were dispersed in ethanol. After full dispersion, DETA was added to the mixture or in a different mixture block copolymer of PPG-PEG-PPG diamine was added. A mixture of DGEBA with PEG 400 Diglycidyl ether in the ratio of 3:1 was added to the dispersion. The mixture was then coated on ABS coupons and tested in the DCT method for antimicrobial activity. It can be seen in FIG. 29 that the neat sample (without 2QA POSS particles) shows a classic logarithmic bacteria growth while samples containing 2QA POSS demonstrate a complete inhibition of bacterial growth. A calibration curve for the DCT of the above experiments (without and with dispersion of the particles in ethanol) is presented in FIG. 30.

Figure 31:
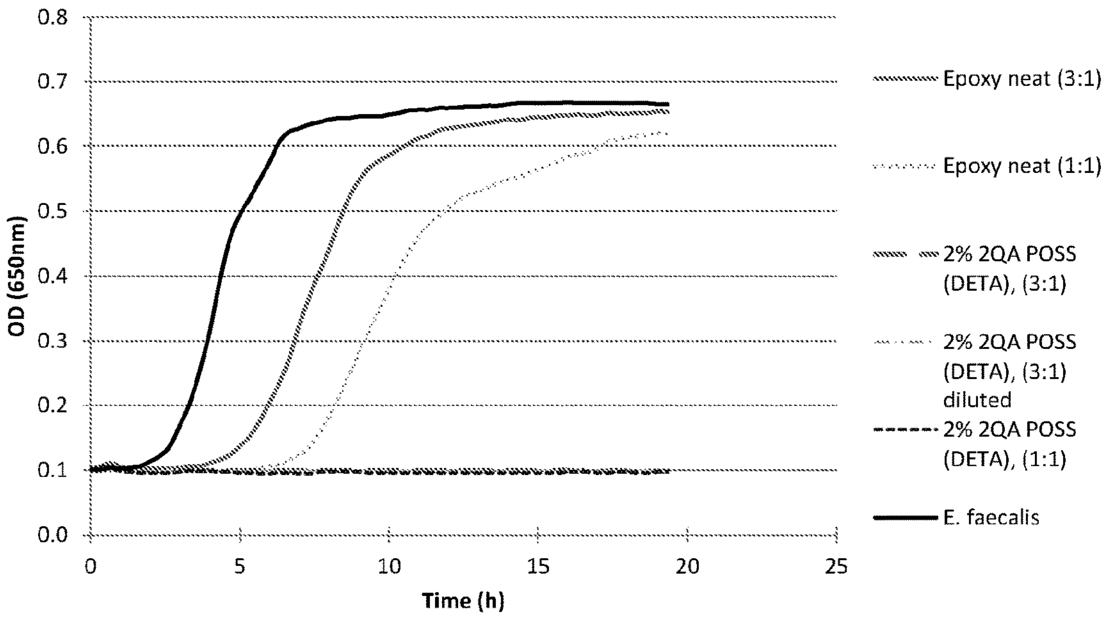
FIG. 31 depicts direct contact test (DCT) diagram of bacterial growth of *E. faecalis* on ABS coupons coated with epoxy with and without 2QA POSS particles (with initial dispersion of the particles in ethanol and dilution with ethyl acetate). "DETA" is diethylenetriamine. Ratios in the legend refer to diglycidyl ether of bisphenol A (DGEBA) to PEG 400 Diglycidyl ether weight ratios.
Figure 32:
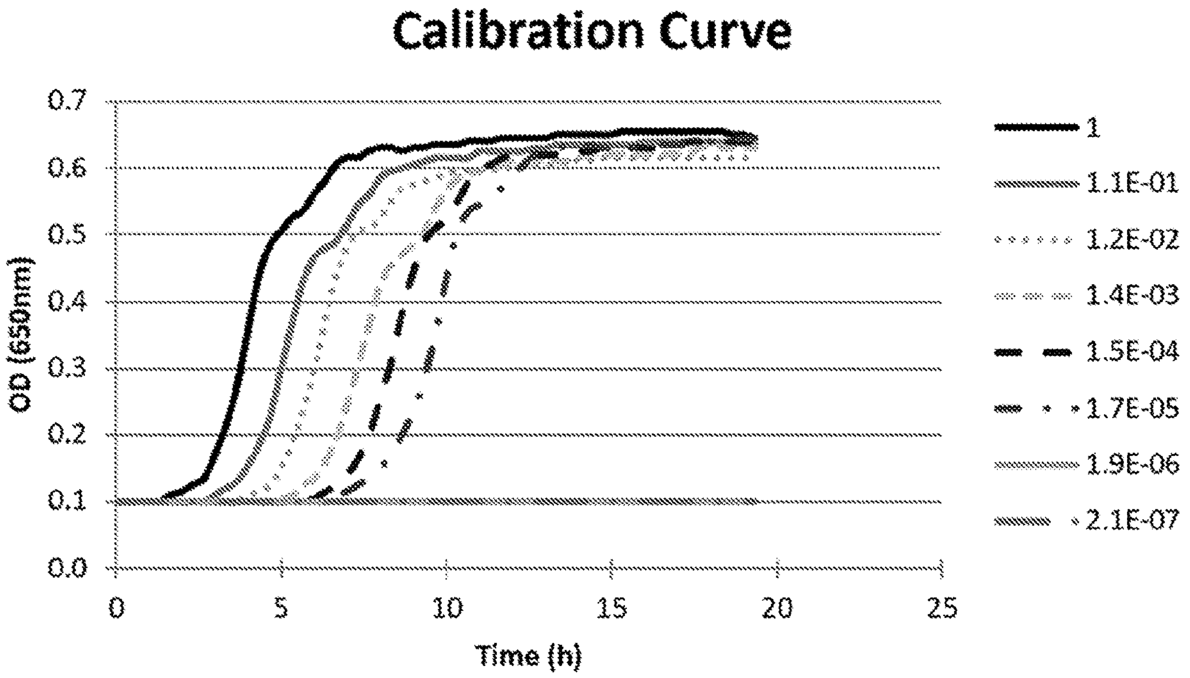
FIG. 32 depicts calibration curve for the direct contact test (DCT) illustrated in FIG. 31 where the name of each curve ("1", "1.3E-01" . . . ) corresponds to *E. faecalis* relative concentration.

In one further experiment, 2QA POSS particles were dispersed in ethanol. After full dispersion, diethylenetriamine was added to the dispersion. A mixture of DGEBA and PEG 400 Diglycidyl ether in the ratio of 3:1 was added to the dispersion afterwards and in another experiment in a ratio of 1:1. The mixtures were diluted in ethyl acetate for easier application. The mixtures were then coated on ABS coupons and tested in the DCT method for antimicrobial activity. It can be seen in FIG. 31 that the neat sample (without 2QA POSS particles) shows a classic logarithmic bacteria growth while samples containing 2QA POSS demonstrate a complete inhibition of bacterial growth. A calibration curve for the DCT of the above experiment (dispersion of the particles in ethanol and dilution with ethyl acetate) is presented in FIG. 32.

While certain features of this invention have been illustrated and described herein, many modifications, substitutions, changes, and equivalents will now occur to those of ordinary skill in the art. It is, therefore, to be understood that the appended claims are intended to cover all such modifications and changes as fall within the true spirit of this invention.

What is claimed is:

1. A coating comprising anti-microbial particles and a matrix, wherein the particles comprise:

(i) an inorganic core; and (ii) an anti-microbial active unit chemically bound to the core;

wherein the anti-microbial active unit is connected via a bond or via a third linker to the core;

wherein the anti-microbial active unit comprises a monomeric unit comprising an anti-microbial active group; and wherein the number of the anti-microbial active groups per each anti-microbial active unit is between 1-200;

wherein said particles are represented by structure (1) or (I):

(1)

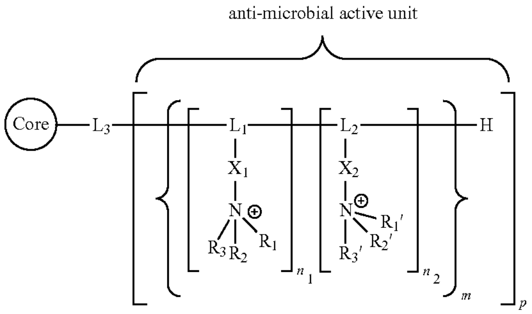

wherein the core is an inorganic material;

$L_1$ is a first linker or a bond;

$L_2$ is a second linker;

$L_3$ is a third linker or a bond;

$R_1$ and $R_1$' are each independently alkyl, terpenoid, cycloalkyl, aryl, heterocycle, alkenyl, alkynyl or any combination thereof;

$R_2$ and $R_2$' are each independently alkyl, terpenoid, cycloalkyl, aryl, heterocycle, alkenyl, alkynyl or any combination thereof;

$R_3$ and $R_3$' are each independently nothing, hydrogen, alkyl, terpenoid moiety, cycloalkyl, aryl, heterocycle, a conjugated alkyl, alkenyl, alkynyl or any combination thereof; wherein if $R_3$ or $R_3$' are nothing, the nitrogen is not charged;

$X_1$ and $X_2$ is each independently a bond, alkylene, alkenylene, or alkynylene;

p is a surface density, defined by the number of anti-microbial active units per one sq nm of the core surface, wherein said density is of between 0.01-30 anti-microbial units per one sq nm of the core surface of the particle;

$n_1$ is each independently an integer between 0 to 200;

$n_2$ is each independently an integer between 0 to 200;

wherein $n_1+n_2\geq 2$; and m is an integer between 1 to 200 and the repeating unit is the same or different; or (I)

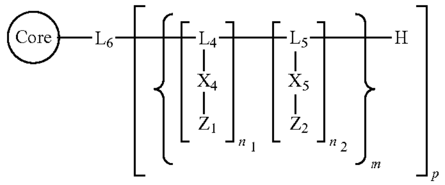

wherein the core is an inorganic material;

$L_4$ is a first linker or a bond;

$L_5$ is a second linker;

$L_6$ is a third linker or a bond;

$Z_1$

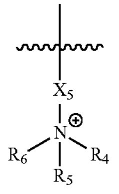

or

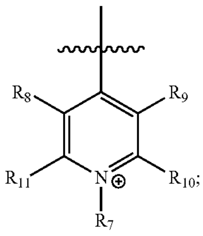

$Z_2$ is

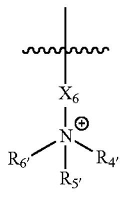

or

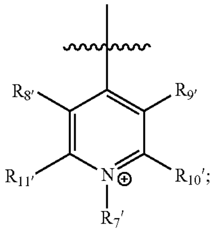

$R_4$ and $R_4$' are each independently methyl, $CF_3$, perhaloalkyl, aryl, benzyl, 2,2-disubstituted $C_3$-$C_{20}$ alkyl, 2,2,2-trisubstituted ethyl, —$CH_2C$(═O)OR, —$CH_2C$(═O) OC(═O)R, —$CH_2C$(═S)OR, —$CH_2C$(═O)SR, —C(═O)OR, —C(═O) OC(═O)R, —C(═S)OR, —C(═O) SR, —C(═O)—R, —C(═S)—R, —$CH_2C$(═O)R, —$CH_2C$(═S)R, —$CH_2CF_3$, —$CH_2NO_2$, 1-alkenyl, 1-alkynyl, 2-alkenyl, 2-alkynyl or any combination thereof;

$R_5$ and $R_5$' are each independently methyl, $CF_3$, perhaloalkyl, aryl, benzyl, 2,2-disubstituted $C_3$-$C_{20}$ alkyl, 2,2,2-trisubstituted ethyl, —$CH_2C$(═O)OR, —$CH_2C$(═O) OC(═O)R, —$CH_2C$(═S)OR, —$CH_2C$(═O) SR, —C(═O)OR, —C(═O) OC(═O)R, —C(═S) OR, —C(═O) SR, —C(═O)—R, —C(═S)—R, —$CH_2C$(═O)R, —$CH_2C$(═S)R, —$CH_2CF_3$, —$CH_2NO_2$, 1-alkenyl, 1-alkynyl, 2-alkenyl, 2-alkynyl or any combination thereof;

$R_6$ and $R_6$' are each independently absent, methyl, $CF_3$, perhaloalkyl, 2,2-disubstituted $C_3$-$C_{20}$ alkyl, 2,2,2-trisubstituted ethyl, —$CH_2C$(═O)OR, —$CH_2C$(═O) OC(═O)R, —$CH_2C$(═S)OR, —$CH_2C$(═O) SR, —C(═O)OR, —C(═O) OC(═O)R, —C(═S)OR, —C(═O) SR, —C(═O)—R, —C(═S)—R, —$CH_2C$(═O)R, —$CH_2C$(═S)R, —$CH_2CF_3$, —$CH_2NO_2$, terpenoid moiety, cycloalkyl, aryl, phenyl, benzyl, heterocycle, a conjugated alkyl, 1-alkenyl, 1-alkynyl, 2-alkenyl, 2-alkynyl or any combination thereof;

$R_7$ and $R_7$' are each independently methyl, $CF_3$, perhaloalkyl, aryl, benzyl, 2,2-disubstituted $C_3$-$C_{20}$ alkyl, 2,2,2-trisubstituted ethyl, —$CH_2C$(═O)OR, —$CH_2C$(═O) OC(═O)R, —$CH_2C$(═S)OR, —$CH_2C$(═O) SR, —C(═O)OR, —C(═O) OC(═O)R, —C(═S) OR, —C(═O) SR, —C(═O)—R, —C(═S)—R, —$CH_2C$(═O)R, —$CH_2C$(═S)R, —$CH_2CF_3$, —$CH_2NO_2$, 1-alkenyl, 1-alkynyl, 2-alkenyl, 2-alkynyl or any combination thereof;

$R_8$ and $R_8$' are each independently H, alkyl, terpenoid moiety, cycloalkyl, aryl, heterocycle, a conjugated alkyl, alkenyl, alkynyl or any combination thereof;

$R_9$ and $R_9$' are each independently H, alkyl, terpenoid moiety, cycloalkyl, aryl, heterocycle, a conjugated alkyl, alkenyl, alkynyl or any combination thereof, $R_{10}$ and $R_{10}$' are each independently H, alkyl, terpenoid moiety, cycloalkyl, aryl, heterocycle, a conjugated alkyl, alkenyl, alkynyl or any combination thereof;

$R_{11}$ and $R_{11}$' are each independently H, alkyl, terpenoid moiety, cycloalkyl, aryl, heterocycle, a conjugated alkyl, alkenyl, alkynyl or any combination thereof;

$X_3$ and $X_4$ are each independently a bond, alkylene, arylene, alkenylene, alkynylene or any combination thereof;

$X_5$ and $X_6$ are each independently a bond, —O—C(═O)—, methylene, —O—C(═O)—$CH_2$—, 2,2-disubstituted $C_2$-$C_{20}$ alkylene, arylene, phenylene, benzylene, cycloalkylene, a heterocycle, a conjugated alkylene, a terpenoid moiety, 1-alkenylene, 1-alkynylene, 2-alkenylene, 2-alkynylene or any combination thereof, R is alkyl, aryl, cycloalkyl, heterocycle or any combination thereof;

p is a surface density, defined by the number of anti-microbial active unit per one sq nm of the core surface, wherein said density is of between 0.01-30 anti-microbial units per one sq nm of the core surface of the particle;

$n_1$ is each independently an integer between 0 to 200;

$n_2$ is each independently an integer between 0 to 200; wherein $n_1+n_2 \geq 1$; and m is an integer between 1 to 200 and the repeating unit is the same or different.

2. The coating of claim 1, wherein said matrix is an organic or inorganic polymer.

3. The coating of claim 1, wherein said coating has a thickness of between 5 and 1000 nm.

4. The coating of claim 1, wherein the weight ratio of the particles to the whole coating which comprises said matrix and particles is between 0.25 and 10%.

* * * * *